United States Patent
Metzger

(10) Patent No.: US 9,693,788 B2
(45) Date of Patent: *Jul. 4, 2017

(54) INSTRUMENTATION FOR KNEE RESECTION

(71) Applicant: Biomet Manufacturing, LLC, Warsaw, IN (US)

(72) Inventor: Robert Metzger, Wakarusa, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 94 days.

This patent is subject to a terminal disclaimer.

(21) Appl. No.: 14/703,083

(22) Filed: May 4, 2015

(65) Prior Publication Data

US 2015/0305754 A1    Oct. 29, 2015

Related U.S. Application Data

(60) Continuation of application No. 14/047,361, filed on Oct. 7, 2013, now Pat. No. 9,023,053, which is a
(Continued)

(51) Int. Cl.
*A61B 17/15* (2006.01)
*A61B 17/17* (2006.01)
(Continued)

(52) U.S. Cl.
CPC ........ *A61B 17/1764* (2013.01); *A61B 17/142* (2016.11); *A61B 17/155* (2013.01);
(Continued)

(58) Field of Classification Search
CPC . A61B 17/1764; A61B 17/142; A61B 17/155; A61B 17/157
(Continued)

(56) References Cited

U.S. PATENT DOCUMENTS

| 1,763,730 A | 6/1930 | Von Lackum |
| 1,959,615 A | 5/1934 | Derrah |

(Continued)

FOREIGN PATENT DOCUMENTS

| CH | 117960 | 5/1927 |
| DE | 337437 | 5/1921 |

(Continued)

OTHER PUBLICATIONS

"U.S. Appl. No. 14/047,361, Examiner Interview Summary mailed Nov. 12, 2014", 3 pgs.

(Continued)

*Primary Examiner* — Pedro Philogene
*Assistant Examiner* — David C Comstock
(74) *Attorney, Agent, or Firm* — Schwegman Lundberg & Woessner, P.A.

(57) ABSTRACT

A system for performing a resection of a selected portion of an anatomy with a resection instrument. The system includes a first member, a first movement defining portion defined by the first member, a second member, and a second movement defining portion of the second member. The first member is fixable to the selected portion of the anatomy. The second member is configured to cooperate with the first member. The first movement defining portion and the second movement defining portion are operable to allow the second member to be moveable relative to the first member from a first position to a second position. The resection instrument is positionable relative to the second member in the first position and in the second position to form a selected resection of the selected portion of the anatomy.

14 Claims, 28 Drawing Sheets

Related U.S. Application Data division of application No. 11/337,861, filed on Jan. 23, 2006, now Pat. No. 8,551,100, which is a continuation-in-part of application No. 11/058,527, filed on Feb. 15, 2005, now Pat. No. 7,789,885, which is a continuation-in-part of application No. 10/931,220, filed on Aug. 31, 2004, now Pat. No. 7,887,542, which is a continuation-in-part of application No. 10/345,102, filed on Jan. 15, 2003, now Pat. No. 7,837,690.

(51) Int. Cl.
  *A61B 17/16*   (2006.01)
  *A61B 17/14*   (2006.01)
  *A61B 17/02*   (2006.01)

(52) U.S. Cl.
  CPC ........ *A61B 17/157* (2013.01); *A61B 17/1675* (2013.01); *A61B 17/02* (2013.01)

(58) Field of Classification Search
  USPC ..... 606/79, 82, 84, 85, 86 R, 87, 88, 89, 96, 606/102; 623/20.14, 20.32
  See application file for complete search history.

(56) References Cited

U.S. PATENT DOCUMENTS

| | | |
|---|---|---|
| 2,433,815 A | 12/1947 | LaForge |
| 2,455,655 A | 12/1948 | Carroll |
| 2,702,550 A | 2/1955 | Rowe |
| 2,724,326 A | 11/1955 | Long |
| 2,951,482 A | 9/1960 | Sullivan |
| 2,955,530 A | 10/1960 | Nilo |
| 3,048,522 A | 8/1962 | Velley |
| 3,229,006 A | 1/1966 | Nohl |
| 3,514,791 A | 6/1970 | Sparks |
| 3,554,197 A | 1/1971 | Dobbie |
| 3,624,747 A | 11/1971 | McKnight et al. |
| 3,631,596 A | 1/1972 | Glaus |
| 3,678,934 A | 7/1972 | Warfield et al. |
| 3,698,017 A | 10/1972 | Scales et al. |
| 3,703,036 A | 11/1972 | Karubian |
| 3,774,244 A | 11/1973 | Walker |
| 3,783,873 A | 1/1974 | Jacobs |
| 3,807,393 A | 4/1974 | McDonald |
| 3,811,449 A | 5/1974 | Gravlee et al. |
| 3,869,731 A | 3/1975 | Waugh et al. |
| 3,903,549 A | 9/1975 | Deyerle |
| 3,905,105 A | 9/1975 | Tuke |
| 3,905,374 A | 9/1975 | Winter |
| 3,911,923 A | 10/1975 | Yoon |
| 3,913,585 A | 10/1975 | Wolvek |
| 3,920,022 A | 11/1975 | Pastor |
| 3,941,127 A | 3/1976 | Froning |
| 3,967,625 A | 7/1976 | Yoon |
| 3,989,049 A | 11/1976 | Yoon |
| 3,991,426 A | 11/1976 | Flom et al. |
| 3,994,287 A | 11/1976 | Turp et al. |
| 4,053,953 A | 10/1977 | Flom et al. |
| 4,055,862 A | 11/1977 | Farling |
| 4,081,866 A | 4/1978 | Upshaw et al. |
| 4,085,466 A | 4/1978 | Goodfellow et al. |
| 4,085,743 A | 4/1978 | Yoon |
| 4,103,680 A | 8/1978 | Yoon |
| 4,299,224 A | 11/1981 | Noiles |
| 4,304,178 A | 12/1981 | Haberle |
| 4,311,145 A | 1/1982 | Esty et al. |
| 4,344,193 A | 8/1982 | Kenny |
| 4,349,018 A | 9/1982 | Chambers |
| 4,373,709 A | 2/1983 | Whitt |
| 4,374,523 A | 2/1983 | Yoon |
| 4,385,404 A | 5/1983 | Sully et al. |
| 4,386,609 A | 6/1983 | Mongeon |
| 4,400,833 A | 8/1983 | Kurland |
| D273,895 S | 5/1984 | Kenna |
| D274,091 S | 5/1984 | Kenna |
| 4,453,421 A | 6/1984 | Umano |
| 4,501,269 A | 2/1985 | Bagby |
| 4,509,518 A | 4/1985 | McGarry et al. |
| 4,516,276 A | 5/1985 | Mittelmeier et al. |
| 4,534,365 A | 8/1985 | Bonetta et al. |
| 4,545,375 A | 10/1985 | Cline |
| 4,554,686 A | 11/1985 | Baker |
| 4,562,598 A | 1/1986 | Kranz |
| 4,565,192 A | 1/1986 | Shapiro |
| 4,567,886 A | 2/1986 | Petersen |
| 4,574,794 A | 3/1986 | Cooke et al. |
| 4,619,391 A | 10/1986 | Sharkany et al. |
| 4,624,254 A | 11/1986 | McGarry et al. |
| 4,641,648 A | 2/1987 | Shapiro |
| 4,642,120 A | 2/1987 | Nevo et al. |
| 4,646,729 A | 3/1987 | Kenna et al. |
| 4,662,372 A | 5/1987 | Sharkany et al. |
| 4,678,470 A | 7/1987 | Nashef et al. |
| 4,682,598 A | 7/1987 | Beraha |
| 4,685,460 A | 8/1987 | Thornton |
| 4,703,751 A | 11/1987 | Pohl |
| 4,711,233 A | 12/1987 | Brown |
| 4,718,413 A | 1/1988 | Johnson |
| 4,718,916 A | 1/1988 | Morscher |
| 4,739,751 A | 4/1988 | Sapega et al. |
| 4,794,854 A | 1/1989 | Swaim |
| 4,817,602 A | 4/1989 | Beraha |
| 4,834,757 A | 5/1989 | Brantigan |
| 4,838,891 A | 6/1989 | Branemark et al. |
| 4,863,472 A | 9/1989 | Tormala et al. |
| 4,888,022 A | 12/1989 | Huebsch |
| 4,911,721 A | 3/1990 | Bränemark et al. |
| 4,935,023 A | 6/1990 | Whiteside et al. |
| 4,936,852 A | 6/1990 | Kent et al. |
| 4,950,296 A | 8/1990 | McIntyre |
| 4,952,213 A | 8/1990 | Bowman et al. |
| 4,961,740 A | 10/1990 | Ray et al. |
| 4,961,954 A | 10/1990 | Goldberg et al. |
| 4,964,865 A | 10/1990 | Burkhead et al. |
| 4,979,949 A | 12/1990 | Matsen, III et al. |
| 4,979,957 A | 12/1990 | Hodorek |
| 4,985,031 A | 1/1991 | Buss et al. |
| 4,985,038 A | 1/1991 | Lyell |
| 5,007,912 A | 4/1991 | Albrektsson et al. |
| 5,015,247 A | 5/1991 | Michelson |
| 5,032,132 A | 7/1991 | Matsen, III et al. |
| 5,035,700 A | 7/1991 | Kenna |
| 5,060,678 A | 10/1991 | Bauman et al. |
| 5,061,286 A | 10/1991 | Lyle |
| 5,062,843 A | 11/1991 | Mahony, III |
| 5,073,373 A | 12/1991 | O'Leary et al. |
| 5,082,670 A | 1/1992 | Gage et al. |
| 5,084,050 A | 1/1992 | Draenert |
| 5,092,869 A | 3/1992 | Waldron |
| 5,098,436 A | 3/1992 | Ferrante et al. |
| 5,098,437 A | 3/1992 | Kashuba et al. |
| 5,099,859 A | 3/1992 | Bell |
| 5,100,689 A | 3/1992 | Goldberg et al. |
| 5,101,720 A | 4/1992 | Bianchi |
| 5,108,441 A | 4/1992 | McDowell |
| 5,111,987 A | 5/1992 | Moeinzadeh et al. |
| 5,122,144 A | 6/1992 | Bert et al. |
| 5,123,906 A | 6/1992 | Kelman |
| 5,129,909 A | 7/1992 | Sutherland |
| 5,147,365 A | 9/1992 | Whitlock et al. |
| 5,152,744 A | 10/1992 | Krause et al. |
| 5,152,778 A | 10/1992 | Bales, Jr. et al. |
| 5,154,717 A | 10/1992 | Matsen, III et al. |
| 5,162,506 A | 11/1992 | Hadden |
| 5,163,949 A | 11/1992 | Bonutti |
| 5,170,800 A | 12/1992 | Smith et al. |
| 5,171,243 A | 12/1992 | Kashuba et al. |
| 5,171,244 A | 12/1992 | Caspari et al. |
| 5,171,276 A | 12/1992 | Caspari et al. |
| 5,174,300 A | 12/1992 | Bales et al. |
| 5,176,702 A | 1/1993 | Bales et al. |

(56) References Cited

U.S. PATENT DOCUMENTS

| | | | |
|---|---|---|---|
| 5,178,622 A | 1/1993 | Lehner, II |
| 5,183,053 A | 2/1993 | Yeh et al. |
| 5,183,464 A | 2/1993 | Dubrul et al. |
| 5,186,178 A | 2/1993 | Yeh et al. |
| 5,192,327 A | 3/1993 | Brantigan |
| 5,197,968 A | 3/1993 | Clement |
| 5,197,971 A | 3/1993 | Bonutti |
| 5,197,987 A | 3/1993 | Koch et al. |
| 5,204,106 A | 4/1993 | Schepers et al. |
| 5,207,680 A | 5/1993 | Dietz et al. |
| 5,207,692 A | 5/1993 | Kraus et al. |
| 5,217,463 A | 6/1993 | Mikhail |
| 5,228,459 A | 7/1993 | Caspari et al. |
| 5,234,433 A | 8/1993 | Bert et al. |
| 5,242,448 A | 9/1993 | Pettine et al. |
| 5,258,004 A | 11/1993 | Bales et al. |
| 5,263,498 A | 11/1993 | Caspari et al. |
| 5,263,987 A | 11/1993 | Shah |
| 5,269,785 A | 12/1993 | Bonutti |
| 5,273,524 A | 12/1993 | Fox et al. |
| D343,247 S | 1/1994 | Walen |
| 5,275,166 A | 1/1994 | Vaitekunas et al. |
| 5,275,603 A | 1/1994 | Ferrante et al. |
| 5,282,803 A | 2/1994 | Lackey |
| 5,285,773 A | 2/1994 | Bonutti et al. |
| 5,293,878 A | 3/1994 | Bales et al. |
| 5,295,994 A | 3/1994 | Bonutti |
| 5,304,181 A | 4/1994 | Caspari et al. |
| 5,306,285 A | 4/1994 | Miller et al. |
| 5,308,349 A | 5/1994 | Mikhail |
| 5,314,482 A | 5/1994 | Goodfellow et al. |
| 5,322,505 A | 6/1994 | Krause et al. |
| 5,329,845 A | 7/1994 | Bichel |
| 5,342,367 A | 8/1994 | Ferrante et al. |
| 5,342,368 A | 8/1994 | Petersen |
| 5,344,423 A | 9/1994 | Dietz et al. |
| 5,344,458 A | 9/1994 | Bonutti |
| 5,348,541 A | 9/1994 | Lyell |
| 5,364,401 A | 11/1994 | Ferrante et al. |
| 5,364,402 A | 11/1994 | Mumme et al. |
| 5,368,599 A | 11/1994 | Hirsch et al. |
| 5,379,133 A | 1/1995 | Kirk |
| 5,382,249 A | 1/1995 | Fletcher |
| 5,383,937 A | 1/1995 | Mikhail |
| 5,390,683 A | 2/1995 | Pisharodi |
| 5,395,376 A | 3/1995 | Caspari et al. |
| D358,647 S | 5/1995 | Cohen et al. |
| 5,423,827 A | 6/1995 | Mumme et al. |
| 5,425,355 A | 6/1995 | Kulick |
| 5,425,745 A | 6/1995 | Green et al. |
| 5,443,475 A | 8/1995 | Auerbach et al. |
| 5,445,639 A | 8/1995 | Kuslich et al. |
| 5,445,642 A | 8/1995 | McNulty et al. |
| 5,454,365 A | 10/1995 | Bonutti |
| 5,454,815 A | 10/1995 | Geisser et al. |
| 5,454,816 A | 10/1995 | Ashby |
| 5,456,268 A | 10/1995 | Bonutti |
| 5,472,415 A | 12/1995 | King et al. |
| 5,484,095 A | 1/1996 | Green et al. |
| 5,486,178 A | 1/1996 | Hodge |
| 5,490,854 A | 2/1996 | Fisher et al. |
| 5,497,933 A | 3/1996 | DeFonzo et al. |
| 5,507,763 A | 4/1996 | Petersen et al. |
| 5,514,139 A | 5/1996 | Goldstein et al. |
| 5,514,143 A | 5/1996 | Bonutti et al. |
| 5,520,692 A | 5/1996 | Ferrante |
| 5,520,694 A | 5/1996 | Dance et al. |
| 5,522,897 A | 6/1996 | King et al. |
| 5,540,695 A | 7/1996 | Levy |
| 5,545,222 A | 8/1996 | Bonutti |
| 5,546,720 A | 8/1996 | LaBruzza |
| 5,549,683 A | 8/1996 | Bonutti |
| 5,554,169 A | 9/1996 | Green et al. |
| 5,562,675 A | 10/1996 | McNulty et al. |
| 5,569,163 A | 10/1996 | Francis et al. |
| 5,569,260 A | 10/1996 | Petersen |
| 5,569,261 A | 10/1996 | Marik et al. |
| 5,570,700 A | 11/1996 | Vogeler |
| 5,578,039 A | 11/1996 | Vendrely et al. |
| 5,593,448 A | 1/1997 | Dong |
| 5,597,379 A | 1/1997 | Haines et al. |
| 5,608,052 A | 3/1997 | Zmitek et al. |
| 5,609,603 A | 3/1997 | Linden |
| 5,611,802 A | 3/1997 | Samuelson et al. |
| 5,624,444 A | 4/1997 | Wixon et al. |
| 5,624,463 A | 4/1997 | Stone et al. |
| 5,632,745 A | 5/1997 | Schwartz |
| 5,643,272 A | 7/1997 | Haines et al. |
| 5,649,946 A | 7/1997 | Bramlet |
| 5,649,947 A | 7/1997 | Auerbach et al. |
| 5,653,714 A | 8/1997 | Dietz et al. |
| 5,659,947 A | 8/1997 | Eilers et al. |
| 5,662,656 A | 9/1997 | White |
| 5,662,710 A | 9/1997 | Bonutti |
| 5,667,069 A | 9/1997 | Williams, Jr. |
| 5,667,511 A | 9/1997 | Vendrely et al. |
| 5,667,512 A | 9/1997 | Johnson |
| 5,667,520 A | 9/1997 | Bonutti |
| D385,163 S | 10/1997 | Hutchins et al. |
| 5,681,316 A | 10/1997 | DeOrio et al. |
| 5,683,398 A | 11/1997 | Carls et al. |
| 5,688,279 A | 11/1997 | McNulty et al. |
| 5,688,280 A | 11/1997 | Booth, Jr. et al. |
| 5,694,693 A | 12/1997 | Hutchins et al. |
| 5,702,447 A | 12/1997 | Walch et al. |
| 5,702,475 A | 12/1997 | Zahedi |
| 5,704,941 A | 1/1998 | Jacober et al. |
| 5,707,350 A | 1/1998 | Krause et al. |
| 5,712,543 A | 1/1998 | Sjostrom |
| 5,716,360 A | 2/1998 | Baldwin et al. |
| 5,718,708 A | 2/1998 | Webb |
| 5,720,752 A | 2/1998 | Elliott et al. |
| 5,723,331 A | 3/1998 | Tubo et al. |
| 5,733,292 A | 3/1998 | Gustilo et al. |
| 5,749,876 A | 5/1998 | Duvillier et al. |
| 5,755,731 A | 5/1998 | Grinberg |
| 5,755,791 A | 5/1998 | Whitson et al. |
| 5,755,803 A | 5/1998 | Haines et al. |
| 5,769,855 A | 6/1998 | Bertin et al. |
| 5,769,899 A | 6/1998 | Schwartz et al. |
| 5,772,594 A | 6/1998 | Barrick |
| 5,788,700 A | 8/1998 | Morawa et al. |
| 5,810,827 A | 9/1998 | Haines et al. |
| 5,810,831 A | 9/1998 | D'Antonio |
| 5,817,097 A | 10/1998 | Howard et al. |
| 5,817,109 A | 10/1998 | McGarry et al. |
| 5,842,477 A | 12/1998 | Naughton et al. |
| 5,846,931 A | 12/1998 | Hattersley et al. |
| 5,860,980 A | 1/1999 | Axelson, Jr. et al. |
| 5,860,981 A | 1/1999 | Bertin et al. |
| 5,866,415 A | 2/1999 | Villeneuve |
| 5,871,493 A | 2/1999 | Sjostrom et al. |
| 5,879,354 A | 3/1999 | Haines et al. |
| 5,888,219 A | 3/1999 | Bonutti |
| 5,899,914 A | 5/1999 | Zirps et al. |
| 5,908,424 A | 6/1999 | Bertin et al. |
| 5,911,723 A | 6/1999 | Ashby et al. |
| 5,913,874 A | 6/1999 | Berns et al. |
| 5,916,219 A | 6/1999 | Matsuno et al. |
| 5,921,990 A | 7/1999 | Webb |
| 5,925,049 A | 7/1999 | Gustilo et al. |
| 5,961,499 A | 10/1999 | Bonutti et al. |
| 5,997,566 A | 12/1999 | Tobin |
| 6,007,537 A | 12/1999 | Burkinshaw et al. |
| 6,012,456 A | 1/2000 | Schuerch |
| 6,015,419 A | 1/2000 | Strome et al. |
| 6,019,767 A | 2/2000 | Howell |
| 6,022,350 A | 2/2000 | Ganem |
| 6,024,746 A | 2/2000 | Katz |
| 6,056,754 A | 5/2000 | Haines et al. |
| 6,056,756 A | 5/2000 | Eng et al. |
| 6,059,817 A | 5/2000 | Bonutti et al. |
| 6,059,831 A | 5/2000 | Braslow et al. |
| 6,063,095 A | 5/2000 | Wang et al. |

(56) References Cited

U.S. PATENT DOCUMENTS

| | | |
|---|---|---|
| 6,077,270 A | 6/2000 | Katz |
| 6,077,287 A | 6/2000 | Taylor et al. |
| 6,086,593 A | 7/2000 | Bonutti |
| 6,090,122 A | 7/2000 | Sjostrom et al. |
| 6,096,043 A | 8/2000 | Techiera et al. |
| 6,099,531 A | 8/2000 | Bonutti |
| 6,099,532 A | 8/2000 | Florea |
| 6,102,850 A | 8/2000 | Wang et al. |
| 6,106,529 A | 8/2000 | Techiera |
| 6,118,845 A | 9/2000 | Simon et al. |
| 6,120,509 A | 9/2000 | Wheeler |
| 6,132,472 A | 10/2000 | Bonutti |
| 6,156,070 A | 12/2000 | Incavo et al. |
| 6,159,246 A | 12/2000 | Mendes et al. |
| 6,171,340 B1 | 1/2001 | McDowell |
| 6,174,321 B1 | 1/2001 | Webb |
| 6,185,315 B1 | 2/2001 | Schmucker et al. |
| 6,187,023 B1 | 2/2001 | Bonutti |
| 6,195,158 B1 | 2/2001 | Cadell et al. |
| 6,197,064 B1 | 3/2001 | Haines et al. |
| 6,198,794 B1 | 3/2001 | Peshkin et al. |
| 6,211,976 B1 | 4/2001 | Popovich et al. |
| 6,214,051 B1 | 4/2001 | Badorf et al. |
| 6,228,121 B1 | 5/2001 | Khalili |
| 6,258,127 B1 | 7/2001 | Schmotzer |
| 6,277,136 B1 | 8/2001 | Bonutti |
| 6,290,703 B1 | 9/2001 | Ganem |
| 6,290,704 B1 | 9/2001 | Burkinshaw et al. |
| 6,325,806 B1 | 12/2001 | Fox |
| 6,328,572 B1 | 12/2001 | Higashida et al. |
| 6,338,737 B1 | 1/2002 | Toledano |
| 6,358,266 B1 | 3/2002 | Bonutti |
| 6,361,565 B1 | 3/2002 | Bonutti |
| 6,391,040 B1 | 5/2002 | Christoudias |
| 6,406,495 B1 | 6/2002 | Schoch |
| 6,409,722 B1 | 6/2002 | Hoey et al. |
| 6,423,063 B1 | 7/2002 | Bonutti |
| 6,431,743 B1 | 8/2002 | Mizutani et al. |
| D462,767 S | 9/2002 | Meyer et al. |
| 6,458,135 B1 | 10/2002 | Harwin et al. |
| 6,468,280 B1 | 10/2002 | Saenger et al. |
| 6,468,289 B1 | 10/2002 | Bonutti |
| 6,478,799 B1 | 11/2002 | Williamson |
| 6,482,209 B1 | 11/2002 | Engh et al. |
| 6,500,181 B1 | 12/2002 | Portney |
| 6,503,267 B2 | 1/2003 | Bonutti et al. |
| 6,554,837 B1 | 4/2003 | Hauri et al. |
| 6,554,838 B2 | 4/2003 | McGovern et al. |
| 6,558,391 B2 | 5/2003 | Axelson, Jr. et al. |
| 6,575,982 B1 | 6/2003 | Bonutti |
| 6,602,259 B1 | 8/2003 | Masini |
| 6,620,181 B1 | 9/2003 | Bonutti |
| 6,632,225 B2 | 10/2003 | Sanford et al. |
| 6,635,073 B2 | 10/2003 | Bonutti |
| 6,673,077 B1 | 1/2004 | Katz |
| 6,676,662 B1 | 1/2004 | Bagga et al. |
| 6,695,848 B2 | 2/2004 | Haines |
| 6,702,821 B2 | 3/2004 | Bonutti |
| 6,770,078 B2 | 8/2004 | Bonutti |
| 6,979,299 B2 | 12/2005 | Peabody et al. |
| 7,029,477 B2 | 4/2006 | Grimm |
| 7,172,599 B2 | 2/2007 | Steffensmeier et al. |
| 7,261,719 B1 | 8/2007 | Twomey et al. |
| 7,344,541 B2 | 3/2008 | Haines et al. |
| 7,488,324 B1 | 2/2009 | Metzger et al. |
| 7,641,661 B2 * | 1/2010 | Steffensmeier ...... A61B 17/154 606/88 |
| 7,695,479 B1 | 4/2010 | Metzger |
| 7,695,520 B2 | 4/2010 | Metzger et al. |
| 7,780,672 B2 | 8/2010 | Metzger et al. |
| 7,789,885 B2 | 9/2010 | Metzger |
| 7,837,690 B2 | 11/2010 | Metzger |
| 7,887,542 B2 | 2/2011 | Metzger et al. |
| 8,123,758 B2 | 2/2012 | Metzger et al. |
| 8,518,047 B2 | 8/2013 | Metzger et al. |
| 8,551,100 B2 | 10/2013 | Metzger |
| 8,834,486 B2 | 9/2014 | Metzger et al. |
| 8,870,883 B2 | 10/2014 | Metzger et al. |
| 9,023,053 B2 * | 5/2015 | Metzger ............... A61B 17/155 606/87 |
| 2001/0018589 A1 | 8/2001 | Muller |
| 2001/0034554 A1 | 10/2001 | Pappas |
| 2001/0037155 A1 | 11/2001 | Merchant |
| 2002/0029038 A1 | 3/2002 | Haines |
| 2002/0029045 A1 | 3/2002 | Bonutti |
| 2002/0052606 A1 | 5/2002 | Bonutti |
| 2002/0098304 A1 | 7/2002 | Bailey |
| 2002/0116023 A1 | 8/2002 | Fletcher et al. |
| 2002/0156479 A1 | 10/2002 | Schulzki et al. |
| 2002/0173797 A1 | 11/2002 | Van Zile et al. |
| 2002/0198529 A1 | 12/2002 | Masini |
| 2002/0198531 A1 | 12/2002 | Millard et al. |
| 2003/0028196 A1 | 2/2003 | Bonutti |
| 2003/0060831 A1 | 3/2003 | Bonutti |
| 2003/0100906 A1 | 5/2003 | Rosa et al. |
| 2003/0100907 A1 | 5/2003 | Rosa et al. |
| 2003/0130665 A1 | 7/2003 | Pinczewski et al. |
| 2003/0171757 A1 | 9/2003 | Coon et al. |
| 2003/0212403 A1 | 11/2003 | Swanson |
| 2003/0216741 A1 | 11/2003 | Sanford et al. |
| 2003/0220641 A1 | 11/2003 | Thelen et al. |
| 2003/0225413 A1 | 12/2003 | Sanford et al. |
| 2004/0039395 A1 | 2/2004 | Coon et al. |
| 2004/0039396 A1 | 2/2004 | Couture et al. |
| 2004/0102785 A1 | 5/2004 | Hodorek et al. |
| 2004/0138670 A1 | 7/2004 | Metzger |
| 2004/0220583 A1 | 11/2004 | Pieczynski et al. |
| 2005/0027299 A1 | 2/2005 | Metzger |
| 2005/0049603 A1 | 3/2005 | Calton et al. |
| 2005/0070910 A1 | 3/2005 | Keene |
| 2005/0113840 A1 | 5/2005 | Metzger et al. |
| 2005/0149038 A1 | 7/2005 | Haines et al. |
| 2005/0149040 A1 | 7/2005 | Haines et al. |
| 2005/0149041 A1 | 7/2005 | McGinley et al. |
| 2005/0149042 A1 | 7/2005 | Metzger |
| 2005/0177170 A1 | 8/2005 | Fisher et al. |
| 2006/0095049 A1 | 5/2006 | Zannis et al. |
| 2006/0142774 A1 | 6/2006 | Metzger |
| 2006/0142778 A1 | 6/2006 | Dees |
| 2007/0083209 A1 | 4/2007 | Schenberger et al. |
| 2007/0233140 A1 | 10/2007 | Metzger et al. |
| 2007/0282451 A1 | 12/2007 | Metzger et al. |
| 2009/0149859 A1 | 6/2009 | Metzger et al. |
| 2010/0198224 A1 | 8/2010 | Metzger et al. |
| 2010/0318089 A1 | 12/2010 | Metzger et al. |
| 2011/0130762 A1 | 6/2011 | Metzger et al. |
| 2012/0150189 A1 | 6/2012 | Metzger et al. |
| 2014/0039507 A1 | 2/2014 | Metzger |
| 2014/0156019 A1 | 6/2014 | Metzger et al. |

FOREIGN PATENT DOCUMENTS

| | | |
|---|---|---|
| EP | 0466659 A2 | 1/1992 |
| EP | 0466659 A3 | 3/1992 |
| EP | 0914806 A1 | 5/1999 |
| EP | 1260183 A2 | 11/2002 |
| EP | 0914806 B1 | 1/2004 |
| EP | 1587425 A2 | 10/2005 |
| EP | 1260183 B1 | 10/2007 |
| FR | 1111677 | 3/1956 |
| JP | 47002838 U | 9/1972 |
| JP | 64029266 | 1/1989 |
| JP | 2501806 | 6/1990 |
| JP | 3504337 | 9/1991 |
| JP | 6233775 A | 8/1994 |
| JP | 0301311 | 4/1995 |
| JP | 7178114 A | 7/1995 |
| JP | 2002501806 A | 1/2002 |
| JP | 2003507117 A | 2/2003 |
| JP | 2009160422 A | 7/2009 |
| JP | 4309397 B2 | 8/2009 |
| WO | WO-8804912 A2 | 7/1988 |
| WO | WO-8909028 A1 | 10/1989 |
| WO | WO-9607361 | 3/1996 |

(56) References Cited

FOREIGN PATENT DOCUMENTS

| WO | WO-9729703 A1 | 8/1997 |
|---|---|---|
| WO | WO-9939637 A1 | 8/1999 |
| WO | WO-0113802 A1 | 3/2001 |
| WO | WO-2004064621 A2 | 8/2004 |
| WO | WO-2004064621 A3 | 8/2004 |
| WO | WO-2005046432 A2 | 5/2005 |

OTHER PUBLICATIONS

"U.S. Appl. No. 14/047,361, Non Final Office Action mailed Sep. 17, 2014", 6 pgs.
"U.S. Appl. No. 14/047,361, Notice of Allowance mailed Jan. 6, 2015", 5 pgs.
"U.S. Appl. No. 14/047,361, Response filed Dec. 17, 2014 to Non Final Office Action mailed Sep. 17, 2014", 12 pgs.
"European Application Serial No. 04702213.2, Communication Pursuant to Article 94(3) EPC mailed Apr. 29, 2014", 4 pgs.
"European Application Serial No. 04702213.2, Communication Pursuant to Article 94(3) EPC mailed May 21, 2012", 4 pgs.
"European Application Serial No. 04702213.2, Communication Pursuant to Article 94(3) EPC mailed Jun. 6, 2011", 4 pgs.
"European Application Serial No. 04702213.2, Communication Pursuant to Article 94(3) EPC mailed Jun. 10, 2013", 4 pgs.
"European Application Serial No. 04702213.2, Communication Pursuant to Article 94(3) EPC mailed Sep. 21, 2010", 8 pgs.
"European Application Serial No. 04702213.2, Decision to grant mailed Aug. 6, 2015", 2 pgs.
"European Application Serial No. 04702213.2, Intention to grant mailed Mar. 23, 2015", 34 pgs.
"European Application Serial No. 04702213.2, Response filed Jan. 27, 2011 to Communication Pursuant to Article 94(3) EPC mailed Sep. 21, 2010", 14 pgs.
"European Application Serial No. 04702213.2, Response filed Oct. 5, 2011 to Communication Pursuant to Article 94(3) EPC mailed Jun. 6, 2011", 18 pgs.
"European Application Serial No. 04702213.2, Response filed Oct. 29, 2014 to Communication Pursuant to Article 94(3) EPC mailed Apr. 29, 2014", 11 pgs.
"European Application Serial No. 04702213.2, Response filed Nov. 14, 2013 to Communication Pursuant to Article 94(3) EPC mailed Jun. 10, 2013", 11 pgs.
"European Application Serial No. 04702213.2, Response filed Nov. 30, 2012 to Communication Pursuant to Article 94(3) EPC mailed May 21, 2012", 8 pgs.
"European Application Serial No. 04702213.2, Supplemental European Search Report mailed Apr. 23, 2010", 6 pgs.
"AGC 3000 Intramedullary Surgical Technique Using PMMA Fixation," 1987, Biomet, Inc.
"AGC Distal Fem Cutter for Dr. Hardy," Biomet, Inc., Jun. 22, 1989.
"AGC Total Knee System, Intramedullary Without Distractor Surgical Technique," 1989, Biomet, Inc.
"AGC Traditional Surgical Overview", copyright 2001 Biomet Orthopedics, Inc.
"AGC-S Total Knee System, Surgical Technique for the AGC-S Total Knee System," 1992, Biomet, Inc.
"Anatomic Axial Alignment Instrumentation," 1994, Biomet, Inc.
"Hand Instruments", High Performance, Precision Series brochure by Arthrotek, copyright 2000.
"NexGen® Complete Knee Solution MIS Quad-Sparing™ Instrumentation," (Mar. 17, 2006) Zimmer, Inc. Web. Jul. 21, 2010. http://www.zimmer.com/ctl?pcrat=M3&prod=y&template=MP&action=1&op=global&id . . . 2 pages.
"pfcSigma.RP-F, High Function Demands Rotation," brochure. (2006) DePuy Orthopaedics, Inc. 2 pages.
"Rotating Platform Knee Technology," tri-fold brochure. (2007) DePuy Orthopaedics, Inc. 2 pages.
"Rotating Platform: Proven," brochure. (2007) DePuy Orthopaedics, Inc. 2 pages.
"Rotating Platform: Unique," brochure. (2007) DePuy Orthopaedics, Inc. 2 pages.
"Sigma High Performance Partial Knee, Unicondylar Surgical Technique," brochure. (2008) DuPuy Orthopaedics, Inc. pp. 1-33.
"Sigma HP Partial Knee," product information sheet. (Feb. 4, 2009).
"SIGMA® High Performance Instruments, A high performance knee system demands high performance instruments," advertisement. (2007) DePuy Orthopaedics, Inc. 1 page.
"SIGMA® High Performance Instruments, Balanced Surgical Technique," brochure. (2008) DePuy Orthopaedics, Inc. pp. 1-49.
"SIGMA® High Performance Instruments, Measured Resection Classic Surgical Technique," brochure. (2008) DePuy Orthopaedics, Inc. pp. 1-48.
"SIGMA® High Performance Instruments, Measured Resection Fixed Reference Surgical Technique, Featuring the mini-subvastus approach," brochure. (2007) DePuy Orthopaedics, Inc. pp. 48.
"SIGMA® High Performance Instruments, Product Rationale," brochure. (2007) Depuy Orthopaedics, Inc. 12 pages.
"The AGC Revision Knee System Surgical Technique," 1997 Biomet, Inc.
"The Freeman Samuelson Total Knee System," brochure, Biomet, Inc. (1994) 4 pages.
"The Sigma® High Performance Partial Knee: Potential to move more naturally," tri-fold brochure. (2009) DuPuy Orthopaedics, Inc. 2 pages.
"Total Knee Replacement," brochure. (2004) DePuy Orthopaedics, Inc. pp. 1-16.
"What Really Matters," brochure. (2006) DePuy Orthopaedics, Inc. 6 pages.
"Your New Rotating Platform Knee," tri-fold brochure. (2007) DePuy Orthopaedics, Inc. 2 pages.
AGC Total Knee System, Unicondylar Surgical Overview, Biomet, Inc. (5 pages) Jan. 1989.
European Patent Office Action mailed Jun. 6, 2011 for EP Application No. 04702213.2 claiming benefit of PCT/US2004000953, which claims benefit of U.S. Appl. No. 10/345,102, filed Jan. 15, 2003.
European Patent Office Action mailed May 21, 2012 for EP Application No. 04702213.2 claiming benefit of PCT/US2004000953, which claims benefit of U.S. Appl. No. 10/345,102, filed Jan. 15, 2003.
European Patent Office Action mailed Sep. 21, 2010 for EP Application No. 04702213.2 claiming benefit of PCT/US2004000953, which claims benefit of U.S. Appl. No. 10/345,102, filed Jan. 15, 2003.
European Patent Office Supplementary Search Report mailed Apr. 23, 2010 for PCT/US2004000953, claiming benefit of U.S. Appl. No. 10/345,102, filed Jan. 15, 2003.
Genus, brochure entitled "Uni Knee System," Biomet, Inc., Nov. 15, 1998.
Insall/Burstein II Modular Knee System by Zimmer, Inc. 20 pages, 1989.
International Search Report and Written Opinion mailed Jun. 3, 2005 for PCT/US04/00953 claiming benefit of U.S. Appl. No. 10/345,102, filed Jan. 15, 2003.
Japanese Office Action mailed Aug. 2, 2011 for JP Application No. 2009-057755 filed Mar. 11, 2009, claiming benefit of JP Serial No. 2005-518807 filed Jan. 14, 2004; which claims benefit of PCT/US2004/000953 filed Jan. 14, 2004; which claims benefit of U.S. Appl. No. 10/345,102, filed Jan. 15, 2003.
Japanese Office Action mailed Nov. 11, 2008 for JP Application No. 2005-518807 filed Jul. 15, 2005, which claims benefit of PCT/US2004/000953 filed Jan. 14, 2004; which claims benefit of U.S. Appl. No. 10/345,102, filed Jan. 15, 2003.
Keys, Graham W., "Reduced Invasive Approach for Oxford II Medial Unicompartmental Knee Replacement—a Preliminary Study," The Knee, (1999) pp. 193-196.
McGinty, M.D., Operative Arthroscopy, Department of Orthopaedic Surgery, Medical University of South Carolina, Charleston, South Carolina, copyright 1991 by Raven Press, Ltd., (2 pages).
MIS Minimally Invasive Solution—The M/G Unicompartmental Knee by Zimmer, 4 sheets.

(56) References Cited

OTHER PUBLICATIONS

MIS Minimally Invasive Solution the M/G Unicompartmental Knee Minimally Invasive Surgical Technique, by Zimmer, copyright 2000 (pp. 1-27).

Nex Gen Complete Knee Solution—Intramedually Instrumentation Surgical Technique—For the NexGen Cruciate Retaining & Legacy Posterior Stablized Knee—Publication 1994.

NexGen Complete Knee Solution—Extramedullary/Intramedullary Tibial Resector Surgical Technique—2008.

NexGen Complete Knee Solution—Multi-Reference 4-in-1 Femoral Instrumentation-Anterior Reference Surgical Technique—Publication date unknown, but before Aug. 1, 2001.

NexGen Complete Knee Solution—Surgical Technique for the LPS-Flex Fixed Bearing Knee, 2000.

Orthopaedic Update, No. 18, The Fudger™—The Ultimate Weapon in the Femoral Referencing War, Biomet, Inc. (2 pages).

Scorpio! Single Axis Total Knee System—Passport Total Knee Instruments—Passport A.R. Surgical Technique by Sryker Howmedica Osteonics, 2000.

Simple Instruments Surgical Technique for the Knee, copyright 2000 Biomet, Inc.

Surgical Navigation for Total Knee Arthroplasty—Believed to have been presented at the American Academy of Orthopedic Surgeons in Feb. 2001.

The Oxford, brochure entitled "Unicompartmental Knee System", Biomet Orthopedics, Inc., Jul. 15, 2004.

"NexGen System Complete Knee Solution—Design Rationale", (date unknown), 26 pgs.

"Surgical Technique for the Maxim®, Ascent™ and Vanguard™ Total Knee Systems", Microplasty™ minimally invasive knee instruments brochure, (Feb. 29, 2004), 15 pgs.

\* cited by examiner

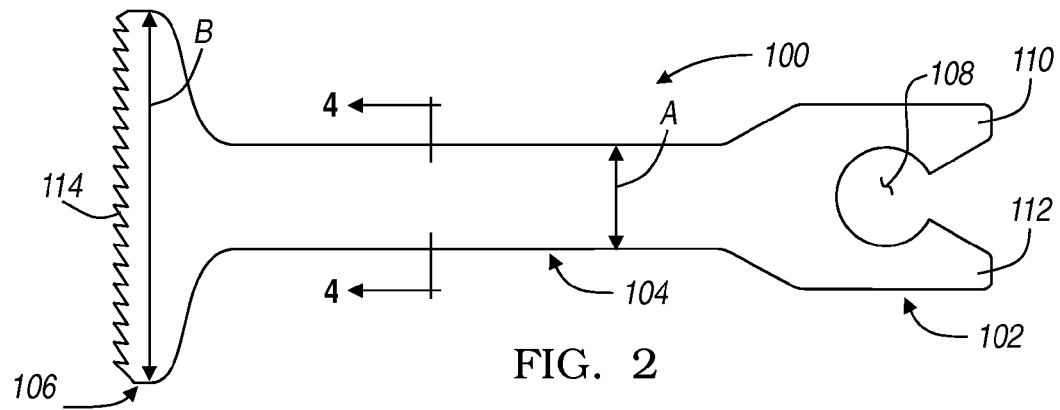
FIG. 2
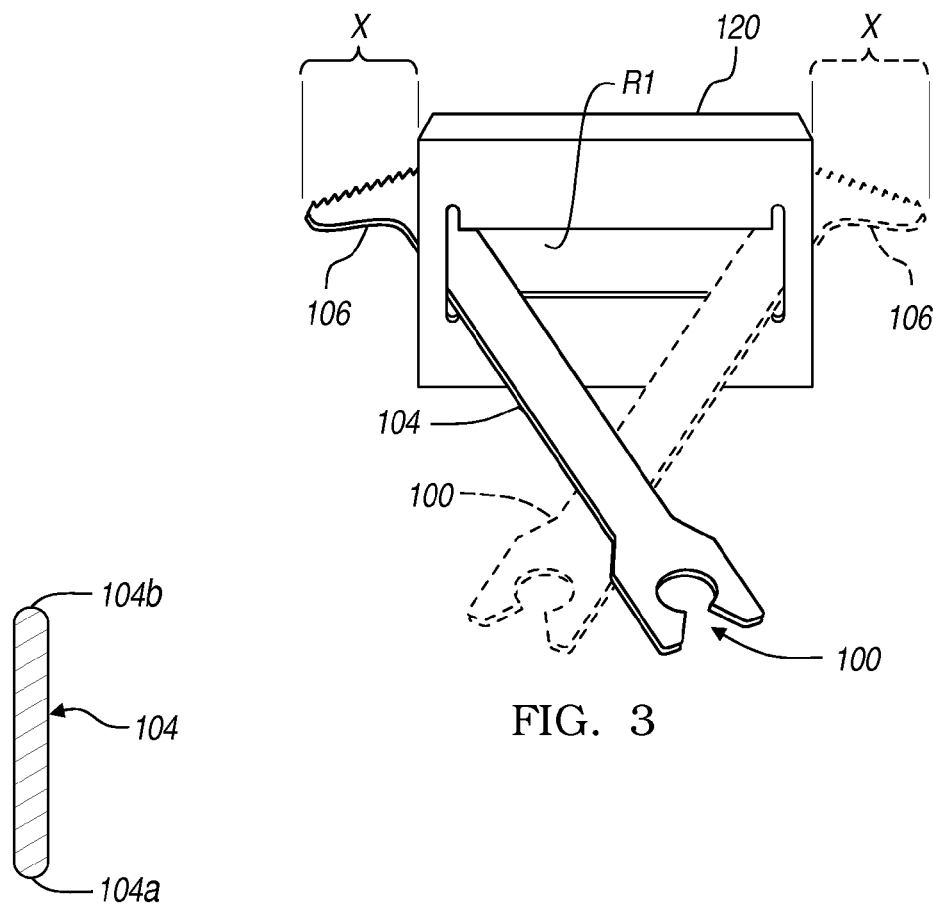
FIG. 3
FIG. 4

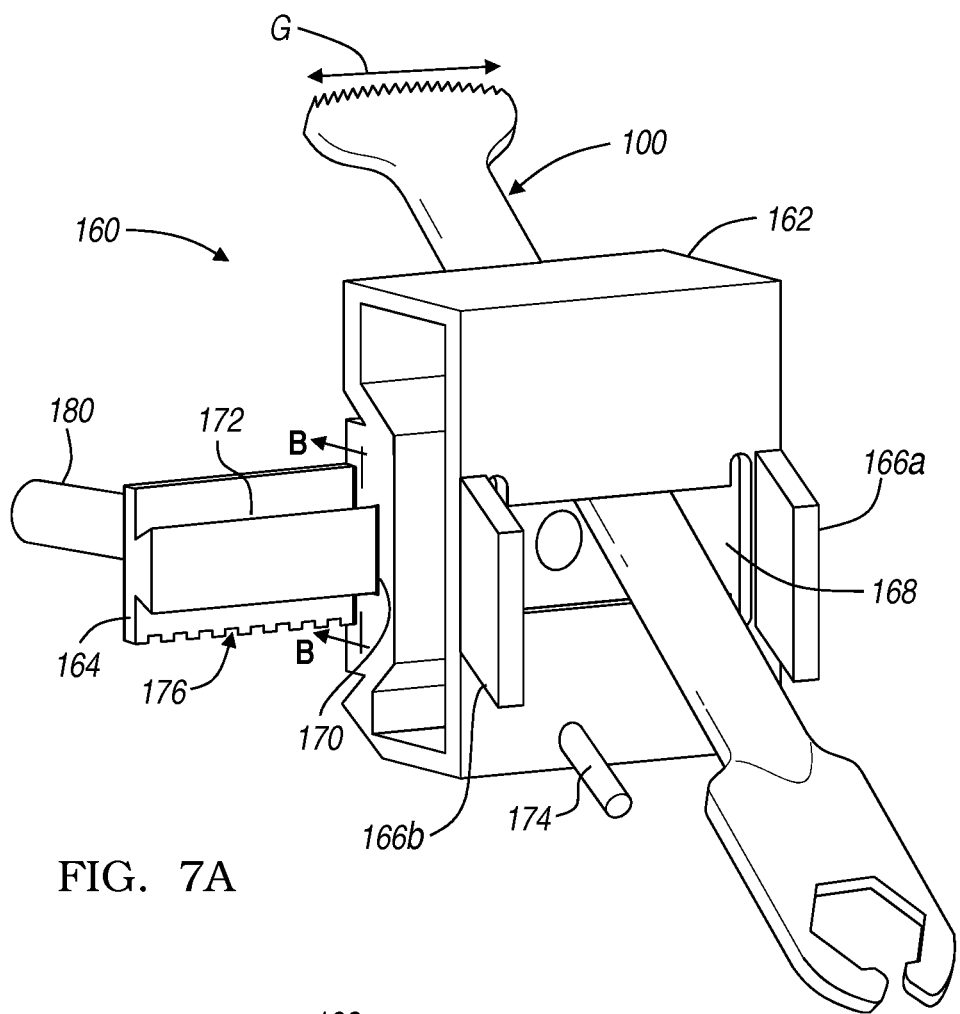
FIG. 7A
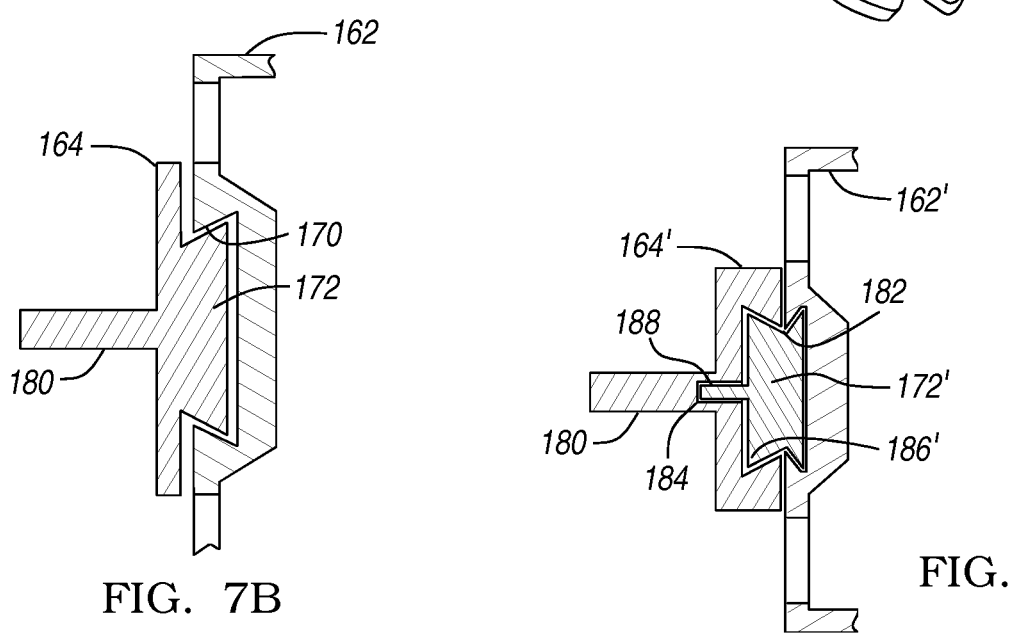
FIG. 7B
FIG. 8

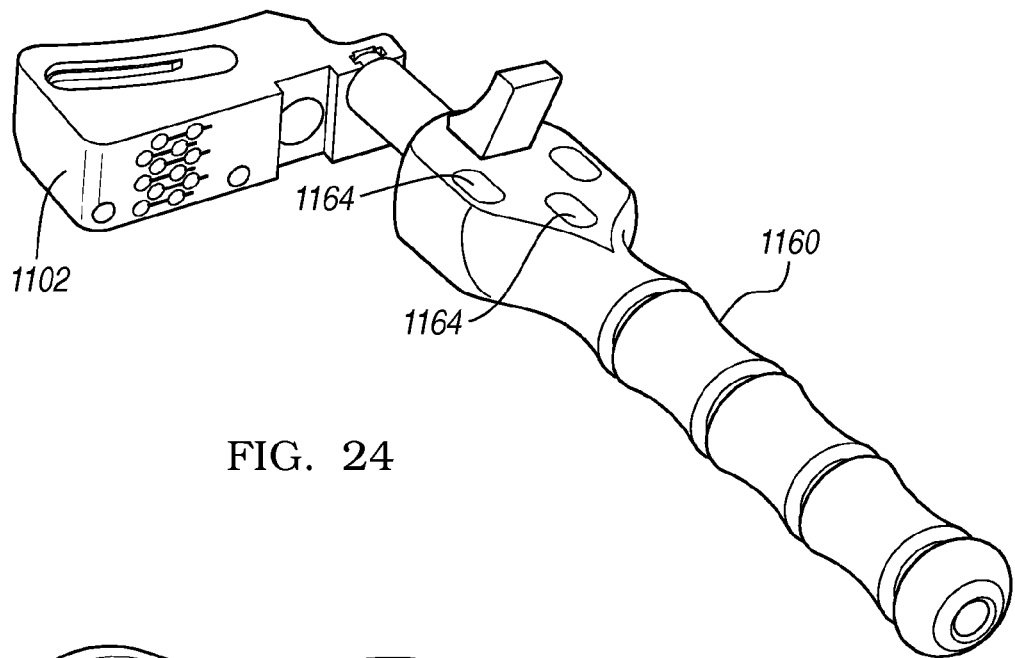
FIG. 24
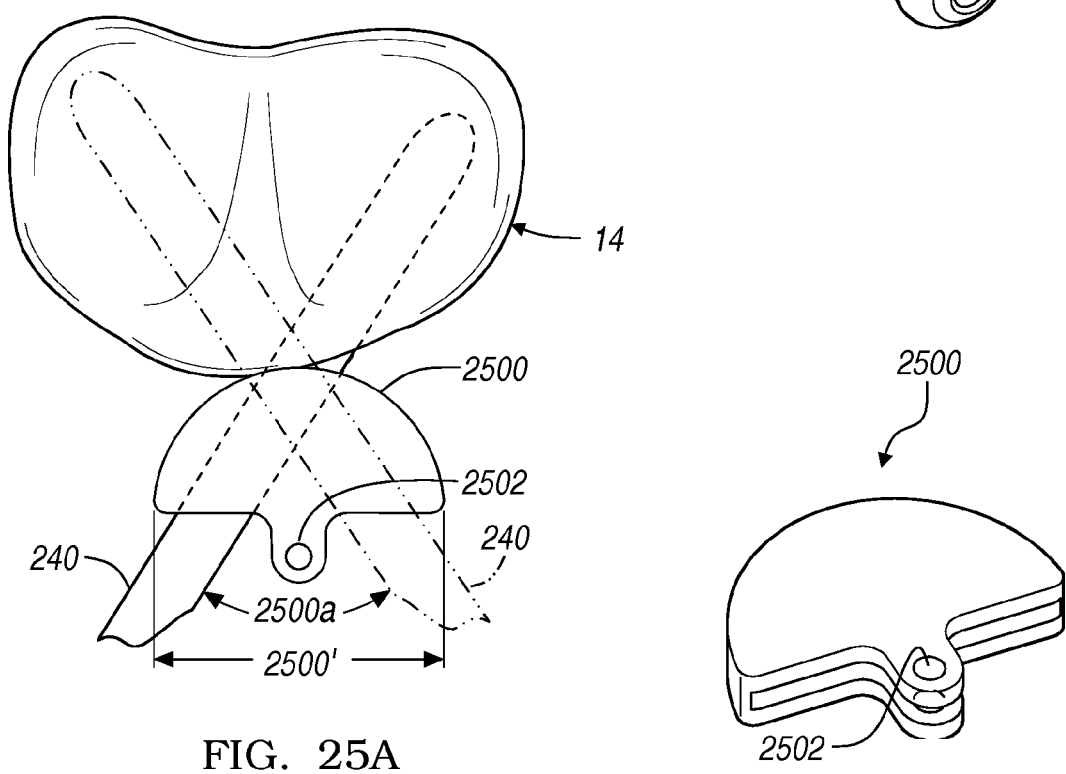
FIG. 25A
FIG. 25B

INSTRUMENTATION FOR KNEE RESECTION

CROSS-REFERENCE TO RELATED APPLICATIONS

This application is a continuation patent application of U.S. patent application Ser. No. 14/047,361 filed on Oct. 7, 2013, which is scheduled to issue as U.S. Pat. No. 9,023,053 on May 5, 2015 and is a divisional patent application of U.S. patent application Ser. No. 11/337,861 filed on Jan. 23, 2006, which issued as U.S. Pat. No. 8,551,100 on Oct. 8, 2013 and is a continuation-in-part of U.S. patent application Ser. No. 11/058,527 filed on Feb. 15, 2005, which issued as U.S. Pat. No. 7,789,885 on Sep. 7, 2010 and is a continuation-in-part of U.S. patent application Ser. No. 10/931,220 filed on Aug. 31, 2004, which issued as U.S. Pat. No. 7,887,542 on Feb. 15, 2011 and is a continuation-in-part of U.S. patent application Ser. No. 10/345,102 filed on Jan. 15, 2003, which issued as U.S. Pat. No. 7,837,690 on Nov. 23, 2010. The disclosures of the above applications are incorporated herein by reference.

FIELD

The present teachings relate to orthopedic surgery, and particularly to, knee resection procedures and instruments.

INTRODUCTION

The human anatomy includes many articulating portions. For example, the femur and the tibia form a knee joint in the human anatomy. The femur and tibia articulate relative to one another during many activities, such as walking or kneeling. Nevertheless, over time, disease and/or injury can deteriorate the knee joint, such that articulation of the joint becomes painful or impractical. When such injuries occur, anatomical replacements, particularly prosthetics, can be placed in the femur, tibia, or both. The prosthetics may replace the articulating portions and allow a substantially natural articulation of the joint. Replacing the damaged portions allow for a much easier and more practical articulation of the knee joint to assist the individual in returning to a more natural lifestyle.

To replace joints, such as the knee joint, the original or natural anatomy, including boney portions, must first be removed or resected. For example, the knee joint includes the condyles of the femur and the tibial plateau. The condyles of the femur articulate with a meniscus in the knee joint, which is supported by the tibia. To replace the knee joint, particularly replacing the articulating portions, the tibial plateau and the condyles of the femur are generally removed.

Often, the condyles of the femur are removed with a saw blade or other reaming devices. The femur is shaped to receive the prosthetic, which will simulate the condyles of the femur after implantation. Specifically, the femur must be shaped to substantially compliment the superior portion of the femoral implant to ensure a substantially tight and secure fit between the femoral implant and the femur.

Likewise, the tibia must be resected to properly receive the tibial implant. This often requires removing the superior portion of the tibia so that an implant can be securely fixed to the superior portion of the resected tibia. A saw blade or other reaming device is used to remove the superior portion and substantially flatten the superior portion of the tibia. After this, a tibial implant can be implanted onto the tibia and securely fixed in place.

To perform such knee replacements, and other joint replacements, it may be desirable to allow a less invasive procedure. During less invasive surgeries, the incision to insert the tools may be kept to a minimum, should a surgeon desire. Likewise, the tools and instruments used to perform the procedure are optimized to provide minimal abrasion and trauma to the surrounding soft tissue. Therefore, it may be desirable to provide instruments that can be used through very small incisions to decrease the amount of trauma to the soft tissue. Similarly, the ease of use of the smaller instruments may be desired to be enhanced to allow for an efficient and proper use during the surgical procedure.

In total knee joint replacement procedures, the proximal end of the tibia is generally resected at a desired angle to define a tibial resection plateau for receiving a tibial implant. Devices for performing the tibial resection generally include a cutting block which guides a saw blade.

SUMMARY

Devices and methods that may be used during a minimally invasive surgery for a joint resection include a saw blade and cutting block. The saw blade that may be used use in a minimally invasive surgery includes a narrowed neck or body to allow for an ease of use through a small incision. The head, which include cutting teeth, can be broader than the neck of the saw blade. The narrowed neck allows the blade to translate in a small incision, without abrading the soft tissue. A second saw blade may include an angled neck. The angled neck may also be narrowed relative to the cutting head, but the angled neck allows the cutting head to be laterally offset from the power tool. Therefore, all portions of a joint, such as the knee joint, can be reached from a single incision, which is placed medially or laterally on the knee. In conjunction with the above-described saw blades and other generally known saw blades, a cutting block, which is able to translate medially and laterally is also described. Specifically, a cutting block can be mounted to the inferior portion of the femur and used as a cutting guide during the resection procedure. The cutting block may be moved medially/laterally, along with the incision and soft tissue, such that the cutting guide or cutting block need not be repositioned other than being slid along a rail.

According to various embodiments a guide block assembly for assisting in resecting a boney structure is disclosed. The assembly comprises a track member having a fixation section to fix the track member to the boney structure and a track translation section. The assembly also includes a cutting block having a guiding section adapted to guide a cutting member and a guide translation section to operably engage the track translation section. The track translation section and the guide translation section operably interact to allow the cutting block to translate relative to the track member. This allows the cutting block to be selectively positionable in more than one position while the track member remains in a single position.

According to various embodiments a saw blade for resecting a portion of an anatomy is disclosed. The saw blade comprises a first end having a tool engaging section extending along a first longitudinal axis. The saw blade further comprises a second end having a cutting head defining a plurality of cutting teeth, and extending along a second longitudinal axis. A neck portion interconnects the cutting head and the tool engaging section. The first and second longitudinal axes intersecting at the neck portion. The first axis and the second axis are disposed such that the cutting head is laterally offset from the tool engaging section.

According to various embodiments a kit for resecting a portion of an anatomy is disclosed. The kit comprises at least one saw blade including a cutting head and a neck portion and a guide block assembly including a track member and a cutting block. The track member includes a fixation section to fix the track member to a structure and a track translation section. The cutting block includes a guiding section adapted to guide a member and a guide translation section to operably engage the track translation section. The track translation section and the guide translation section operably engage to allow the cutting block to translate relative to the track member.

According to various embodiments a method for resecting a boney portion of an anatomy that is surrounded by soft tissue is disclosed. The method comprises creating an incision in the soft tissue surrounding the boney portion. A saw blade is selected to resect a first portion of the boney portion. A guide rail is mounted in a first rail position relative the boney portion. A cutting block is positioned in a first cutting block position relative to the guide rail to guide the saw blade. The cutting block is moved to a second cutting block position relative to the guide rail, such that the cutting block guides the saw blade in the second cutting guide position while the guide rail remains in the first rail position.

According to various embodiment an instrument for guiding a tool relative to a portion of an anatomy is disclosed. The instrumentation may include a track member and a translating member associated with the track member to translate relative to the track member. Also, a positioning member may be provided that is operable to associate at least one of the track member or the translating member relative to the anatomy. The track member is operable to be fixed to the anatomy in an associated position.

According to various embodiments instrumentation for guiding a tool relative to a selected portion of an anatomy is disclosed. The instrumentation may include a track member operable to be fixed to the anatomy having a first length between a first end and a second end and a guide member including a second length between a first guide end and a second guide end. A guide surface may be defined by at least a portion of the guide member. The first length and the second length are less than a dimension of the anatomy to be affected by the tool.

According to various embodiments a method of guiding a tool relative to a portion of an anatomy with a moving guide member is disclosed. The method may include positioning a track member relative to the anatomy and positioning the guide member relative to the anatomy with the track member in a first position. A tool may be guided relative to the anatomy with the guide member in the first position and the guide member may be moved to a second position. The tool my also be guided relative to the anatomy in the second position.

The present teachings may also provide an apparatus for performing a tibial resection in a minimally or less invasive resection procedure or in a conventional open procedure. The methods and apparatuses of the present teachings may allow for a resection to occur through a small incision and generally minimally invasively. For example, the apparatus may be positioned for resecting a tibia through a generally small incision and with minimal impact on associated soft tissue. The apparatus includes a support block attachable to a tibia or other appropriate portion, a cutting guide defining a saw blade or guide slot, and an engagement device coupling the cutting guide to the support block such that the cutting guide can move relative to the support block such as by rotating and/or along an angled arcuate path.

The present teachings also provide a modular sizing device for a bone. The sizing device includes a sizer base positionable relative to the bone, a stylus, and a coupler operable to magnetically couple the base to the stylus for measuring a size of the bone.

The present teachings further provide a modular cutting device for a bone. The cutting device includes a cutting block having a cutting slot, an alignment guide removably couplable to the cutting block, and a drill guide slidably couplable to the cutting block.

The present teachings further provide a kit of surgical components for femoral sizing. The kit includes a stylus, a sizer base including an extension for receiving a fastener, a coupler for coupling the sizer base to the stylus, a magnet receivable in a cavity of the coupler for magnetic attachment to the stylus, and a spring-loaded handle for engaging the fastener.

The present teachings may also provide a tibial resection apparatus that includes a support block attachable to tibia and a cutting guide defining a saw blade slot. The support block has a superior surface defining an angled arcuate groove, and the cutting guide has a peg receivable in the arcuate groove, such that the cutting guide can slide along the groove and rotate about the peg relative to the support block.

The present teachings provide for a system for performing a resection of a selected portion of an anatomy with a resection instrument. The system includes a first member, a first movement defining portion defined by the first member, a second member, and a second movement defining portion of the second member. The first member is fixable to the selected portion of the anatomy. The second member is configured to cooperate with the first member. The first movement defining portion and the second movement defining portion are operable to allow the second member to be moveable relative to the first member from a first position to a second position. The resection instrument is positionable relative to the second member in the first position and in the second position to form a selected resection of the selected portion of the anatomy.

The present teachings further provide for a system for resecting a proximal tibial portion with a resection instrument. The system includes a main guide portion, a first dynamic connection portion included with the main guide portion, a dynamic guide member, a guide surface, and a second dynamic connection portion. The guide surface is defined by the dynamic guide member and is configured to guide the resection instrument during resection of the proximal tibial portion. The second dynamic connection portion is included with the dynamic guide member. The first and the second dynamic connection portions are configured to cooperate with one another to guide movement of the dynamic guide member and the guide surface.

The present teachings also provide for a method for resecting a proximal portion of a tibia. The method includes fixing a main guide portion including a first dynamic connection portion to the tibia; coupling a dynamic guide member to the main guide portion through cooperation between the first dynamic connection portion and a second dynamic connection portion of the dynamic guide member; guiding a resection instrument to the tibia with a guide surface of the dynamic guide member; and sliding and rotating the dynamic guide member to guide the resection instrument to various portions of the tibia.

Further areas of applicability will become apparent from the detailed description provided hereinafter. It should be understood that the detailed description and specific examples, while indicating various embodiment of the invention, are intended for purposes of illustration only and are not intended to limit the scope of the following claims.

BRIEF DESCRIPTION OF THE DRAWINGS

The present description will become more fully understood from the detailed description and the accompanying drawings, wherein:

FIG. 2 is a plan view of a narrow saw blade according to one embodiment;

FIG. 3 is a perspective view of the saw blade in conjunction with a guide or cutting block;

FIG. 4 is a cross-sectional view of the saw blade taken along line 4-4;

FIG. 7A is a perspective view of a cutting block assembly with a saw blade disposed therethrough;

FIG. 7B is a cross-section taken along the line B-B of FIG. 7A;

FIG. 8 is a cross-sectional view of a rail assembly according to an alternative embodiment;

FIG. 24 is an isometric view of a support block attached to an alignment handle according to the present teachings; and FIG. 25A is a plan view of a rotating guide according to various embodiments;

FIG. 25B is a perspective view of the guide of FIG. 25A;

DETAILED DESCRIPTION OF VARIOUS EMBODIMENTS

The following description of various embodiments is merely exemplary in nature and is in no way intended to limit the appended claims, its application, or uses. Although the following various embodiments are illustrated in use with a knee joint and/or minimally invasive surgery, it will be understood that the apparatuses and methods described herein can be used in conjunction with any other joint on any surgical procedure. For example, the saw blades and the cutting block may be used to resect the shoulder, elbow, or other joints in the anatomy. Therefore, the following description relating to a knee joint is merely exemplary and not intended to limit the scope of the following claims.

Figure 1:
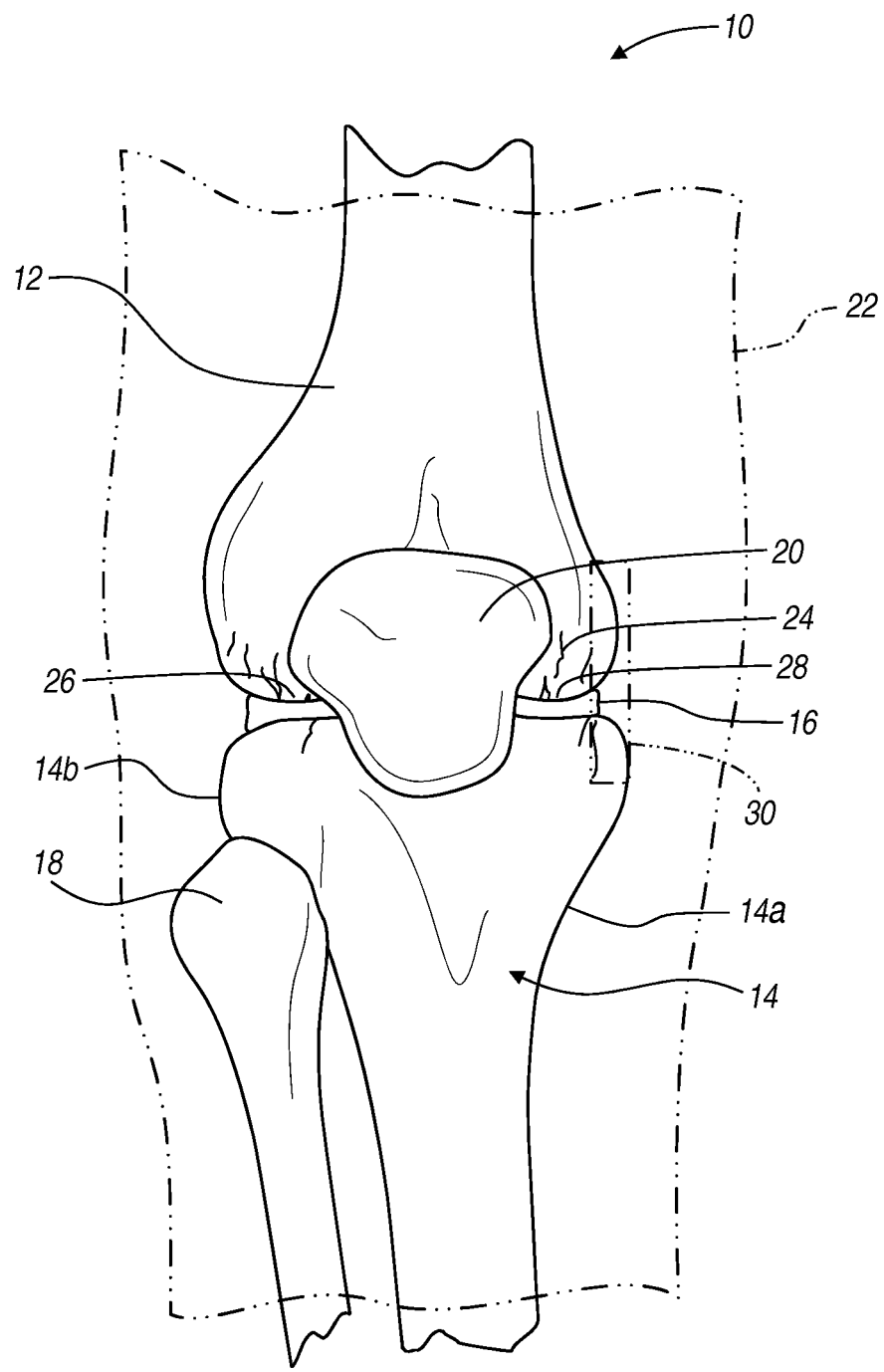
FIG. 1 is an anterior view of a right knee of a human anatomy.

With reference to FIG. 1, a knee joint 10 (illustrated as a right leg) of a human anatomy includes a femur 12 that can articulate with a tibia 14. The tibia 14 of the right leg includes a medial side 14a and a lateral side 14b. Disposed between the femur 12 and the tibia 14 is a meniscus 16, which cushions the articulation and provides a bearing between the two boney portions or structures. The knee joint 10 further includes a fibula 18 and a patella 20. Surrounding the knee joint 10 is a soft tissue 22, which includes muscle, adipose tissue, and the epidermis. To perform any procedures on the internal components of the knee joint 10, the soft tissue 22 must be pierced. The femur 12 includes a first condyle 26 and a second condyle 28. It will be understood that the first condyle 26 may be a lateral condyle when the knee is a right knee, such as the knee illustrated in FIG. 1. It will be understood that the following discussion and instruments may also applicable, with minor changes, if any, to a left knee as well.

The knee joint 10 may become damaged or injured such that small fractures 24 or other injuries or deteriorations occur. When such injuries become great enough, the knee joint 10 may be resected and a prosthetic implanted to replace the articulating portions. The first and second condyles 26, 28 define an inferior surface of the femur 12. Moreover, the femur 12 is generally rounded and includes arcs and rounded surfaces of the first and second condyles 26, 28 on the inferior side of the femur 12. These convex surfaces provide for easy articulation of the femur 12 with the tibia 14. Similarly, convex surfaces are defined by the femur 12 on the anterior 12b and posterior 12c (shown in FIG. 10B) sides as well. However, to implant a prosthetic, it is generally easier and more efficient to mount the prosthetic to substantially planar surfaces. Therefore, the convex surfaces of the femur 12 are resected before implanting a prosthetic. To provide such a resection, an incision 30 is made through the soft tissue 22 to gain access to the knee joint 10 (in FIG. 10B). Though various styles and methods of making the incision 30 are known, however a surgeon may find it desirable to provide a less invasive incision 30. Therefore, the incision 30 is generally between about 1 cm and about 10 cm in length to provide access to the knee.

Because the incision 30 is made through the soft tissue 22, the incision 30 may be a small size and moved relative to the femur 12 and the tibia 14 to perform the procedure. Nevertheless, the smaller incision 30, the less trauma provided to the soft tissue 22. Because of the small incision 30, the instruments provided to resect the knee joint 10 are designed to efficiently perform their tasks without further traumatizing the soft tissue 22 and able to fit through the incision 30.

With reference to FIG. 2, a saw blade 100 for resecting a portion of the knee joint 10 is illustrated. The saw blade 100 may be used to resect the inferior portion of the femur 12, including the first and second condyles 26, 28 or the superior portion of the tibia 14. The saw blade 100 includes a tool engaging end or section 102, a body or neck 104, and a cutting head 106. The tool engaging end 102 includes a tool receiving notch 108, which is defined by a first leg 110 and a second leg 112. In this way, a portion of a power tool (not illustrated, but generally known) can be received within the tool receiving notch 108 to operate the saw 100 within the knee joint 10. It will be understood that any appropriate means or design may be used to affix the saw blade 100 to any appropriate tool. The tool engaging notch 108 is simply exemplary of any numerous method, which may be used to properly affix the saw blade 100 to a power tool. Other exemplary methods include a compression fit with a set screw or a bore formed in the saw blade 100, which would receive a set screw, but not include a notch. Therefore, the illustration of the exemplary tool engaging notch 108 is not intended to limit the present disclosure or the following claims. Furthermore, the tool engaging end 102 may be any appropriate size, including any appropriate width or depth to be properly received within a power tool. For example, the power tool may require that the tool engaging end 102 of the saw blade 100 be at least 1.5 cm in width. Therefore, the tool engaging end 102 may be at least 1.5 cm in width.

The neck 104 of the saw blade 100 has a width A which is selected to be narrower than a width B of the cutting head 106. Although width A of the saw blade 100 can be any appropriate width, it is generally selected to be relatively small to lessen abrasion and trauma to the soft tissue 22 defining the incision 30. This design also increases utility of a cutting guide as described more fully herein.

With continuing reference to FIG. 2 and additional reference to FIG. 3, the width A of the neck 104 also allows a greater area to be resected by the saw blade 100. Specifically, as illustrated in FIG. 3, the narrow width A of the neck 104 allows the cutting head 106 to resect an area which is beyond the width of a cutting block 120. Because of the narrow width A of the neck 104, the cutting head 106 is able to easily resect an area at least a distance X beyond the edge of the slot 121 defined by the cutting block 120. The slot 121 defines a guide area of the cutting block 120. A saw blade including a neck and cutting head of equal widths limits the amount of area that a user is able to resect outside of the width of the slot 121. The narrow neck 104, however, allows the distance X to be resected outside of the width of the slot 121. The saw blade 100 is able to resect the distance X on both sides of the cutting block 120 during use.

Even though the neck 104 may have a selected width A, the cutting head 106 may have a different selected width B. Defined on the distal end of the saw blade 100 are cutting teeth 114. The cutting teeth 114 move in conjunction with the cutting head 106 and provide a sawing action to saw and remove material that is to be resected. The cutting teeth 114 may be any appropriate design or shape to provide the desired resection, speed or efficiency. Nevertheless, the width B of the cutting head 106 may be selected to allow for a greater cutting width than the width of the neck A. Although, the width A of the neck 104 may be selected to be smaller than the width of the retracted incision 30, the width B of the cutting head 106 may be selected to be greater than the width of the incision 30. For example, the width B of the cutting head 106 may be at least twice as big of the width A of the neck 104. This provides a cutting area, which is greater than the width of the neck 104, while minimizing trauma to the soft tissue 22.

With continuing reference to FIG. 2, and additional reference to FIG. 4, the neck 104 of the saw blade 100 includes a first side 104a and a second side 104b. The edges or sides 104a and 104b of the neck 104 may include convex or other smooth non-angular shapes. The smooth and non-angular shapes further minimize trauma to the soft tissue 22 during operation. Simply, the saw 100 vibrates back and forth to move the cutting teeth 114. Even though the width A of the neck 104 is less than the width of the retracted incision 30, the edges 104a and 104b of the neck 104 may still contact the soft tissue 22. Therefore, removing the harsh or angular edges of the neck 104 help minimize trauma, to the soft tissue 22.

Figure 5:
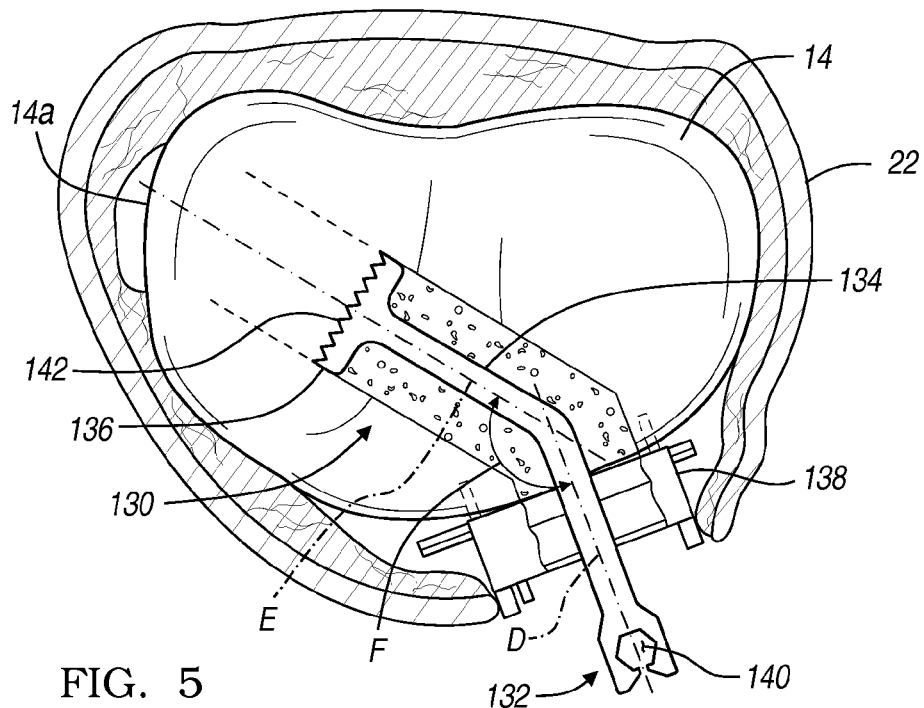
FIG. 5 is an elevational view of a portion of a tibia and an angled saw blade according to a second embodiment.

With reference to FIG. 5, an angled saw blade 130 including a tool engaging end 132, a neck 134, and cutting head 136 is illustrated. The saw blade 130 may be used in conjunction with a cutting block (illustrated herein), which is mounted relative the tibia 14 for the procedure. An incision is made in the soft tissue 22 to allow access of the saw 130 to the tibia 14. The tool engaging end 132 may include a power tool engaging notch 140, such that a power tool may operate the saw blade 130. In addition, the cutting head 136 defines a plurality of cutting teeth 142. Similar to the saw blade 100, the neck 134 of the saw blade 130 may have a width, which is less than the width of the cutting head 136. In addition, the width of the neck 134 may be less than the width of the incision 30 made in the soft tissue 22.

The tool engaging end 132 defines a first longitudinal axis D. In addition, the neck 134 defines a second longitudinal axis E. The first longitudinal axis D of the tool engaging body 132 is angled relative to the second longitudinal axis E of the neck 134. The angle F between the two axes may be any appropriate angle. For example, the angle F may be an obtuse angle to provide access to both sides of the tibia 14. The angle F allows an incision 30 to be placed on a selected side of the tibia 14 through the soft tissue 22. For example, if the tibia 14 is the right tibia, the incision may be formed medially relative to the tibia 14 (as in FIG. 1). If the saw blade 100 were only used, it would be difficult to resect the lateral side 14a of the tibia 14. The saw blade 100 would need to be moved relative to the tibia 14 to reach the lateral side 14a. This may cause trauma to the soft tissue 22 by moving the saw blade 100 or a cutting block. Especially if a cutting block were fixed relative the tibia 14, it would be very difficult and require additional time to move a cutting block relative the tibia 14. With the use of the angled saw blade 130, the lateral side 14a of the tibia 14 can be easily reached with the cutting teeth 142.

The angle F allows the cutting head 136 to be positioned in a space not aligned with the first longitudinal axis C of the tool engaging end 132. This allows the cutting teeth 142 to cut an area of the tibia 14, which is not aligned with the axis D. It will be understood that the angled saw blade 130 may also be angled in the opposite direction. This will allow for the angled saw blade 130 to enter the knee area on the lateral side and reach to the medial side of the tibia 14. Regardless of the size of the angle F or the direction of the angle F, the angled saw blade 130 allows the cutting teeth 142 to cut an area that is not aligned with the longitudinal axis of the tool engaging body 132.

Figure 6:
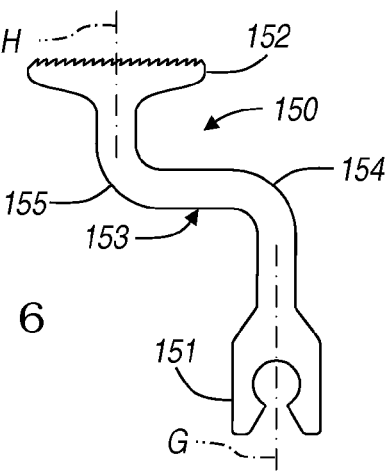
FIG. 6 is a plan view of an offset saw blade according to an embodiment.

With reference to FIG. 6, an alternative angled saw blade or offset saw blade 150 is illustrated. The offset saw blade 150 includes a tool engaging section 151, a cutting head 152, and a neck portion 153. The neck portion 153 includes a first angle or bend 154 and a second angle or bend 155. This allows the cutting head 152 to be laterally offset from the tool engaging section 151 without being angled thereto. More specifically, the tool engaging section 151 extends along a first or tool engaging section axis G while the cutting head 152 extends along a second or cutting head longitudinal axis H. The first axis G is laterally offset from the second axis H, but is parallel thereto. Therefore, the offset saw blade 150 can resect a portion of anatomy not in line with the cutting section 151 yet parallel therewith. The angled sections 154 and 155 may also be referred to or illustrated as "steps" of the neck portion 153.

With reference to FIGS. 7a and 7b, a sliding or translating cutting block assembly 160 is illustrated. The translating cutting block system 160 includes a cutting block 162, which is able to translate or slide on a rail or track member 164. The cutting block 162 includes a post or wall 166a and 166b, which is adapted to push the soft tissue 22 away from a saw blade bore 168 during use, as described further herein. Formed through the cutting block 162 is the saw blade bore 168. Although the cutting block 162 is illustrated to define a saw blade bore or slot 168, which acts as a saw blade guide, as described further herein, a saw blade bore 168 is not required for a cutting block 162. Specifically, the cutting block 162 may also only define surfaces which are used as cutting guides. Therefore, rather than placing the saw blade 100 through a slot formed in the cutting block 162, the saw blade 100 would only ride or translate along a surface of the cutting block 162 to direct the saw blade during use. Therefore, it will be understood that a saw blade bore 168 may define a guiding section or a surface of the cutting block 162 alone may define a guiding section.

Cutting blocks for resection, similar to the cutting block 162 are generally known, such as the 4-IN-1 CUTTING BLOCK, supplied by Biomet, Inc. of Warsaw, Ind. The cutting block 162 guides the saw blade 100 or 132 during a resection procedure to ensure that the proper areas of the boney portions are cut during the resection. However, the cutting block 162 is able to translate medially/laterally, by riding on the rail 164.

Specifically, the cutting block 162 includes a rail engaging section 170, which may define a female dove tail. Likewise, the rail 164 includes a rail translation section 172, such as a complimentary male dove tail. The rail engaging section 170 operably engages the rail translation section 172 so that the cutting block 162 is not able to substantially distract from the rail 164. Nevertheless, the cutting block 162 is able to move medial/laterally in the direction of arrow G by moving along the rail 164. It will be understood that the rail translation section 172 may define any portion complimentary to the guide or cutting block translation portion 170 to allow the cutting block 162 to translate relative the rail 164. For example, the rail translation section 172 may define a "T" shaped projection or a recess. Therefore, the guide translation portion 170 would be complimentarily shaped to engage the rail translation portion 172 for translation of the cutting block 162.

Although the cutting block 162 may be translated along the rail 164, the cutting block 162 may also be selectively locked relative the rail 164, if desired. The cutting block 162 may include a locking pin 174, which can be depressed to engage notches 176 formed in the rail 164. The locking pin 174 may be engaged or unengaged in any position, which can be selected by a user by depressing the locking pin 174. This allows the cutting block 162 to be moved to a selected position relative the rail 164 and locked in place while the saw blade 100 is used. It will be understood that alternative means of locking the cutting block 162 in a selected position can also be used. For example, a set screw can be set against any position on the rail 164 to lock the cutting block 162 in a selected position. This allows for a substantially infinite selection by a user. Alternatively, no locking portion may be provided, such that the cutting block 162 is always free to move, depending upon the selections of the user.

With reference to FIG. 8, an alternative rail or track member 164' is illustrated. The rail member 164' similarly includes the bone anchor portion 180. The rail member 164', however, includes a track translation receiving area 182. The rail member 164' may also include an engaging section 184. The track translation section 172' defines a complimentary engaging section 186 to engage the rail member 164'. In addition, a pin 188 may extend from the track translation section 172' to engage the track translation receiving portion 184. In this embodiment, the rail member 164' engages a separate track translation section 172'. Therefore, a plurality of track translation sections 172' may be provided with the track member 164' and a selection may be made by a user.

Figure 9:
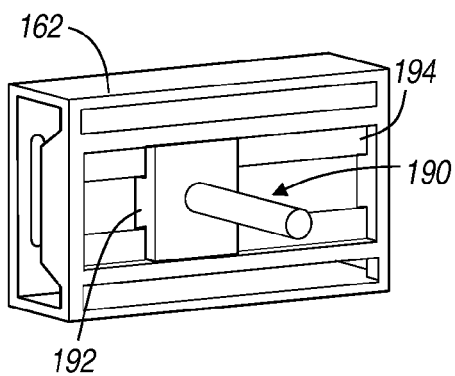
FIG. 9 is a perspective view of a cutting block and rail assembly according to an alternative embodiment.

With reference to FIG. 9, a second alternative rail 190 is illustrated. The rail 190 includes a rail translation section 192 which is shorter than the length of the cutting block 162. The cutting block 162 defines a cutting block translation section 194 which is longer than the rail translation section 192. In this embodiment, movement of the cutting block 192 is allowed because the block translation section 194 is longer than the rail translation section 192. In this manner, the rail 190 need not be longer than the cutting block 162 to allow the cutting block 162 to translate relative the rail 190.

As illustrated in FIG. 10, the rail 164 is mounted to a selected area of the boney portion, such as a distal side 12a of the femur 12 or a portion of the tibia 14 using at least one of a plurality of mounting posts 180. The mounting posts 180 are fit into predrilled holes or bores formed into the femur 12. Specifically, the rail 164 is mounted directly to the femur 12. Therefore, the cutting block assembly 160 is mounted to a boney structure inside the soft tissue 22. Screws may also be used to tighten the posts 180 in place by providing a bore through the post 180. Alternatively, semi-permanent cements or adhesives may be used to fix the posts 180 in place. Other methods may also be used to fix the track 164 in place such as self-driving and tapping screws may be passed through bores formed in the rail 164 to mount the rail 164 in a selected position. It will be understood that any appropriate method may be used to fix the rail 164 to a selected position. Regardless, the rail 164 allows the cutting block 162 to translate to a selected position.

The interaction of the track translation section 172 and the guide translation portion 170 may be substituted with any other proper engagement. For example, the rail 164 may define a male "T" cross-section, which is engaged by a female "T" cross-section formed on the cutting block 162. Any appropriate engagement between the rail 164 and the cutting block 162 may be provided, as long as the cutting block 162 is able to translate relative the rail 164, yet not substantially distract from the rail 164 during or after the translation. It will be understood, however, that the cutting block 162 may distract from the rail 164 if selected. For example, the cutting block 162 may translate relative the rail 164 by distracting the cutting block 162 from the rail 164 and moving the cutting block 162 relative thereto. Moreover, if the cutting block 162 is not locked relative the rail 164, it may be selected that the cutting block 162 distracts from the rail 164 to allow for greater freedom of movement of a user of the cutting block 162.

With continuing reference to FIGS. 7A-10C, a method of using the translating cutting block 160 and the saw blade 100 is illustrated. If it is selected that the knee 10 requires a resection, the incision 30 is made near the knee 10 to allow access to the knee 10 by the various instruments. Once the incision 30 is made, the distal or inferior end 12a of the femur 12 is first resected to form a substantially flat and planar region.

Figure 10A:
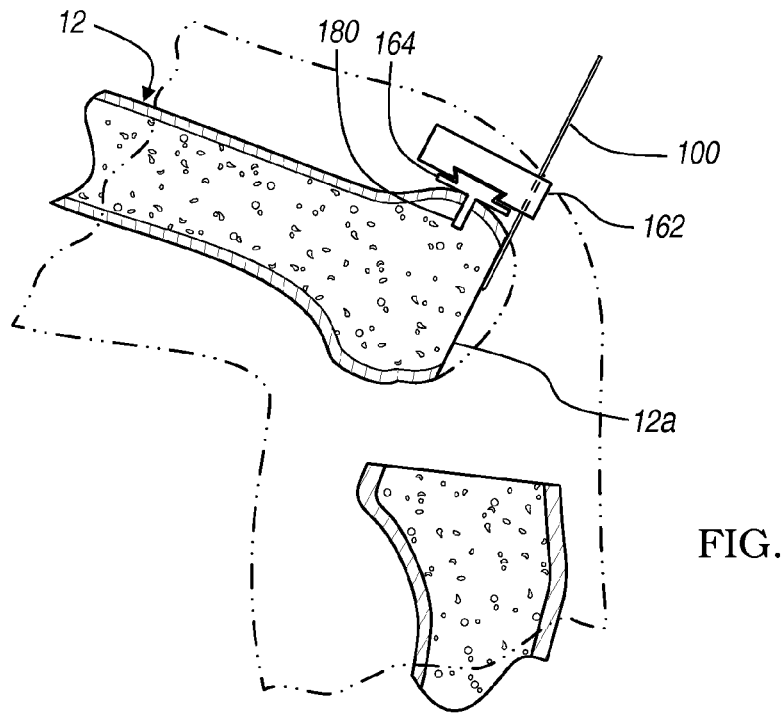
FIG. 10A is a side elevational view of a femur including the cutting block assembly, according to an embodiment, attached thereto.

To form the substantially planar resection of the distal end 12a of the femur 12, with particular reference to FIG. 10A, the cutting block assembly 160 is fixed to an anterior side 12b of the femur 12. The saw blade 100 is then guided with the cutting block 162 through the incision 30 to form the distal cut on the distal end 12a of the femur 12. The interaction of the cutting block 162 and the rail 164 allows the cutting block 162 to be translated medial laterally relative to the femur 12. Moreover, as described above and further herein, because the cutting block 162 is able to translate relative the rail 164, the cutting block 162 can be minimized in size. That is, the cutting block 162 need not be the width of the femur 12 required to be resected because the cutting block 162 is able to move medial laterally relative the femur 12. This resection substantially removes the condyles 26 and 28 and forms a substantially flat area to form the first resection portion of the knee 10 resection.

Figure 10C:
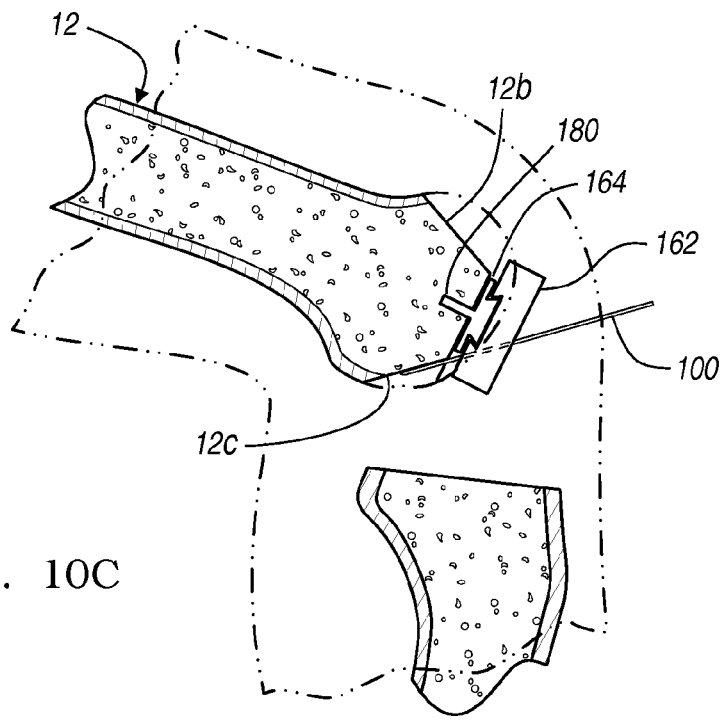
FIG. 10C is a cross-sectional view of the cutting block assembly affixed to a distal end of a femur.
Figure 10B:
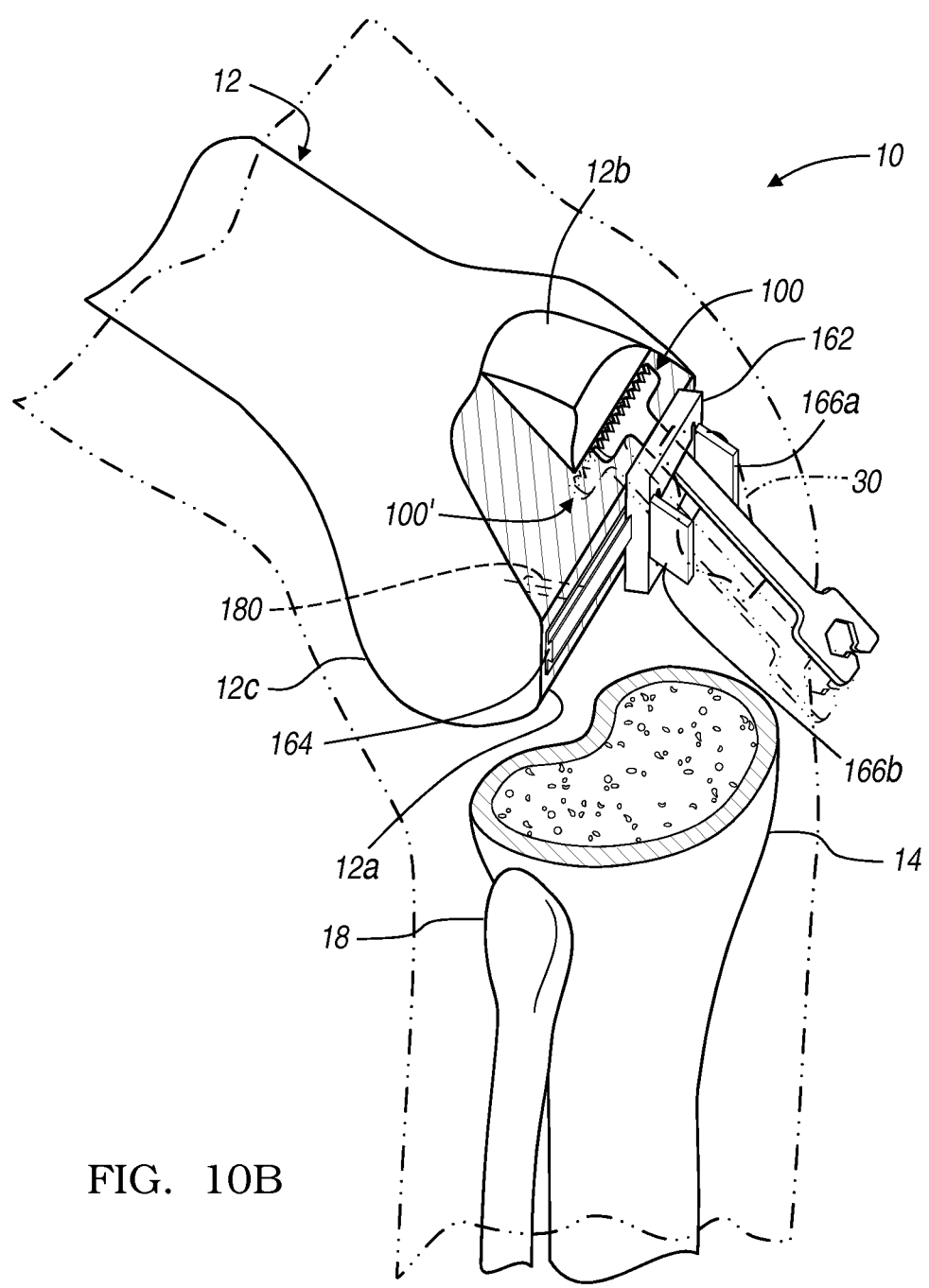
FIG. 10B is a perspective view of a knee joint illustrating an exemplary use of the cutting block and saw blade.

As specifically illustrated in FIGS. 10B and 10C, after the inferior end of the femur 12a is resected, the cutting block assembly 160 can be mounted thereto. Specifically, the rail 164 is mounted to the femur 12 using the mounting posts 180. This allows the rail 164 to be substantially fixed relative the femur 12 for use of the cutting block 162. The cutting assembly 160 is inserted through the incision 30 and mounted to the distal end 12a of the femur 12. This allows the cutting block 162 to translate medially/laterally while mounted on the rail 164, which is mounted or fixed to the femur 12. The cutting block 162, as is generally known, allows for resection of the anterior side 12b and posterior side 12c of the femur 12. Similarly, the saw blade 100 can be inserted through the cutting block 162 to resect the posterior side 12c of the femur 12. Therefore, the exemplary illustration resecting the anterior side 12b of the femur 12 is not meant to limit the following claims.

After the cutting assembly 160 is mounted to the femur 12, using proper methods, such as adhesives or screws, the saw 100 can be inserted through the incision 30 and through the cutting block 162. This allows the saw 100 to be properly aligned relative to the femur 12 using the cutting block 162. Therefore, the saw blade 100 can resect portions of the anterior side 12b of the femur 12. Due to the narrowness of the neck 104 of the saw blade 100, the incision 30 may be small, even though the saw blade 100 must move from side to side to resect portions of the femur 12. For example, the saw blade 100 illustrated in solid lines, shows the position of the saw blade before it moves to resect a portion of the femur 12. The saw blade 100', shown in phantom lines, illustrates a portion of the vibrational motion of the saw blade 100 while in operation. The narrow neck 104, however, does not substantially engage the edges of the incision 30 during this process. Therefore, the trauma to the soft tissue 22 is minimized due to the narrow neck 104. Similarly, the cutting block 162 and cutting assembly 160 as a whole is minimized in size to reduce trauma to the soft tissue 22 during the positioning and removal of the cutting assembly 160.

After the saw blade 100 has been used to resect a portion, for example the lateral side, of the femur 12, which it is able to reach in a first position, the cutting block 162 can be translated along the rail 164 to a second position. In this second position, the cutting block 162 may be held or locked in place with the locking pin 174. Alternatively, no locking mechanism may be used to allow the cutting block 162 to move freely depending upon the desires of the user. Nevertheless, the cutting block 162 may translate to the medial side of the knee 10, as the knee 10 illustrated in FIG. 6 is a right knee, such that the saw blade 100 is able to easily resect the medial side of the femur 12.

The saw blade 100 may be positioned to cut the anterior side 12b of the femur on the medial side of the femur 12. In this way, the rail 164 needs only be mounted once while the cutting block 162 can be translated along the rail 164 to cut all the necessary portions of the anterior side 12b of the femur 12. Similarly, the cutting block 162 may be removed and rotated to cut the posterior side 12c of the femur 12 with the saw blade 100. An appropriately configured cutting block 162 allows the saw blade 100 to resect both the anterior 12b and the posterior 12c of the femur 12 without rotating the cutting block 162.

Extending from the cutting block 162 are the soft tissue holders or pushers 166a and 166b. The soft tissue pushers 166a and 166b are positioned to ensure that the soft tissue 22 does not intersect the guide bore 168 of the cutting block 162. Moreover, the soft tissue pushers 166a and 166b help move the incision 30 relative the femur 12 during the procedure. Specifically, the incision 30 is a substantially small incision, such that the instruments may be inserted into the knee 10, but not so large as to produce large amounts of trauma to the soft tissue 22. Nevertheless, the movement of the cutting block 162 can move the incision 30 and the surrounding soft tissue 22 relative the femur 12 to allow for the cutting block 162 to easily move along the rail 164. In this way, the cutting block 162 helps reduce trauma to the soft tissue 22 surrounding the knee 10. It will be understood that any appropriate saw blade may be used in conjunction with the cutting block 162, therefore the cutting assembly 160, it is not necessarily exclusive to use with the narrow saw blade 100.

With reference to FIG. 10C, the femur 12 is illustrated resected such that the anterior side 12b has been resected to form a substantially flat and planar portion. In addition the posterior side 12c of the femur 12 has also been resected. The saw blade 100 has been inserted through the cutting block 162 to resect the posterior side 12c of the femur 12. In this way, the rail 164 need only be mounted once to resect both the anterior side 12b and the posterior side 12c of the femur 12. Moreover, the use of the translating cutting block 162 allows the rail 164 to be positioned only once to resect both the medial and lateral portions of the femur 12 as well. This allows the rail 164 to be mounted only once to the femur 12 to resect all portions of the anterior side 12b and the posterior side 12c. This assists in reducing trauma to the femur 12 during the resection procedure and can decrease healing time after the procedure is completed.

According to various embodiments, as discussed above and herein, a guiding member, for example, a translating or sliding cutting block, can be used to form various portions or resections of a selected bony portion. For example, as discussed above, the translating cutting block 162 may translate relative to the rail 164 to form a resection of a portion of a bone or other selected anatomical portion. The cutting block 162 may assist in guiding a cutting tool even if the cutting block is not the same size or dimension, in at least one direction, as the resection to be made. Nevertheless, various cutting blocks may be used in various methods to form resections of various portions of the anatomy.

Figure 11:
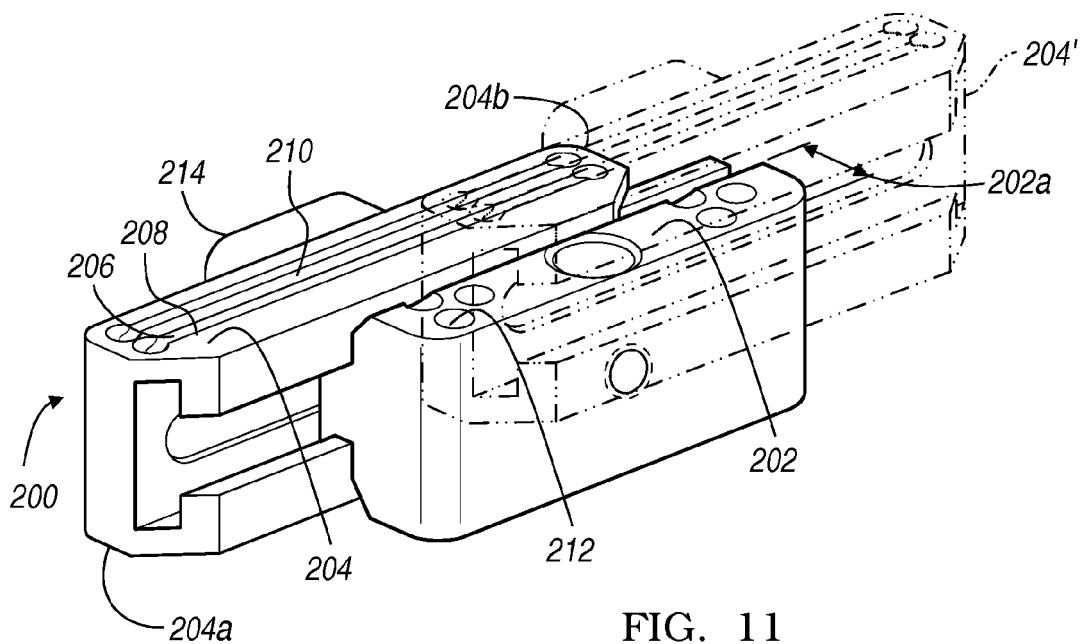
FIG. 11 is a perspective view of a moveable guide block.

With reference to FIG. 11, a guide member 200, such as a translating or sliding cutting block, is illustrated. The translating cutting block 200 may be used to form any appropriate portion, such as a resection in a selected portion of the anatomy. For example, the cutting block 200 may be used in forming a distal resection of a the femur 12. Further, it will be understood that the cutting block 200 may be used with any appropriate portions to assist in or guide the cutting block 200 for various preparations.

Regardless, the cutting block 200 may generally include a first attachment and/or rail portion 202. The translating cutting block 200 may also include a guide or translating portion 204. The guide portion 204 may include a slot or cutting guide 206 that may define a cutting guide surface 208. The guide surface 208 may be any portion defined by the cutting or translating member 204 to assist in guiding a selected instrument, such as the saw blade 100, to form a selected resection. Nevertheless, it will be understood that the translating guide portion 204 may be used to guide any appropriate member or instrument relative to a selected portion of the anatomy to perform a selected procedure. Moreover, the translating or guide member 204 may also include a second guide slot 210 or any appropriate number of guide slots for various purposes or applications.

With reference to FIG. 11, the translating cutting block 200 includes the translating member 204 that can translate relative to the fixed or rail member 202. As illustrated, the guiding block portion 204 may move from a first position to a second position 204', illustrated in phantom. In this way, the translating cutting block 200 may be positioned relative to a selected portion of the anatomy to cut a first portion of the anatomy or guide a selected instrument relative to a portion of the anatomy, and move to a second position to cut a second portion of anatomy or guide an instrument relative to a second portion of the anatomy. In this way, the translating block 200 may include a size, such as that discussed above, that is smaller than a selected working area. For example, the cutting block 200, or any portion thereof such as a first end 204a and a second end 204b of the guide member, may be less than about 8 cm, and may include an exemplary length of about 4 cm. One may understand that various instruments may be used for minimally, less invasive, or conventional open procedures. The reduced size and characteristics of various instruments may reduce the recovery time experienced by a patient after a procedure. Also the time for the procedure may be reduced as well as many other effects.

The rail member 202 may define a tenon 202b of a rail portion. The rail member 202 may also define any other projection, such as a "T" or "D" shape or any appropriately shaped depression. The guide member 204 may define a complimentary portion, such as a mortise 204c, to associate with the tenon 202b. The guide member 204 may include or define any other depression or projection to associate with the rail member 202. Also, as discussed above, various portions may be provided to lock or fix the guide member 204 relative to the rail member 202. Alternatively, or in addition thereto, the guide member 204 may move generally freely relative to the rail member 202 in a selected manner.

The rail member 202 may include a bore or a plurality of bores 212 to receive a selected member, such as a pin or screw to fix the translating mechanism 200 relative to a portion of the anatomy. It will be understood, however, that any appropriate mechanism may be provided to assist in positioning the rail or fixed member 202 relative to a selected portion of the anatomy. For example, a pin or member 236 (FIG. 14) may extend from a surface of the fixed member 202 to assist in holding the rail member 202 relative to a selected portion of the anatomy.

Further, the rail member 202 may include a plurality of mechanisms to substantially assist in positioning or selectively positioning the rail member 202 in a selected position. For example, a plurality of the bores 212 may be provided, each including a different orientation relative to the rail member 202. Therefore, various mechanisms, such as pins or screws, may be positioned through a selected plurality of the bores to position the rail member 202 in a selected position that may be different depending upon the selection of bores 212. Positioning the rail member 202 in a different position may allow for movement of the guiding block 204 to various orientations relative to the anatomy. Therefore, it will be understood that the cutting block 200 may be positioned relative to the anatomy in any appropriate way to assist in guiding a selected mechanism or tool relative to the anatomy.

Further, the translating guiding block 200 may include a central or positioning bore 214. The positioning bore 214 may be provided through any appropriate portion of the translating cutting block 200 to assist in associating the translating cutting block 200 or the selected instrument. For example, an intramedullary rod or positioning member, as discussed herein, may be positioned relative to the anatomy and a portion of the rod may be engaged or associated with the central bore 214 to position the cutting block 200 relative to the rod and the anatomy.

Figure 12:
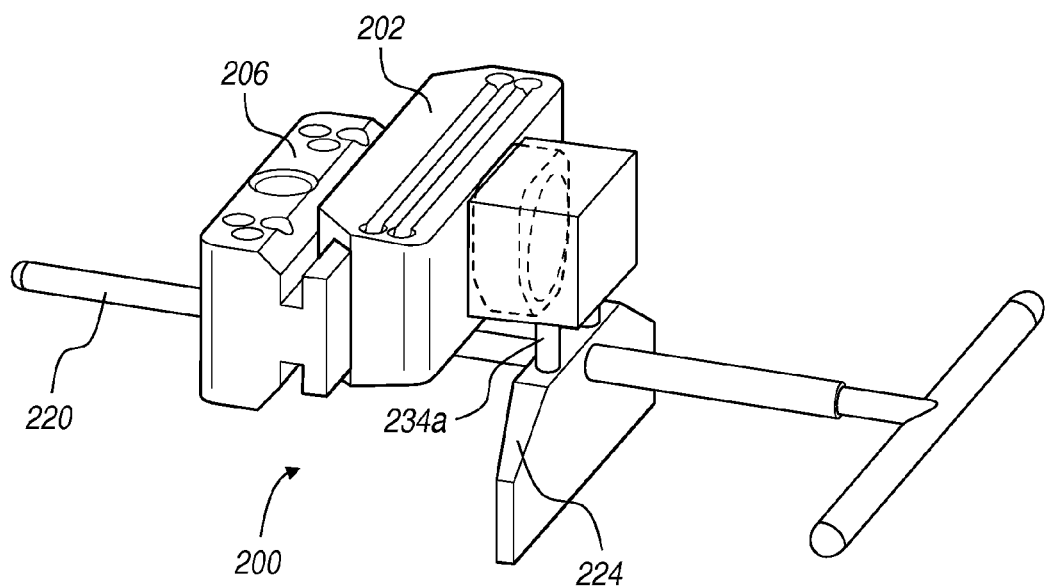
FIG. 12 is a perspective view of a movable guide block assembly.

With reference to FIGS. 11 and 12, the translating cutting block 200 may be positioned relative to an intramedullary (IM) rod 220 for use of the translating cutting block 200, or at least positioning of the translating cutting block 200. The IM rod 220 may be positioned relative to a paddle or instrument 224 operable to be positioned in the femur 12. It will be understood that the cutting block 200 may be positioned in any appropriate manner and using the IM rod 220 is merely exemplary.

Figure 13:
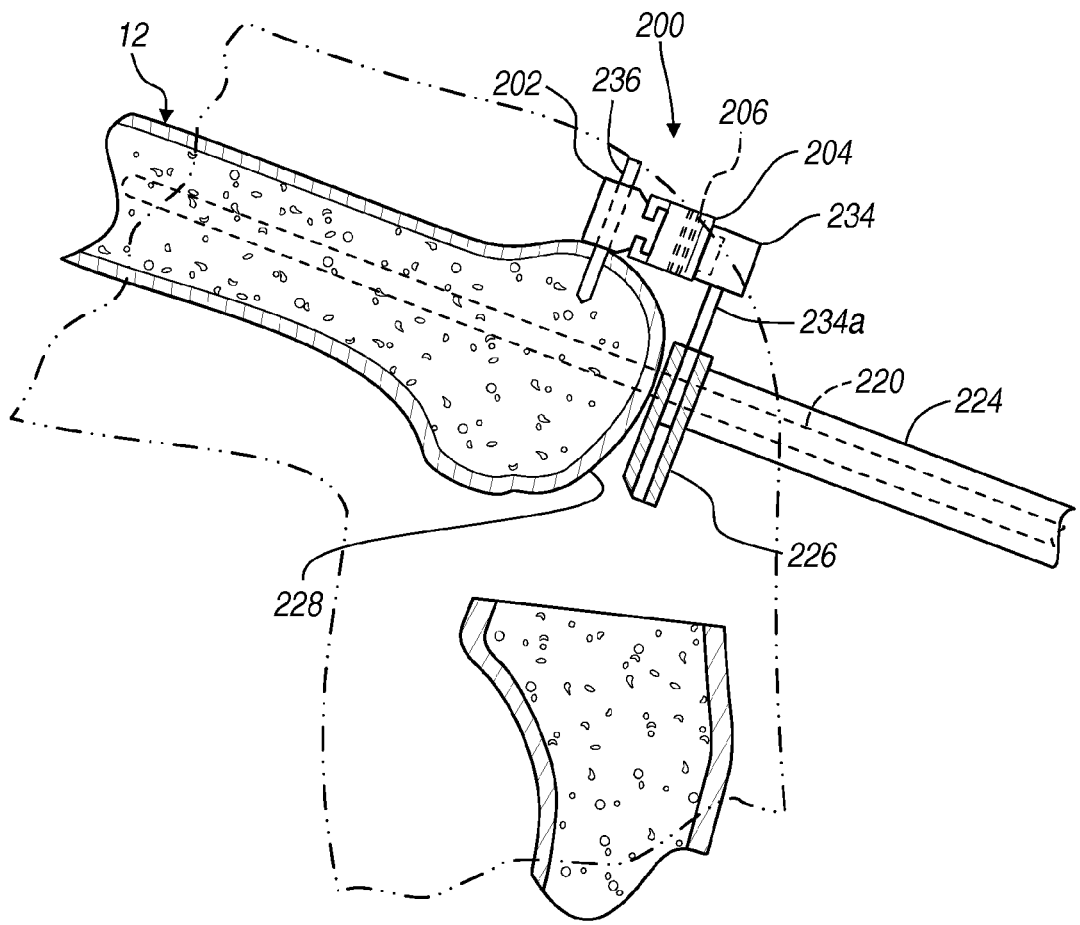
FIG. 13 is a partial cross-sectional view at a knee including a movable guide assembly.
Figure 14:
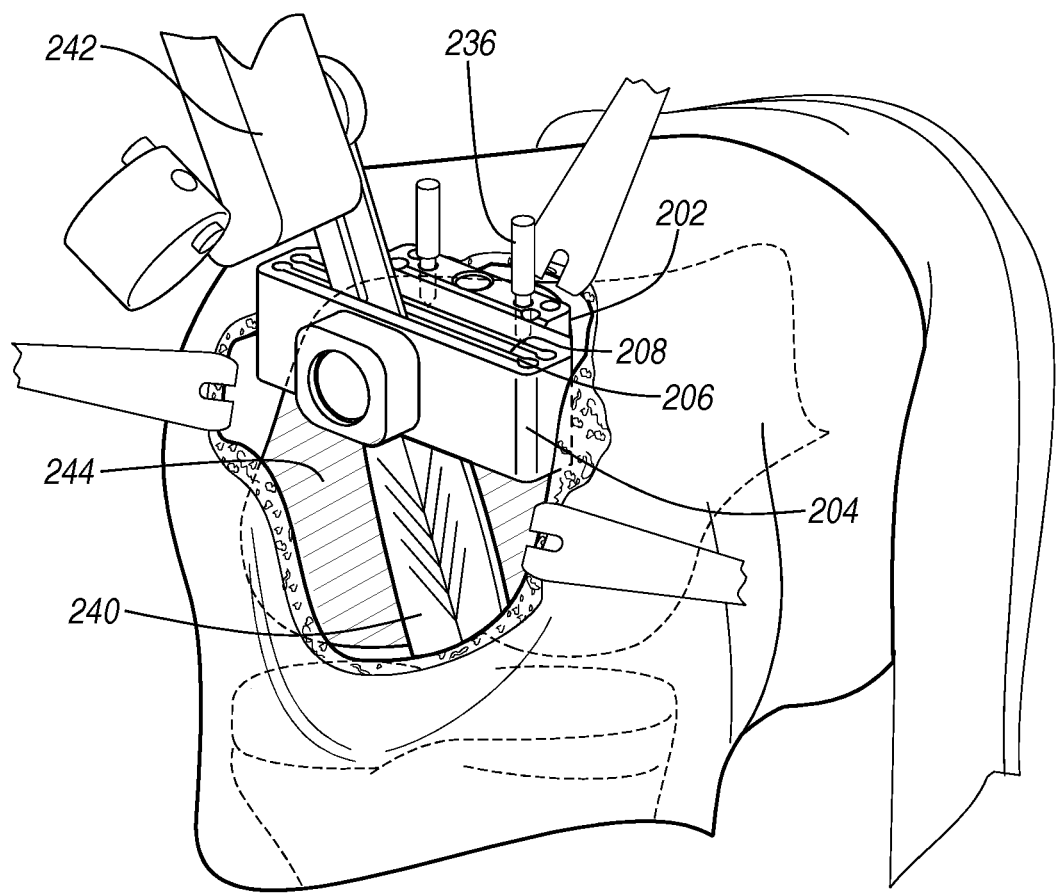
FIG. 14 is a perspective environmental view of a movable cut guide in use.

With reference to FIGS. 13-14, an exemplary method of using the cutting block 200, such as for a translating distal resection cutting block to resect a distal portion of the femur 12, is illustrated. With reference to FIG. 13, the paddle instrument 224 may be interconnected with the IM rod 220 and positioned relative to, such as inserted into, a portion of a bone, such as the intramedullary canal of the femur 12. The paddle instrument 224 may be selected from one or more paddle instruments based upon a paddle portion 226. The paddle portion 226 may be selected for various purposes, such as selecting a distance from a distal portion 228 of the femur 12. The paddle portion 226 may also be selected for various other purposes, such as selecting a varus and/or valgus angle for formation of the distal cut of the femur. Therefore, it will be understood that the paddle portion 226 or the instrument 224 may be selected for various appropriate purposes. For example, a plurality of the instruments 224 may each include different paddle portions 226. The different paddle portions may provide different attributes, such as a selected varus and or valgus angle. The angle may be translated in positioning the cutting block 200 with the instrument 224, as discussed herein.

Once the intramedullary rod 220 and the paddle instrument 224 are positioned relative to the femur 12, an attachment mechanism 234 may be positioned relative to the femur 12 and the paddle instrument 224. The connection mechanism 234 may be provided to interconnect, at least temporarily, the translating cutting block 200 with the instrument 224 for selectively positioning the translating cutting block 200 relative to the femur 12. It will be understood that the connection portion 234 may not be necessary and may be provided to allow for a selected interconnection. Nevertheless, the translating cutting block 200 may be positioned with the paddle instrument 224 without use of the connection instrument 234. The translating cutting block 220 may associate or be interconnected with the paddle instrument 224 without an internal or separate connection means. Nevertheless, it will be understood that the connection instruments 234 may be used for various purposes.

Generally, the interconnection mechanism includes a pin 234a that can interconnect with the paddle portion 226 of the instrument 224. The pin 234a allows an interconnection between the guide block 200 and the paddle portion 226. As discussed above this may assist in forming the appropriate angles in the resection. Also, the pins 234a allow for selectively removing the various portions to assist in the resection or for other purposes.

The translating cutting block 200 may then be interconnected with the interconnection portion 234. For example, the connection member central bore 214, extending from the translating or guide portion 204 of the translating cutting block 200, may interconnect with the interconnection mechanism 234. The interconnection of the translating portion 204 with the interconnection mechanism 234 may allow for selective positioning of the guide surfaces 208 relative to the femur 12 in a selected manner. The interconnection may be any appropriate connection. For example, a magnet or magnets may be provided to interconnect the translating cutting block 200 for positioning thereof. As discussed above, one or more of the guide surfaces 208 may be provided and defined by the guide member 204 for guiding a selected instrument, such as a saw blade. Therefore, positioning the guide member 204 with the interconnection mechanism 234 may assist in selectively positioning the guide surfaces 208 relative to the femur 12 in a selected manner.

Once the guide portion 204 is interconnected with the interconnection mechanism 234, the rail portion 202 may be interconnected with the femur 12 near the distal end 228 in a selected manner. For example, a pin or screw 236 may be provided to interconnect the rail portion 202 with the femur 12. The pin 236 may be any appropriate pin, and for example, may include a quick release pin, such as a Quick-Release Drill Bit™, provided by Biomet, Inc. of Warsaw, Ind. Although any appropriate mechanism may be used to hold or fix the rail portion 202 to the femur 12, the quick release pins may allow for an easy and efficient connection of the rail portion 202 with the femur 12 and for an efficient and effective removal therefrom.

It will be understood that the rail member 202 may be connected to the femur in any appropriate location. Nevertheless, it may be selected to position the bores of the rail member 202 away from the distal end 228 of the femur 12. The bores 212 may also, or alternatively, be positioned near the distal end 228 of the femur 12. Also the distance the bores 212 are positioned from the guide member 204 may be selected for various purposes.

Once the translating cutting block 200 has been positioned relative to the femur 212 in a selected manner, the paddle instrument 224 and the IM rod 220 may be removed from the femur 12. The removal of the paddle portion 224, the interconnection portion 234, and the IM rod 220 may allow for a clear or easier access to the distal portion 228 of the femur 12. After the IM rod 220 has been removed from the femur 12, a selected instrument may be guided with the translating guide portion 204.

With reference to FIG. 14, the translating guide portion 204 may guide a selected instrument, such as a saw 240. The saw 240 may be any appropriate saw, such as a reciprocating saw powered by a hand tool 242 or the saw 100. The saw 240 may pass through the guide slot 206 and be guided along the guide surface 208. In this way, the guide portion 204 may be provided to guide the saw 240 relative to the femur 12. This may allow for a resection of the distal portion 228 of the femur 12 to form a substantially planar or resected surface 244 of the femur 12.

The resected surface 244 of the femur 12 may be any selected size. For example, the resected portion 244 of the femur 12 may be substantially a width or distance between the epicondyles of the femur 12. The distance between the epicondyles may be dependent upon the size of the patient, but may generally be about 4 cm to about 13 cm (about 1.5 inches to about 5 inches). As discussed above, the guide member 204 may include a length between the first end 204a and the second end 204b that is less than the distance of a selected femur. Therefore, as discussed above, the guide member 204 may move relative to the rail or fixed portion 202. Thus, once the resected surface 244, or a portion thereof, is resected such as the length of the slot 206 defined by the guide member 204, the guide member 204 may be moved relative to the rail portion 202 to complete a resection of the femur 12 in a selected manner.

Therefore, the guide member 204 need not include a length, for example a length of the guide surface 208, an entire dimension or size of the surface to be resected. As discussed above, the guide member 204 is able to move, such as translate or rotate, relative to the rail member 202. Thus the guide member 204 may allow movement of the guide surface 208. In this way the resection may be completed using the guide member 204 and generally not requiring the resected surface, or a part thereof, to guide the tool to form the resection. The guide member 204 may provide the guide surface for the entire resection to be performed.

Moreover, the rail portion 202 may be moved due to the plurality of the bores 212 in the rail member 202. Therefore, for example, if the movement or translation of the guide member 204 is not great enough to complete a resection of the femur 12 at a selected manner, the rail portion 202 may be moved relative to the pins 236. This may allow for further resection to form the resected surface 244. The bores 212 may also allow for additional resection to be performed for various reasons. The pins 236 may be positioned in various bores to select an amount of resection to occur.

Regardless, it will be understood that the guide member 204 need not be an extended or large size, due at least in part to a movement of the guide member 204 relative to a portion of the anatomy, such as the femur 12. Regardless, the guide member 204 may be used to guide the entire formation of the resected surface 244 due, at least in part, to the movement of the guide member 204. For example, the resected surface 244 or a portion thereof, need not be used to guide the saw 240 relative to another portion of the anatomy, such as to complete the resected surface 244, due at least in part to a movement or a translation of the guide member 204.

Further, the rail portion, including a depth or dimension 202a may allow for positioning of the rail member 202 relative to a selected portion of the femur 12. For example, the translating block 200 may be positioned substantially near the distal portion 228 of the femur 12, such as substantially near the condyles. Therefore, the incision formed in the soft tissue relative to the femur 12 may be substantially small or minimized and still allow passing and positioning of the translating block 200. The bores 212 defined in the rail portion 202 allow for fixing the translating member 200 relative to the anatomy, such as the femur 12, near the distal portion 228 of the femur 12 for various purposes, such as reducing the size of the incision.

In addition, as discussed above, various other portions of the anatomy may be resected or prepared, such as a proximal portion of a tibia. In addition, as discussed above, various other resections of the femur 12 may be formed. Various guide members, such as translating movable guide members may be used to form various resections of the femur, such as an anterior and posterior cut, and an anterior and posterior chamfered cut. The various resections of the femur 12 may allow for positioning of a distal femoral implant on the femur 12 through the incision. The distal femoral implant may articulate with the tibia or articulate with a tibial implant according to various embodiments. Nevertheless, it will be understood that various resections may be formed to allow for replacement or repair of selected anatomical portions.

Figure 15:
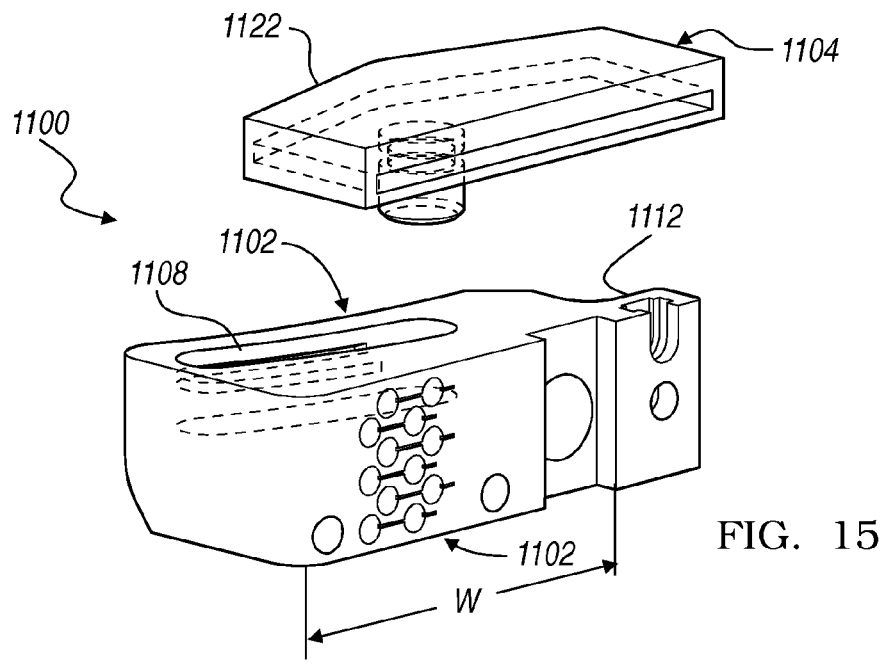
FIG. 15 is an isometric view of a tibial resection apparatus according to the present teachings.
Figure 16A:
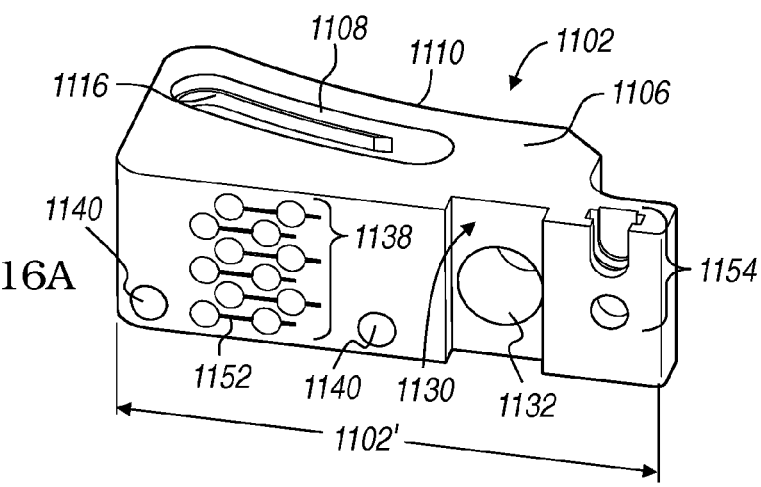
FIG. 16A is an isometric view of an exemplary support block for the tibial resection apparatus of FIG. 15.
Figure 21B:
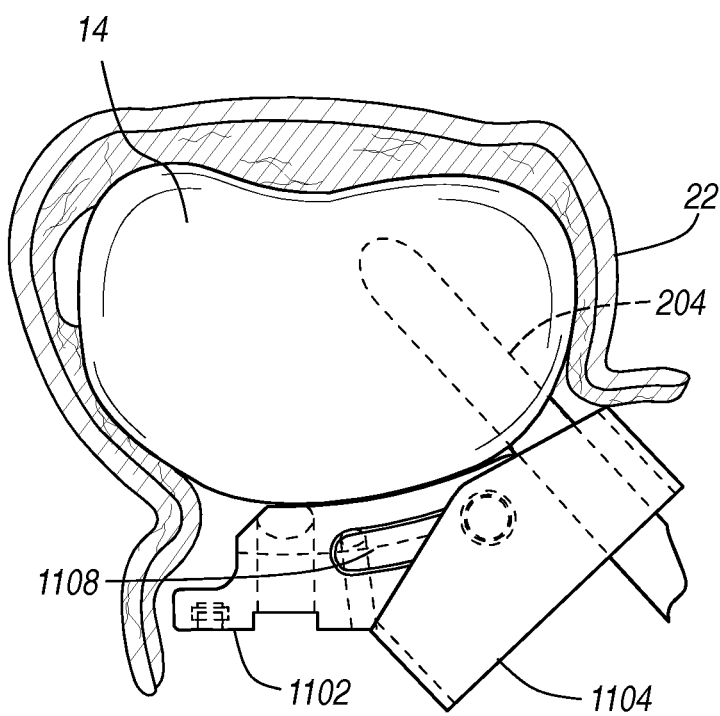
FIG. 21B is an environmental plan view of a tibial resection guide according to the present teachings in a second position on a right leg.
Figure 21A:
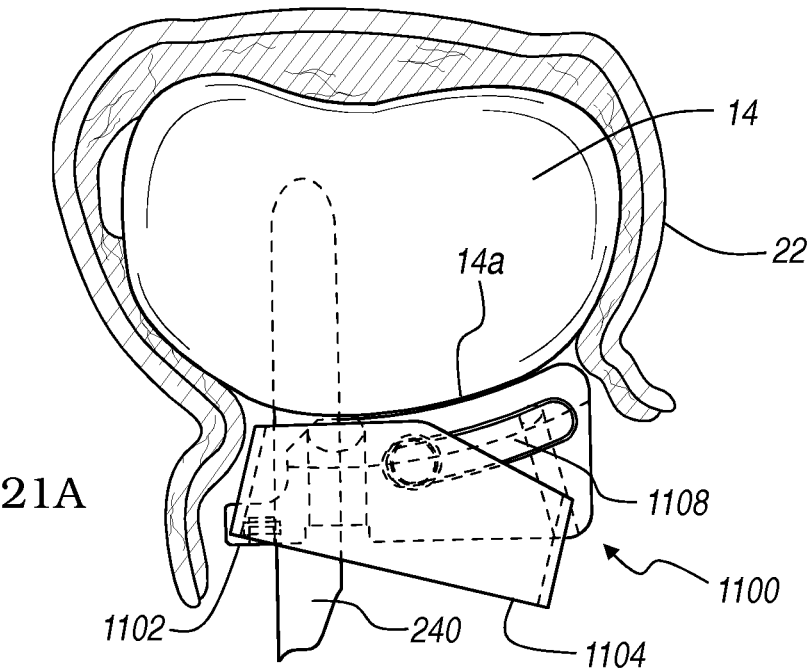
FIG. 21A is an environmental plan view of a tibial resection apparatus according to the present teachings in a first position on a right leg.
Figure 22:
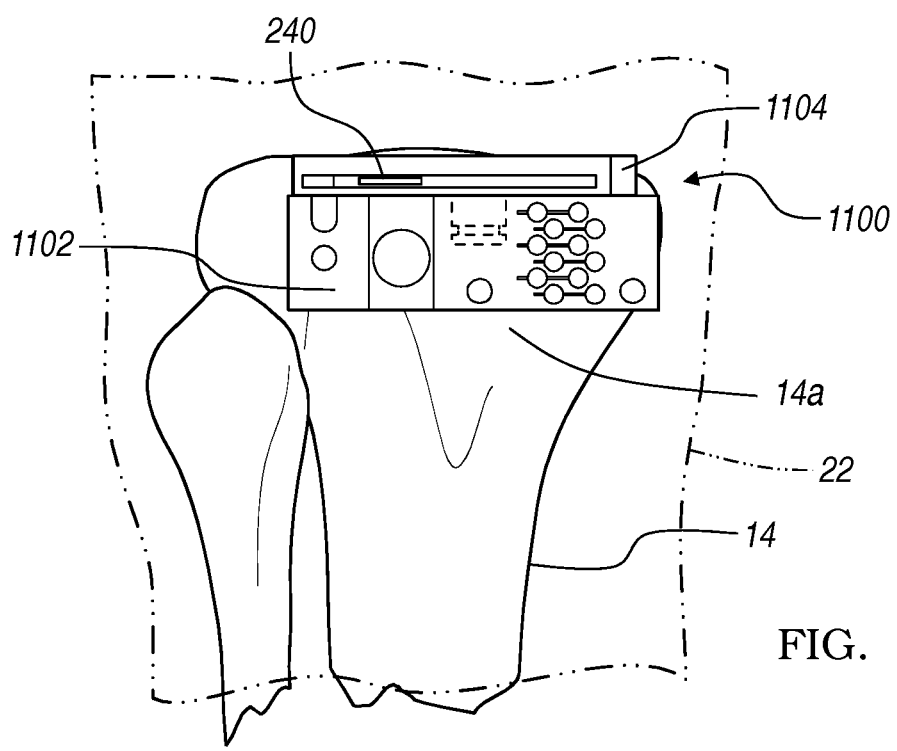
FIG. 22 is an environmental side view of a tibial resection apparatus of FIG. 21 on a right leg.

Referring to FIG. 15, an exemplary tibial resection apparatus 1100 according to the present teachings includes a support block 1102 and a cutting guide 1104. The support block 1102 may have a superior surface 1106 (FIG. 16A) that defines a groove 1108. The groove 1108 may be oriented medially-laterally and can be curved generally parallel to a curved attachment surface 1110 of the support block 1102. The support block 1102 of FIG. 16A is configured for a left leg. It will be understood, as illustrated in FIGS. 21A-22, that a support block 1102 may also be configured for the right leg. The curved attachment surface 1110 is configured to mate with at least a portion of the medial surface 14a of a proximal portion of the tibia 14, as illustrated in FIGS. 21A and 22.

Figure 20:
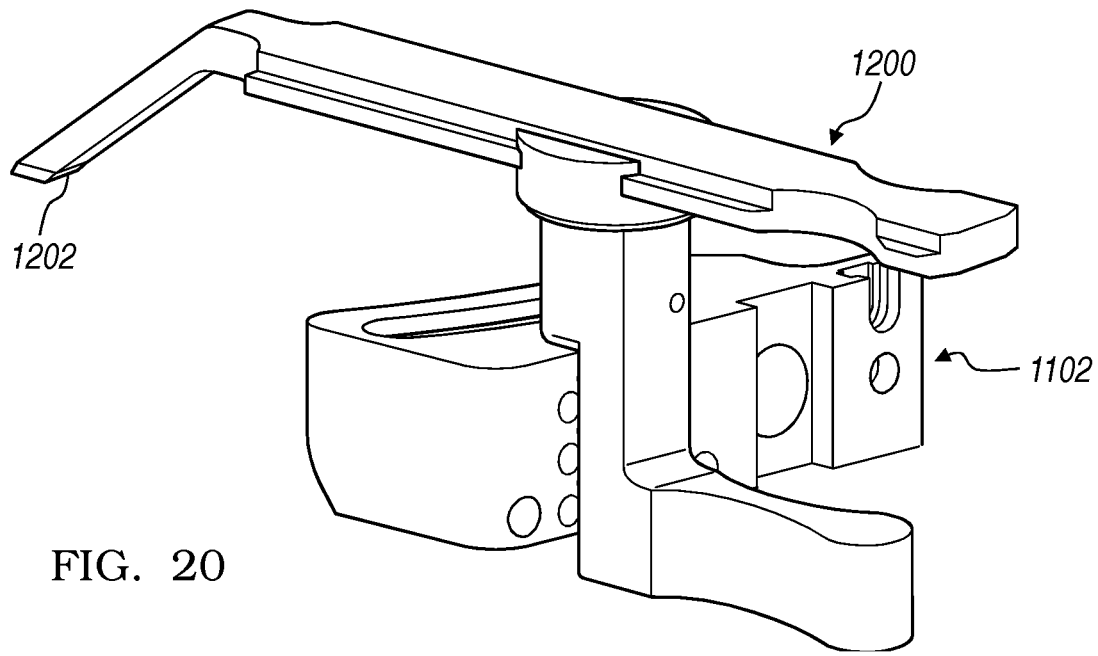
FIG. 20 is an isometric view of a support block of FIG. 15, shown a stylus.
Figure 23:
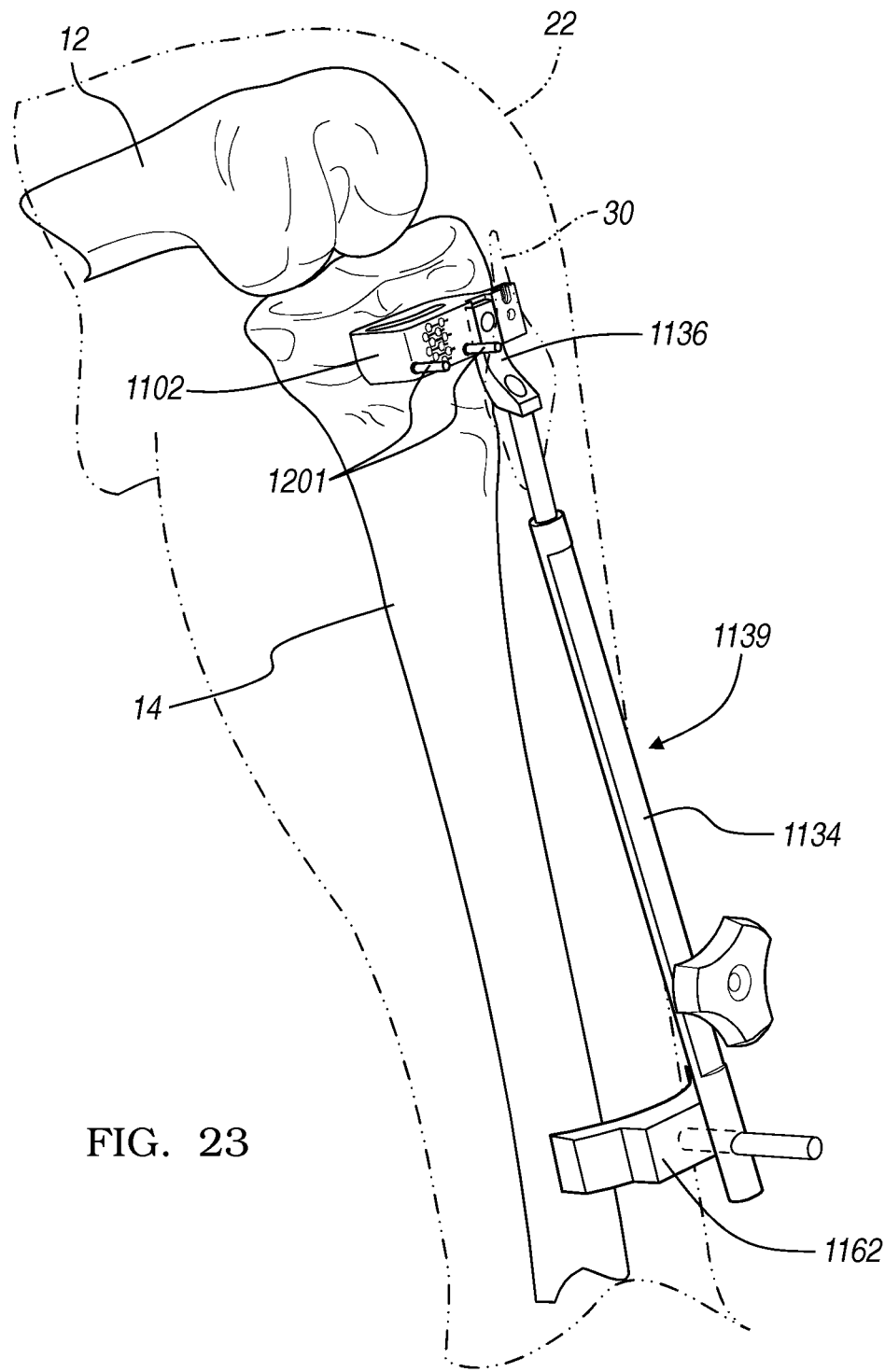
FIG. 23 is an environmental isometric view of a support block and tibial guide attached to the tibia according to the present teachings.

Referring to FIGS. 16A, 20 and 23, the support block 102 can include a cut-out 1130 and an aperture 1132 that can receive a fastener or holding portion 1136 for attaching an extramedullary rod 1134 of a standard tibial guide 1139. The standard tibial guide 1139 can be attached to the distal tibia with a yoke or other known attachment device 1162. A set of holes 1138, including a plurality of pairs of holes 1138, can be arranged in parallel and equidistant pairs, or any appropriate format, on a front surface 1150 of the support block 1102. The holes 1138 are configured to selectively receive respective locking pins of a tibial stylus 1200 for setting the depth of resection.

When the stylus 1200 engages the pair of holes 1138 located most inferiorly from the superior surface 1106, a tip 1202 of the stylus 1200 is at the level of the saw guide slot 1112 of the cutting guide 1104. Engaging the stylus 1200 with the next pair of holes 1138, corresponds to an increase of the distance of the tip 1202 by a predetermined amount equal to the spacing between the consecutive pairs of holes 1138, such as, for example, about 2 mm. Engraved lines or other indicator markings 1152 can be provided along each pair of holes 1138 to indicate the level of the tip 1202 at each location of the stylus 1200, thereby functioning as a stylus scale.

Other holes 1140 through the support block 1102 can be provided for receiving fasteners, such as a locking pin 1201, such as those discussed above, that attach the support block 1102 against the tibia 14. The support block 1102 can also include an engagement area 1154 that can include a slot or opening for receiving a handle 1160 with openings 1164 for supporting other alignment rods, as illustrated in FIG. 24.

The cutting guide 1104 may define a saw blade slot 1112 and includes a peg 1114 extending from an inferior surface 1105 of the cutting guide 1104. The peg 1114 is configured to be received in the groove 1108, such that the cutting guide 1104 can slide along the groove 1108 relative to the support block 1102. The groove 1108 and the peg 1114 can include complementary engagement or locking features, such as, for example, a rim 1116 projecting from the wall of the groove 1108 into the groove 1108 and a slot 1118 defined by upper and lower shoulders 1120 of the peg 1114. When the peg 1114 is engaged with the groove 1108, the cutting guide 1104 can stably rotate about the peg 1114 relative to the support block 1102. This can allow the cutting guide 1104 to be rotated away or toward the medial surface 14a of the tibia 14 providing greater freedom of movement to the cutting saw blade. The cutting guide 1104 can have a straight edge, one angled edge, or two angled edges 1122 on the side facing the tibia 14. The edges 1122 assist in moving and help provide clearance for movement of the cutting guide 1104 during movement of the cutting guide relative to eh support block 1102 (FIGS. 21A and 21B).

The saw blade slot 1112 has a width W (FIG. 15) that is generally greater than a corresponding width of the saw blade 240, or other appropriate saw or cutting tool, to allow a swinging motion of the saw blade relative to the saw blade slot 1112, in addition to the motion of the saw blade that is provided by the sliding motion of the cutting guide 1104 along the groove 1108. Cutting can begin at the medial surface 14*a* of the tibia 14 and proceed posteriorly and laterally, advantageously facilitated by the sliding motion of the cutting guide 1104. It will be understood that the resection can begin at any appropriate location and proceed according to various methods.

Figure 16B:
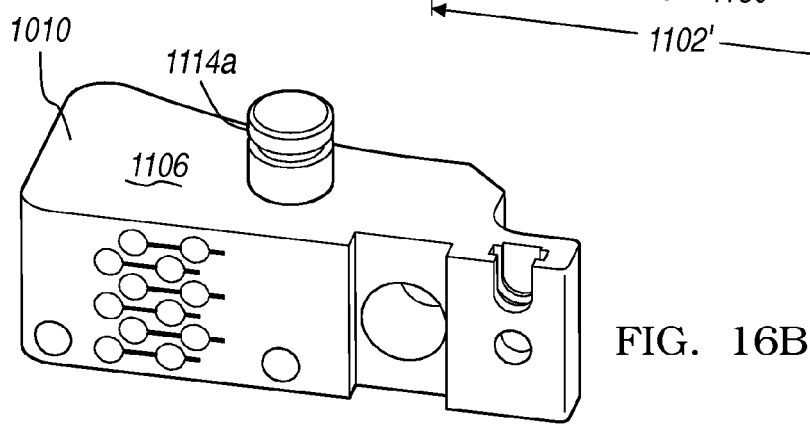
FIG. 16B is an isometric view of an exemplary support block for a tibial resection apparatus according to the present teachings.
Figure 17A:
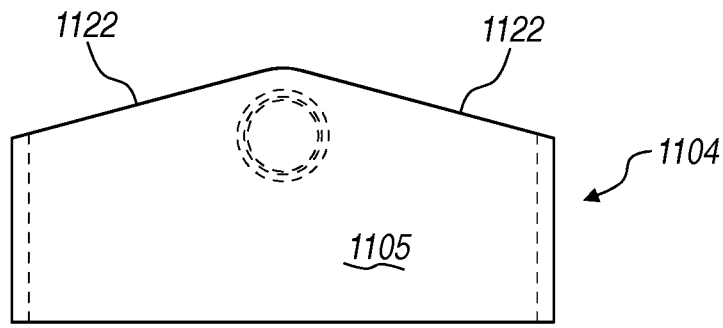
FIG. 17A is a top view of an exemplary cutting guide for the tibial resection apparatus of FIG. 15.
Figure 18:
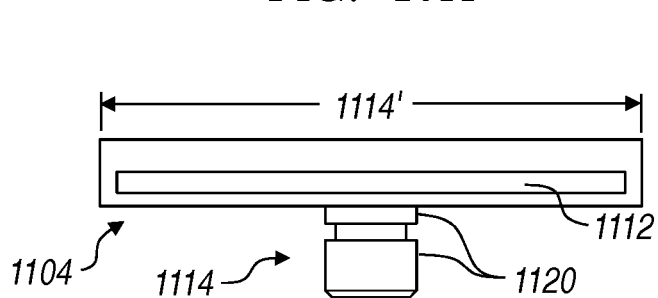
FIG. 18 is a front view of the cutting guide of FIG. 17A.
Figure 19:
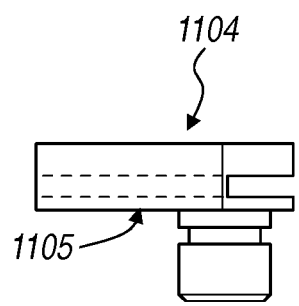
FIG. 19 is a side view of the cutting guide of FIG. 17A.
Figure 17B:
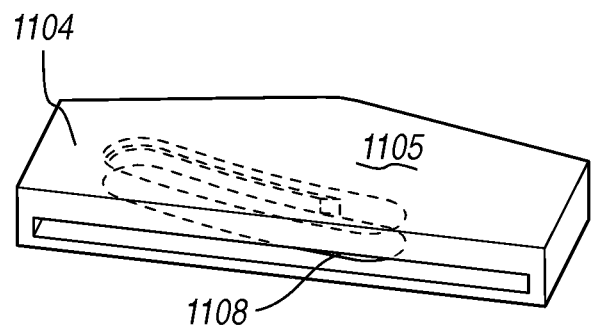
FIG. 17B is a top view of an exemplary cutting guide for coupling to the support block FIG. 16B.

The tibial resection apparatus 1100 of FIG. 15 is merely exemplary. Arcuate sliding is allowed between the support block 1102 and the cutting guide 1104 by including a groove-peg engagement device. Although exemplary, the groove 1108 is defined in the superior surface of the support block 1102 and the peg 1114 extends from the inferior surface 1105 of the cutting guide 1104. It will be understood that other sliding engagement devices are contemplated. For example, the groove 1108 can be defined in the inferior surface 1105 of the cutting guide 1104, and a peg 1114*a* can extend from the superior surface 1106 of the support block 1102, as illustrated in FIGS. 16B and 17B. The groove and peg arrangement is generally configured to enable relative sliding between the support block 1102 and the cutting guide 102 along an angled and/or arcuate path defined by the groove 1108, whether the groove 108 is defined on the support block 1102 or the cutting guide 1104. Further, the peg 1114 can be modularly coupled to the support block 1102 or the cutting guide 1104. The peg 1114 can also be a bolt, a pin or ball configured for engagement with the groove 1108. The engagement of the peg 1114 and the groove 1108 may also allow for rotation of the cutting block 1104 relative to the support block 1102. Thus the cutting guide 1104 may move in any appropriate manner relative to the tibia 14 and the support block 1102.

The support block 1102 may be positioned relative to the tibia 14 using any appropriate mechanism, such as the support rod or extramedullary rod 1139 or the handle 1160 (see FIG. 24). The following discussion may be readily adapted for use with any appropriate support mechanism and the use of the extramedullary rod 1139 is merely exemplary. Therefore, it will be understood that the support block 1102 and the associated cutting guide 1104 may be positioned relative to the tibia 14 in any appropriate manner.

As discussed above, the extramedullary rod 1139 may be positioned relative to the tibia 14 using any appropriate mechanism, such as the clamp 1162. Generally a user may affix the clamp 1162 relative to a selected portion of a patient's anatomy, such as near the ankle, to hold the extramedullary rod 1139 relative thereto. The extramedullary rod 1139 may include the holding portion 136 that interconnects with the support block 1102. The user may position the extramedullary rod 1134 in any appropriate manner, such as generally aligned with a tibia 14 or positioned at an angle thereto, depending upon the procedure. Regardless, the fastener 1136 allows for positioning of the support block 1102 near the tibia 14 through an incision, such as the incision 30, in the soft tissue 22. The incision 30 may be formed in any appropriate position relative to the tibia 14, such as a medial side of the tibia 14. It will be understood, however, that the incision 30 may be formed in any appropriate manner, depending upon a selected manner of performing a procedure relative to the tibia 14. Further, the incision 30 may include any appropriate dimension, such as a dimension of about 7 cm or more. Nevertheless, the incision 30 may be formed in any appropriate length according to selected procedures.

Therefore, the incision 30 allows for positioning of the support block 1102 relative to the tibia 14 using the extramedullary rod 1134 as an initial support member.

Further, the support member 1102 may include a length 1102' (see FIG. 16A) allowing it to pass through the incision 30 to be positioned relative to the tibia 14. The length of the support member 1102' may be any appropriate length, such as about 1 cm to about 10 cm. For example, the length 1102' may be about 3 cm.

Once the support member 1102 is positioned relative to the tibia 14, such as relative to a medial side 14*a* of the tibia 14, the stylus 1200 may be used to position the support member 1102 relative to a superior or proximal portion of the tibia 14. As discussed above, the stylus 1200 may be used to select a position for the support member 1102 relative to the superior surface of the tibia 14. Once positioned relative to the tibia 14 with the stylus 1200 the pins or other support members 1201 may be positioned to the bores 1138 to hold the support member 1102 relative to the tibia 14. The pins 1201 may allow for holding the support member 1102 relative to the tibia 14, when the extramedullary system 1139 is removed. Therefore, once the stylus 1200 is used to set the position of the support member 1102 relative to the tibia 14, the extramedullary rod system 1139 may be removed after the pins 1201 are used to hold the support member 1102 relative to the tibia 14.

Further, as discussed above, the cutting guide block 1104 may then be interconnected with the support member 1102 (FIG. 22). The cutting guide block 1104 may also include any selected length 1104' to allow it to pass through the selected incision 30. For example, the length of the movable cutting guide 1104 may be about 1 cm to about 5 cm, and may exemplary be about 4 cm. Further, the slot 1112 defined by the movable guide member 1104 may include a length that is less than or equal to the length the 1104' of the movable cutting guide 1104. Further, as discussed above, the slot 1112 defined by the movable cutting guide 1104 may include substantially straight, angled, or beveled edges to assist in guiding the saw blade 240.

The movable cutting guide 1104 that includes the groove 1108 is allowed to interact with the pin 1114 that may extend from a movable cutting guide 1104. Nevertheless, as discussed above, the support member 1102 may define the pin 1114 while the movable guide member 1104 defines the groove 1108 to allow for the movable guide member 1104 to move relative to the support member 1102. Further, other appropriate mechanisms may be allowed to movably interconnect the support member 1102 with the movable guide member 1104. Nevertheless, the movable guide member 1104 is generally able to move relative to the support member 1102 or the tibia 14 in any appropriate manner. Further, as discussed above, the dimension and orientation of the pin 1114 may allow the movable guide member to rotate relative to the support member 1102 or the tibia 14.

It will be understood that the movable guide member 1104 may be interconnected with any appropriate portion, and not necessarily the support member 1102. For example, the movable guide member 1104 may be interconnected with the tibia or the femur substantially directly. Further, the support member 1102 may be interconnected with the femur 12, such that the movable guide member 1104 may generally move relative to the support member 1102 interconnected with the femur 12. Regardless, the movable guide member 1104 is generally allowed to assist in guiding the saw blade 240 relative to the tibia 14 to resect a selected portion of the tibia 14.

The movable aspect of the cutting guide 1104 allows the cutting guide 1104 to be moved relative to the tibia 14 according to selected manners. For example, the movable cutting guide 1104 may be positioned relative to the tibia 14 at a generally anterior position relative to the tibia 14. This may allow for a first selected cut or resection portion to be made on the tibia 14 (FIG. 21A). The movable cutting guide 1104 may then be moved relative to the tibia 14 or the support member 1102 to a second position, such as generally medially, relative to the tibia 14 (FIG. 21B). In the second position, the movable guide member 1104 may allow for easy access to a different aspect of the tibia 14 not easily accessed and/or allowed from the first aspect. Therefore, the guide member 1104 may allow for the saw blade 240 to be substantially guided during the entire resection of the tibia 14.

Although it will be understood that the saw blade 240 may be moved relative the tibia 14 to insure a selected resection of the tibia 14, the movable cutting guide 1104 may allow for the saw blade 240 to be guided with the saw guide 1104 during a substantial portion over the resection of the tibia 14. Therefore, the movable guide member 1104 may allow for the selected resection to take place in a substantially guided manner. The guide member 1104 movements may allow for the formation of a virtual entire guide surface. That is a guide surface that spans the size of the resection to be performed or allows guiding of the saw 240 to make the resection. As discussed above the moveable guide member 1104 can be used to guide the saw 240 during the entire resection, even though the guide member 1104 may not include a dimension as large as the resection to be performed.

The movement of the movable guide block 1104 may be any appropriate movement, such as those discussed above. Therefore, the movable guide block 1104 may generally slide relative to the support member 1102 and also rotate relative to the support member 1102. Therefore, the movement of the movable guide member 1104 may be used by a user to guide the saw blade 240 in a selected manner. This may assist in reducing the necessity of a user's perception and free hand guiding of the saw blade 240 to perform a selected resection of the tibia 14.

Further, the movement of the movable guide member 1104 relative to support member 1102 and the tibia 14 allows for the movable guide member 1104 to be smaller than a selected dimension of the tibia 14, such as a width medial/lateral or a depth anterior/posterior of the tibia 14. Nevertheless, the movement of the guide member 1104 allows the saw blade 240 to be guided during a substantial portion of the resection due to the movement of the movable guide member 1104.

The movable guide member 1104 may be positioned easily through the incision 30. Providing the small or minimally invasive incision 30 may reduce trauma and a healing time for the patient after the resection of the tibia 14. The incision 30 may be formed at a selected length and the incision 30, or the edges thereof, may be moved with the movable guide member 1104 to form the resection of the tibia 14. Therefore, the incision 30 need not be large enough to expose the entire surface or area of the tibia 14 and may include a dimension to allow for positioning of the movable guide member 1104 relative to the tibia 14.

Nevertheless, the movable guide member 1104 may be used to guide the saw blade 240 to form the entire resection of the tibia 14 due to the movement of the movable guide member 1104 and the incision 30 may be moved with the movable guide member. Therefore, it will be understood that various retractors, guides, tissue pushers, and the like may be used when performing a procedure with the movable guide member 1104 and may be incorporated with the movable guide member 1104. Further, the space of the incision 30 and the size of the various members, such as the support member 1102 and the guide member 1104, may allow for reduced tension, movement, and the like of the soft tissue, relative to the tibia 14 and the femur 12. For example, the procedure may be performed relative to the tibia 14 while substantially eliminating or reducing the movement of the patella or the patellar tendon and substantially eliminating or reducing the need to evert or rotate the patella 20.

As discussed above, a cutting guide may rotate relative to various portions of the anatomy, such as the tibia 14. With reference to FIG. 25, a cutting guide 2500 may be positioned relative to the tibia 14, such that it substantially rotates and/or pivots relative to the tibia 14. The cutting guide may include any appropriate dimensions, such as one to allow it to be used with the incision 30. The cutting guide 2500 may include a longitudinal dimension of less than about 7 cm, and may exemplary include a dimension of about 4 cm.

The cutting guide 2500 may pivot about a pivot point 2502, such as a pin or member that may extend from an extramedullary rod 1134, or other appropriate member. For example, the cutting guide 2500 may interconnect with the support block 1102 so that the cutting guide 2500 may both rotate and slide relative to the support member 1102. Regardless, the cutting block 2500 may rotate generally in the direction of arrow 2500A relative to the tibia 14.

The saw blade 240 may pass through the rotating cutting guide 2500 through any appropriate portion, such as a slot, guide surface, or the like defined by the rotating cutting guide 2500. It will be understood that the saw blade 240 may be substantially equivalent to a dimension, such as a width of 2500' of the cutting guide 2500. Therefore, the cutting guide 2500 may be substantially small relative to the tibia 14. For example, the dimension 2500' may be about 1 cm to about 2 cm.

The rotation of the cutting guide 2500 may allow the saw 240, or a portion thereof, to move over substantially the entire surface of the tibia 14. The cutting guide 2500 may allow this without substantially translating the cutting guide 2500 medially/laterally or anteriorly/posteriorly, relative to the tibia 14, but generally through rotation alone. The cutting guide 2500 may rotate generally in the direction of arrow 2500A to allow movement of the saw blade 240 relative to the tibia 14. Further, the saw blade may move relative to the guide 2500, such as generally along the length of the saw blade 240 to resect various portions of the tibia 14. Thus, the tibia 14 may be resected without translating the cutting guide 2500 other than rotating the cutting guide 2500 and moving the saw 240. Therefore, the cutting guide 2500 may include a substantially small size to allow it to pass easily through the incision 30 or other appropriate portions.

The cutting guide 2500 may be positioned relative to the tibia 14 in any appropriate manner. For example, the cutting guide 2500 may be positioned relative to the support member 1102 and held in a selected position therewith. Therefore, it will be understood that the cutting guide 2500 may be positioned relative to the tibia 14 in any appropriate manner, such as those described above. Regardless, the cutting guide 2500 may rotate relative to the tibia 14 to allow for guiding the saw 240 generally over the entire area to be cut of the tibia 14. Again, this may be useful in reducing the need to view the entire area of the tibia 14 to be resected and ease the performance of a tibial resection.

Figure 28:
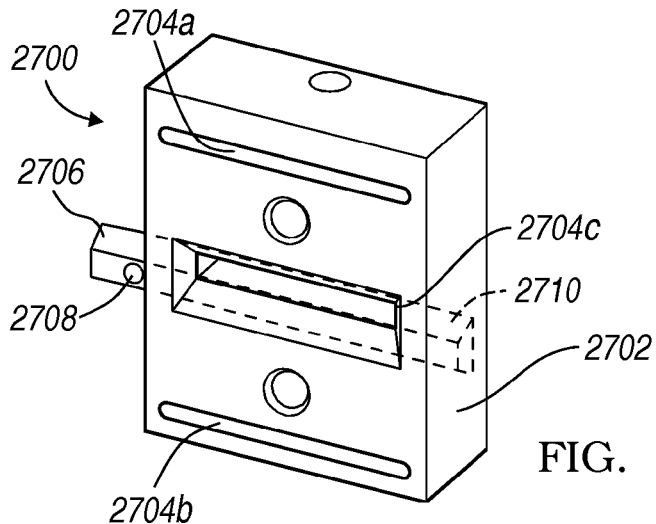
FIG. 28 is a perspective view of a moveable resection guide according to various embodiments.
Figure 26:
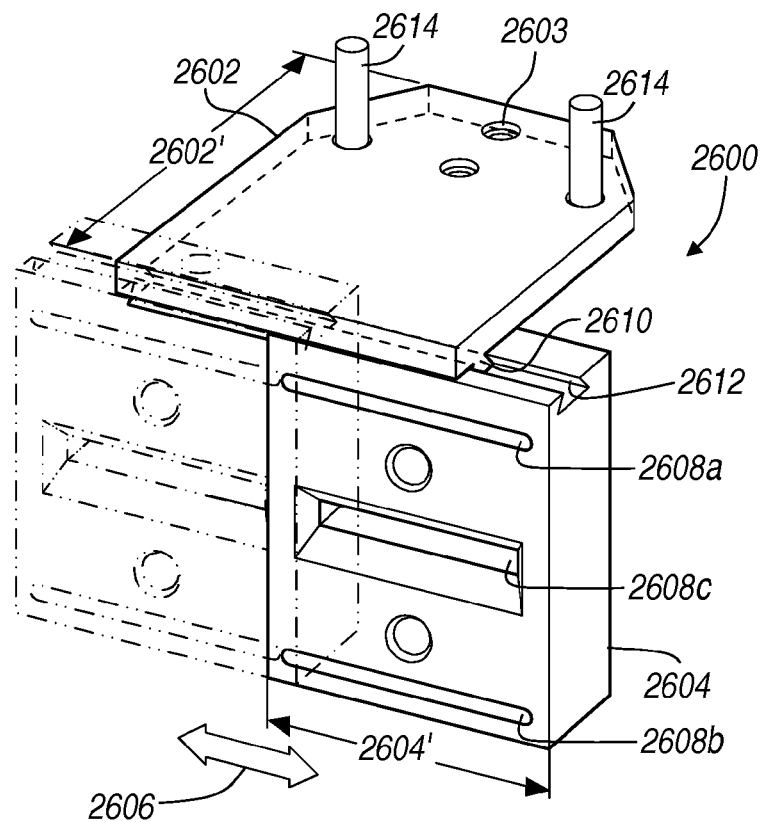
FIG. 26 is an exploded perspective view of a moveable resection guide according to various embodiments.

With reference to FIG. 26, a femoral cutting guide assembly 2600 according to various embodiments is illustrated. The cutting guide assembly 2600 generally includes a reference tab or flange 2602 and a cutting guide member 2604. The cutting guide member 2604 is generally able to move relative to the flange 2602 in the direction of arrow 2606. The cutting guide assembly 2600 is generally able to be mounted relative to the femur 12 to translate generally medially/laterally in the direction of arrow 2606, relative to the femur 12 (FIG. 28). The cutting block 2604 includes one or more guide surfaces or slots 2608. The guide slots 2608 may be used to guide a saw, such that the saw 240, relative to the femur 12. The resection of the femur 12 may be according to any appropriate mechanism, such as those described above and herein.

The flange 2602 includes a first rail or bar member 2610 that is operable to interconnect with a channel 2612 in the guide member 2604. It will be understood that the bar member 2610 may extend from the guide member 2604, while the track 2612 is defined by the flange 2602. Further, various other mechanisms, such as those described above, include the "T" or dovetail interconnection that allows for movement of the guide block 2604 relative to the flange 2602.

The flange 2602 may be fixed relative to any appropriate portion of the anatomy, such as the femur 12. For example, pins or locking members 2614 may be used to interconnect the flange 2602 with the femur 12 according to any appropriate mechanism. It will be understood that the pins 2614 may be passed through any appropriate portion of the flange 2602 to interconnect the flange 2602 with the femur 12. Further, the pins 2614 may be positioned on the flange 2602 in any appropriate location, such that the pins 2614 do not interfere with the resection guided with the guide block 2604.

The guide block 2604 may be similar to the guide block 160 discussed above. The guide block 2604, however, may include a posterior resection slot 2608a, an anterior resection slot 2608b and a chamfer cut slot 2608c. It will be understood that the chamfer cut slot 2608c may be used to form both anterior and posterior chamfer cuts. The cuts used to resect the femur 12 may be similar to those cuts generally known in the art to prepare a femur for a total knee replacement or replacement of the condyle portions of the femur. Therefore, one skilled in the art will understand that the guide block 2604 may be formed in any appropriate manner to form selected resection portions of the femur 12. Regardless, the guide block 2604 may move relative to the flange 2602, such that the guide slots 2608 may be moved and effectively span the area to be resected on the femur 12. Therefore, the guide slots 2608 need not be the entire size or dimension of a resection, such as a width of a resection, but may be moved, such that the saw 240 is guided along the guide slot 2608, substantially during the entire resection.

The guide member 2604 may include any appropriate dimension, such as a dimension 2604'. The dimension 2604' may be any appropriate size, such as above 1 cm to about 8 cm. For example, the dimension 2604' may be about 4 cm. The dimension 2604' may allow for the resection assembly 2600 to be positioned relative to the femur 12 through the incision 30 that may be a substantially small or minimally invasive incision. Rather than providing an incision that allows for complete access to an entire knee portion 10, the incision 30 may be moved with the resection guide 2604 as the guide member 2604 moves via the track assembly 2610, 2612 relative to the flange 2602.

Figure 27:
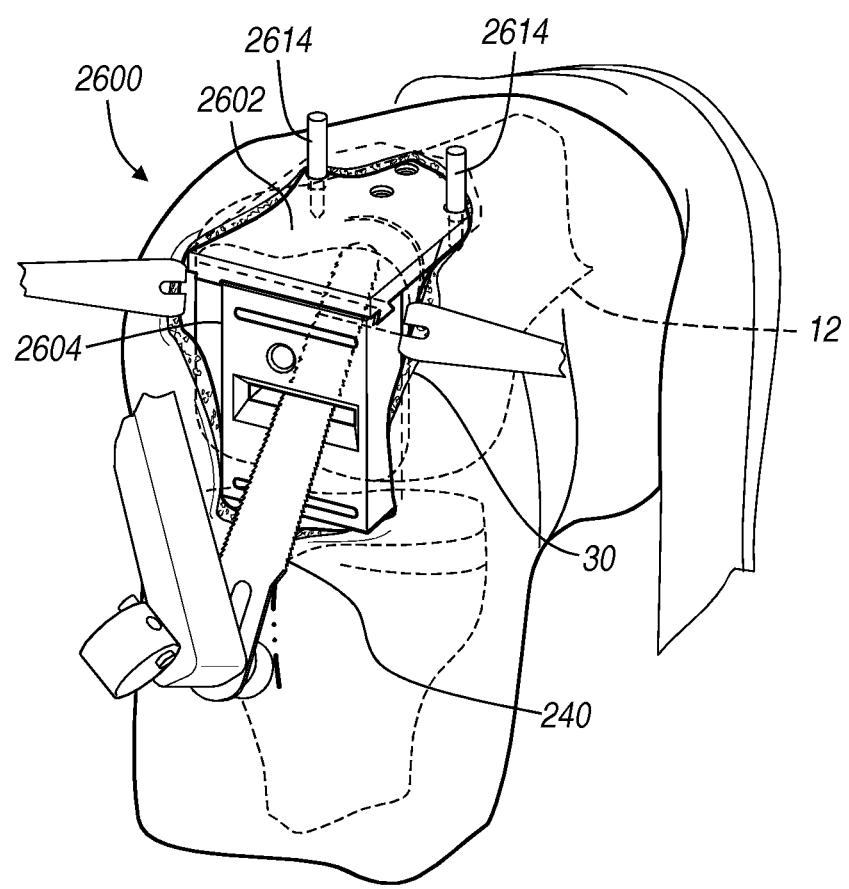
FIG. 27 is a detail environmental view of the moveable resection guide of FIG. 26.

With further reference to FIG. 27, the resection assembly 2600 may be positioned through the incision 30 relative to the femur 12. The incision 30 may be formed in the knee 10 of the patient and the resection guide assembly 2600 positioned relative to the femur 12 in any appropriate manner. For example, the flange 2602 may be positioned relative to the femur 12 using any appropriate sizing or positioning mechanism. For example, an IM rod or other appropriate mechanism, such as those described above or generally known in the art, may be used to assist in positioning the flange 2602 relative to the femur 12. Regardless, the flange 2602 provides a mechanism to allow the guide member 2604 may move relative to the femur 12.

As illustrated in FIG. 27, the guide member 2604 may be positioned relative to the femur 12 and the saw 240 passed through a selected slot 2608 with the guide member 2604 to perform a resection of the femur 12. The various resections may include those described above or generally known in the art for resecting the femur 12. Further, once a portion of the resection is performed, the guide member 2604 may be moved medially or laterally relative to the femur 12 to perform or continue the resection of the femur 12. In this way, the guide member 2604 may be used to guide the saw 240 during a substantial portion of the resection of the femur.

As discussed above, the resection assembly 2600 may be used to guide the saw 240 relative to the femur 12. Because the guide member 2604 may be moved relative to the femur 12, such as with the flange 2602, the guide member 2604 can be less than a dimension of the femur. For example, the dimension 2604' may be less than a medial/lateral distance between epicondyles, yet the entire resection of the femur may be guided with the guide member 2604. As discussed above, the sliding or moving guide blocks may be positioned relative to various portions of the anatomy, such as the femur 12 or the tibia 14, through generally small or minimally invasive incisions. Regardless of the size of the guide block, such as the guide block 2604, or the incision, the guide block 2604, or any appropriate guide block according to various embodiments, may be used to guide a substantially complete resection without including a guide slot or surface the is substantially equivalent to the resected dimension. Therefore, the guide block 2604 may be positioned relative to the femur 12 and used to resect the femur 12 without providing the guide block 2604 to be a substantially large or equivalent to the resection size.

Further, the flange 2602 may include any appropriate dimension. For example, the flange may include a length or depth dimension 2602' that is long enough or great enough to allow positioning a pin 2614, such that it may not interfere with the resections or cuts formed with the block 2604. In positioning the flange 2602 relative to the femur 12 positioning of the pins 2614 relative to the cutting block 2604 and the femur 12 may be taken into account. The flange 2602 may include a plurality of bores 2603 that may allow for passing the pins 2614 therethrough, such that they may interconnect the flange 2602 with the femur 12. Therefore during the procedure, a user may select the position of the pins 2614 relative to the femur 12 using the flange 2602 to position the pins 2614. It will be understood that any appropriate holding or locking mechanism may be provided to hold the flange 2602 relative to the femur 12 during the resection of the femur 12 and the movement of the guide block 2604 and the pins 2614 are merely exemplary.

With reference to FIG. 28, a moveable cutting guide 2700, according to various embodiments is illustrated. The moveable cutting guide 2700 includes a guide block 2702 that includes a plurality of guide surfaces 2704. The guide surfaces may include an anterior guide slot 2704a, a posterior guide slot 2704b, and a chamfer guide slot 2704c. As discussed above the chamfer guide slot 2704c may be used to form both anterior and posterior chamfer cuts. The cutting guide 2700 may include a dimension 2700' that is any appropriate dimension. The dimension 2700' may be about 2 to about 8 cm, and may exemplary be about 4 cm.

The guide block 2702 may move relative to a rail 2706. The rail may be held relative to a portion of the anatomy, such as the femur 12, with a pin 2708. The rail 2706 may be modularly connected with the cutting block 2702, such that the rail 2706 can be first positioned on the femur 12 by itself or separately. The cutting block 2702 can then be coupled to the rail 2706, after the rail 2706 is attached to the bone. It will be understood that the rail 2702 may be pre-assembled with and non-removably coupled to the cutting block 2702. The rail 2706 may be also defined by the block 2702 and a member defining a groove affixed to a portion of the anatomy. The block 2702, however, may define a groove 2710 to interact with the rail 2706. The groove 2710 and the rail 2706 may be designed to cooperate with the chamfer guide slot 2706c to create a clearance therefore. The rail 2706 may also be any appropriate dimension, such as within or of equivalent size to the cutting guide 2700.

The moveable guide assembly may be fixed to a distal portion of the femur, similar to the guide block in FIG. 10B. The rail 2706 may be formed to extend the entire width of the femur 12 or only a portion thereof. As the guide block 2702 defines the guide slots 2704 the rail 2706 may be positioned in a single position and the block 2702 moved to move the guide slots 2704 relative to the femur 12. In this way the resection of the femur 12 may be guided with the block 2702 for a substantial portion or all of the resection. This can be done even though the guide block 2702 or the guide slots 2704 alone are not the dimension, such as a width, of the entire resection to be performed.

Therefore, it will be understood, according to various embodiments, that the resection of the femur 12 or the resection of the tibia 14, or any appropriate resection, may be performed using various instruments. As described herein and above, the various guide members may move relative to the portions to be resected, such that the guide member need not include a dimension that is substantially equivalent or greater than the area to be resected. Rather the guide member may move, either translate generally in a straight line, rotate around a point, move in a curved path, or move in any other appropriate dimension, to allow for guiding of a cut member, such as a saw blade, relative to the member to be resected. This allows for generally physically or substantially guiding the cut member during the entire resection procedure, thereby minimizing the amount of freehand or unguided resection to be performed.

The guide member is able to move during the resection to be performed. Either the guide member may be moved to a selected position and locked for a portion of the resection or may move freely during the resection. Regardless, the guide member, according to various embodiments, is able to define a virtual or constructive guide surface that is larger than the physical dimension of the guide member or guide surface itself. The constructive guide surface allows the user to guide an instrument during an entire resection, however, rather than only a portion thereof regardless of the size of the guide member. The constructive guide surface may be equal to, smaller than, or larger than a selected dimension of the resection as well. For example movement of the cutting guide may define a constructive guide surface smaller than a dimension of a selected resection, but movement of the guide instrument in the guide area allows for a resection of a selected dimension.

Figure 29:
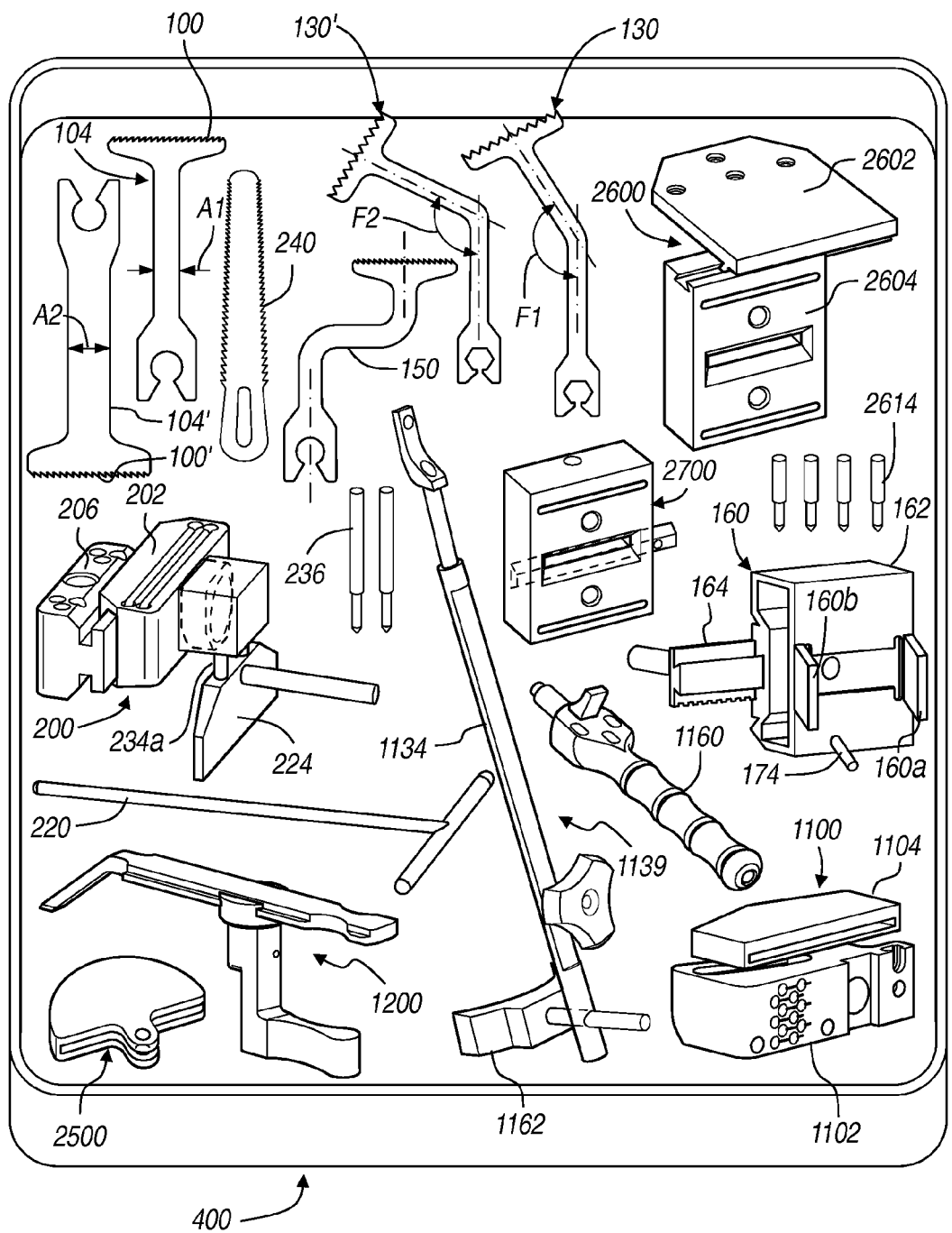
FIG. 29 is a perspective view of a kit including various saw blades and cutting block assemblies.

With reference to FIG. 29, a kit 400 includes a plurality of the saw blades 100 and 130 and the translating cutting block assembly 160 and/or 200. The kit 400, for example, may include a first narrow cutting saw 100 and a second narrow cutting saw 100'. The first narrow cutting saw 100 may include a neck 104, which includes a width $A_1$. The width $A_1$ can be any selected width to be used in a resection procedure. The kit 400 may also include a second narrow saw 100', which has a neck 104', and includes a second width $A_2$. The second width $A_2$ may be greater than the width $A_1$ of the first narrow saw blade 100. Therefore, the physician may select the desired narrow saw blade, 100 or 100', depending upon the specific procedure to be performed. For example, a larger incision may be used or necessary that may accept the larger width $A_2$ of the second narrow saw blade 100'. Nevertheless, a selection is left to the user depending upon the desires or necessity.

Similarly, the kit 400 may include a first angled saw blade 130, that includes an angle $F_1$ of a longitudinal axis of the neck relative to the longitudinal axis of the tool engaging section. The kit 400 may also include a second angled saw blade 130', which includes a second angle $F_2$. The second angle $F_2$ may be greater or less than the first angle $F_1$. Therefore, the plurality of the angled saw blades 130 and 130', allows one to be selected depending upon the particular anatomy of the patient or desires of a physician. Moreover, the various angles can more easily reach various portions of the knee 10 without great effort or trauma to the soft tissue 22. For example, the first angle saw blade 130 may be used to resect a first portion of the knee 10 while the second angle saw blade 130' is used to resect a second portion of the knee 10. Therefore, both of the angled saw blades 130 and 130' can be used to resect the various portions of the knee 10. It will be understood that although only two exemplary saw blades for the narrow saw blade 100 and 100' and the angled saw blade 130 and 130' a larger plurality of the various saw blades may be provided in the kit 400.

Also provided in the kit 400 are the cutting block assemblies according to various embodiments. The kit 400 may include any or all of the guide assemblies. Thus the kit 400 may be provided to perform any appropriate procedure The guide assemblies may include the guide assemblies for femoral resection 160, 200, 2600, 2700 and those for tibial resections 1100 and 2500. Although it will be understood that the cutting guides according to various embodiments may be used to resect any appropriate portion. For example, the rotating cutting guide 2500 may be used to resect the femur or any appropriate boney portion. The cutting block assembly 160 includes the rail 164 and the cutting block 162. As described above, the cutting block 162 is able to translate on the rail 164 to resect the various portions of the anatomy. Also the cutting block 200 may be included. Also various sizes or the cutting guides may be provided in the kit 400. It will be understood, however, that the movement of the cutting guides, according to various embodiments, may allow for the provision of one cutting block for all or nearly all-possible patient sizes. The cutting guide assemblies, according to various embodiments, can be used in conjunction with the narrow saw blades 100 and 100' or other generally known saw blades. The cutting guide assemblies, according to various embodiments, can also be used in conjunction with the angled saw blades 130 and 130' if desired. Nevertheless, the resection kit 400 can be provided for use in a surgery. Therefore, during the operative procedure, the various saw blades can be selected and used by a physician in conjunction with cutting guide assemblies, according to various embodiments.

Further, the guide members according to various embodiments, such as the guide member 162, 200, 1100, and/or 2500 may be used alone or in combination while performing a selected procedure, such as a total knee arthroplasty. The moveable guide members can be used to form resections on various bone portions, such as those described above and herein. The various guide members to guide resections of the femur 12 and/or tibia 14 may include those described above and herein. Therefore, the various guides may be used in conjunction, should a surgeon desire to perform a substantially minimally invasive procedure to form a complete knee arthroplasty, or in a conventional open procedure. For example, the knee arthroplasty may be substantially unicondylar, bicondylar, or a complete knee arthroplasty. Further, a complete femoral component, that is one that is interconnected and replaces both condyles of the femur, may be used. Exemplary knee implants include the Maxim™ and the Ascent™ provided by Biomet, Inc. of Warsaw, Ind. Other femoral implants may include those described in U.S. patent application Ser. No. 10/770,870, filed Feb. 3, 2004, entitled "METHOD AND APPARATUS FOR PROVIDING SOFT TISSUE RETRACTION WHILE STABILIZING A CUTTING INSTRUMENT", incorporated herein by reference. Therefore, the various instruments may be used by a surgeon, should the surgeon desire to perform a substantially minimally or less invasive procedure through an incision, such as the incision 30, relative to the knee of a patient.

Figure 33:
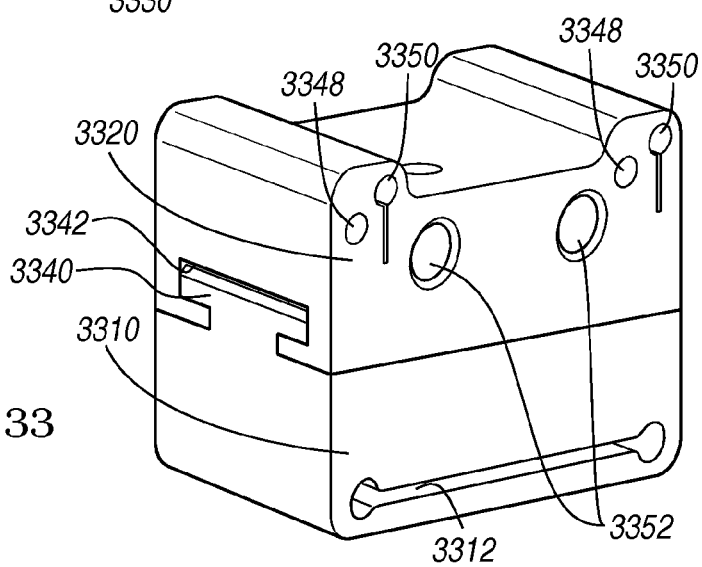
FIG. 33 is a perspective view of the cutting device of FIG. 32, shown without an alignment guide.
Figure 34:
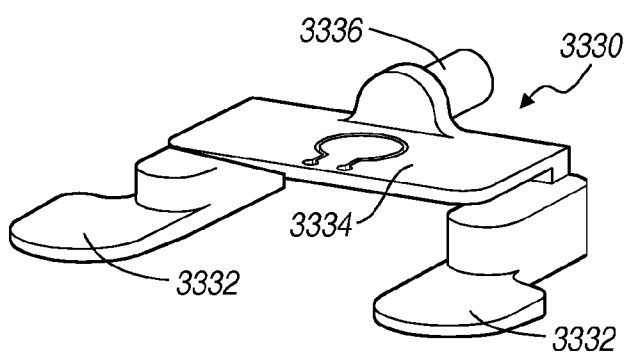
FIG. 34 is a perspective view of an alignment guide for the cutting device of FIG. 32.
Figure 35:
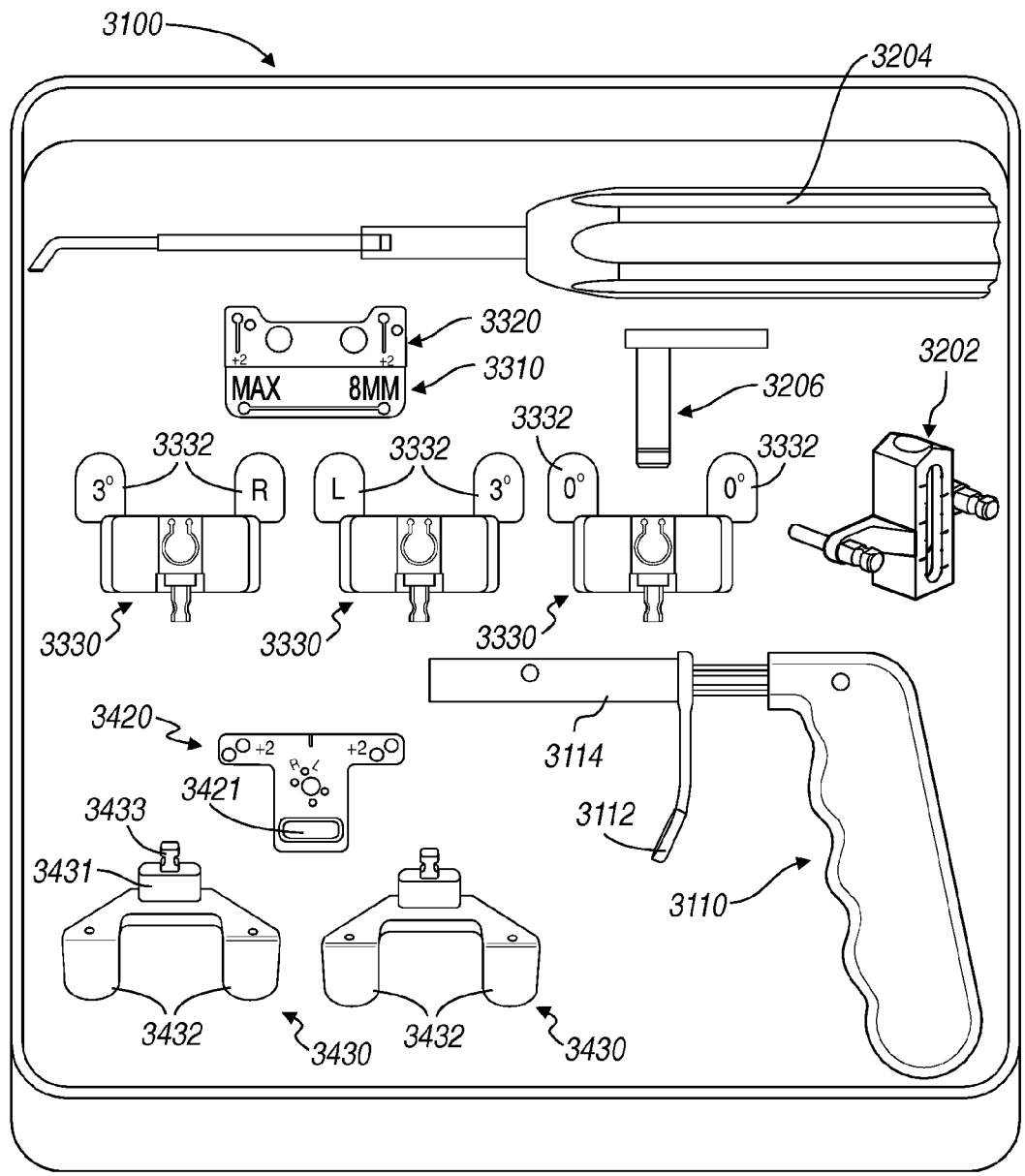
FIG. 35 illustrates a kit of surgical components according to the present teachings.

Referring to FIGS. 30-35, other related modular instrumentation and surgical components can be used according to the present teachings to provide an exemplary surgical kit 3100 illustrated in FIG. 35. The components can also be combined to provide various assembled instruments, including exemplary modular sizing devices 3200, 3200' illustrated in FIGS. 30 and 31A, and an exemplary modular cutting device 3300 illustrated in FIG. 32. The various components of the kit 3100, as well as various instruments that can be assembled from the kit 3100, including, for example, the sizing device 3200 or 3200' and the cutting device 3300, can have streamlined profiles with reduced dimensions to accommodate the confines of small incisions, should it be desired by the surgeon, as may be practiced in minimally invasive procedures.

Figure 30:
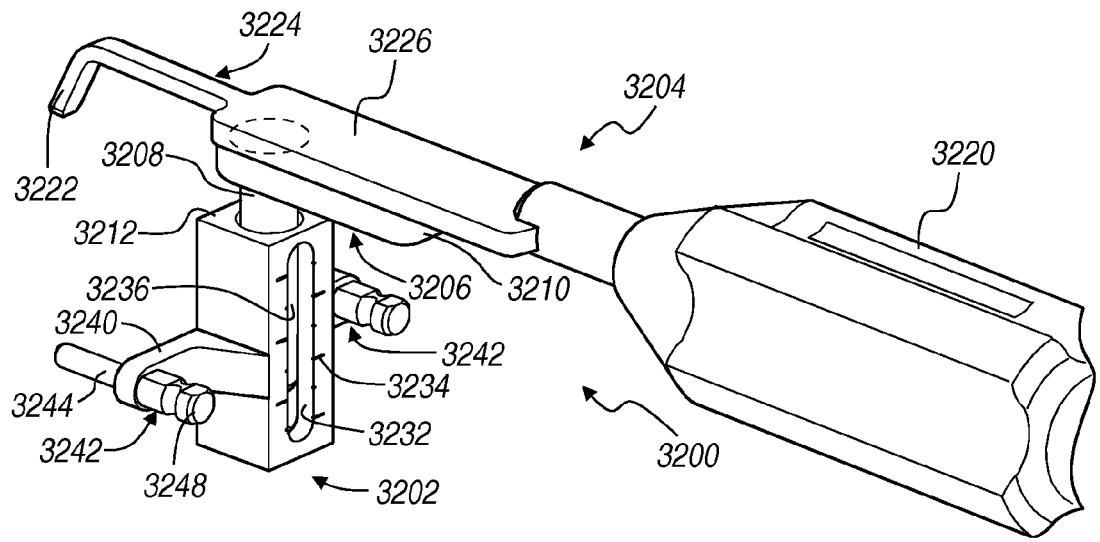
FIG. 30 is a perspective view of a modular sizing device according to the present teachings.
Figure 31:
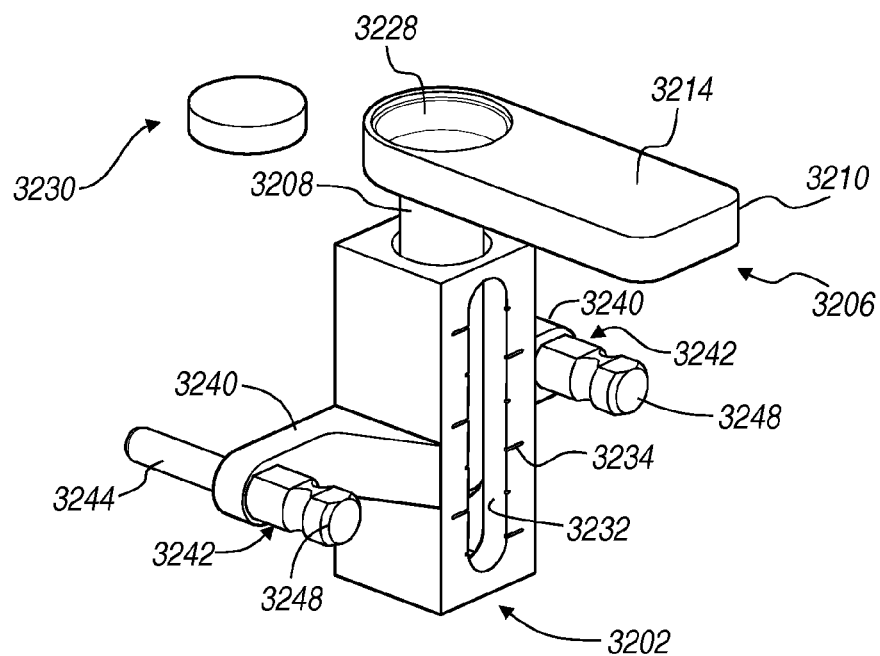
FIG. 31 is a perspective view of the sizing device of FIG. 30, shown without a stylus.
Figure 31A:
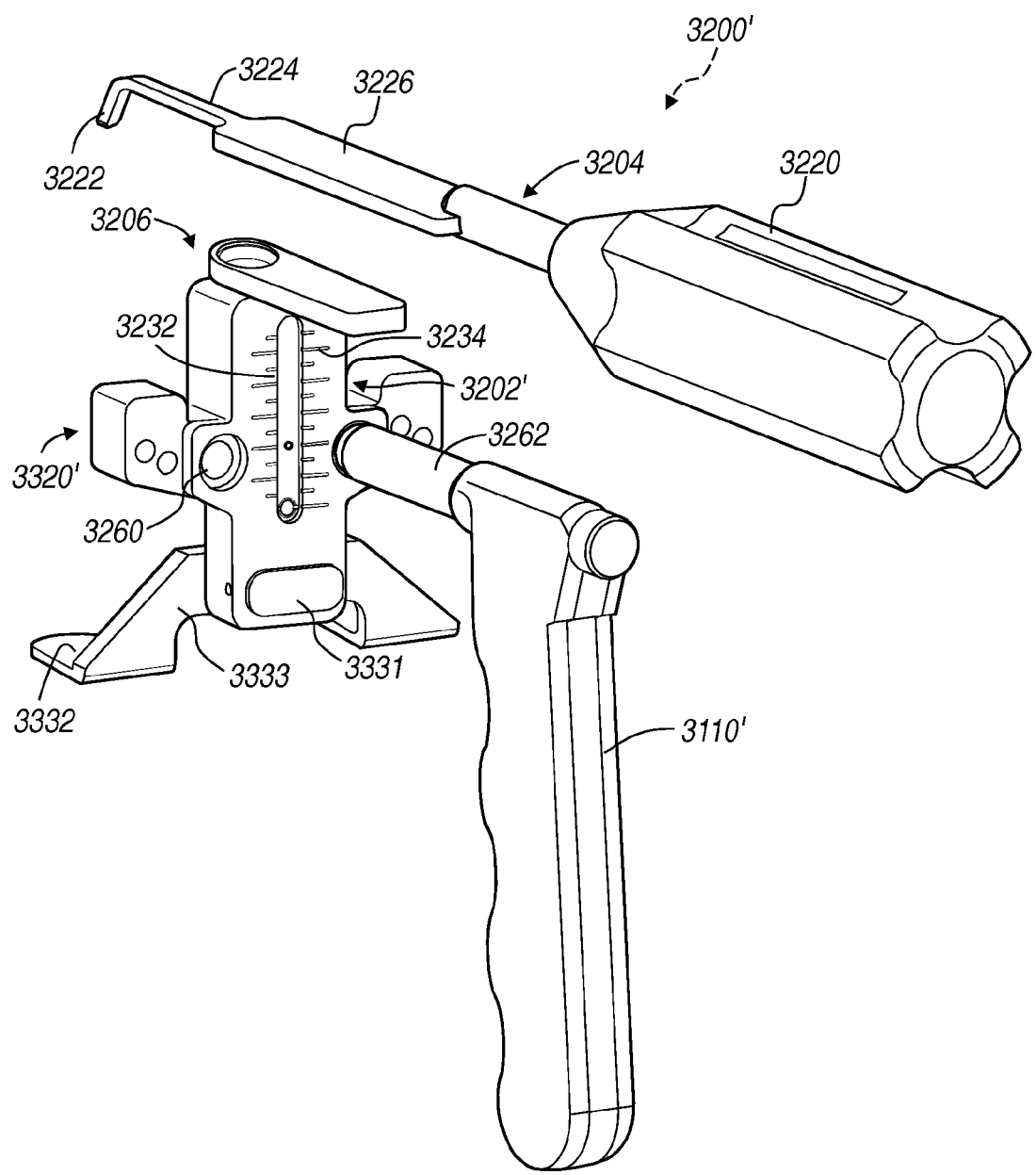
FIG. 31A is a perspective view of a modular sizing device according to the present teachings.

Referring to FIGS. 30, 31 and 31A, each the exemplary sizing devices 3200, 3200' includes modularly connected components, such as, respectively, a sizer base 3202 (or 3202'), a stylus 3204, and a coupler 3206 for connecting the sizer base 3202 to the stylus 3204. Each sizing device 3200, 3200' can be used, for example, as an anterior-posterior sizer for the distal femur in an exemplary knee procedure. The coupler 3206 can provide magnetic coupling between the sizer base 3202 (or 3202') and the stylus 3204, and is movable relative to the base 3202 (or 3202'). The stylus 3204 can include a handle 3220, a tip 3222, and a stylus arm 3224, extending from the handle 3220, to the tip 3222. A portion of the stylus arm 3224, can be a plate 3226 having planar surfaces, and can be made from magnet-attracting material, such as, for example, ferromagnetic material. The coupler 3206 can include a leg 3208 and an arm 3210. The leg 3208 can be a cylindrical rod slidably received in a bore 3212 of the sizer base 3202. The coupler arm 3210 can be a plate having a planar surface 3214 that can support the plate 3226 of the stylus arm 3224. Magnetic coupling can be provided by using a magnetic member or portion 3230. For example, the magnetic member 3230 can be a separate magnet that is received in a cavity 3228 of the coupler 3206. The coupler 3206 can be conveniently made as an integral piece of substantially L- or T-shape. The coupler 3206 can also be modular, combining a separate rod that defines the coupler leg 3208, and a separate plate that defines the coupler arm 3210. The arm 3210 can include a hole that receives a portion of the leg 3208 and also defines the cavity 3228 for the magnetic member 3230. The coupler leg 3208 can also be connected to the coupler arm 3210 with a Morse taper connection. Alternatively, instead of using a separate magnetic member 3230, a portion of the coupler arm 3210 can be magnetic. The magnetic member 3230 interacts with magnet-attracting portion 3226 of the stylus arm 3224 to connect the stylus 304 to the sizer base 3202.

Each sizer base 3202, 3202' can include an open slot 3232 and a calibrated scale 3234 adjacent to the slot 3232. The position of an index or mark 3236 on the leg 3208 of the coupler 3206 relative to the scale 3234 can be used for size measurement when the tip 3222 of the stylus 3204 is in contact with a bone surface. Referring to FIG. 31, the sizer base 3202 can include two extensions 3240 that are configured to receive posts 3242, such as bolts. The posts 3242 can include a shaft 3244 and a head or ball 3248 that can be gripped using a quick-release pistol-grip handle 3110, such as the one illustrated in FIG. 35. The quick release handle 3110 includes a spring-loaded trigger 3112 and a ball bearing (not shown) inside a barrel 3114 for gripping the head post 3242. Referring to FIG. 31A, the sizer base 3202' can include a foot component 3333 having a pair of feet 3332 configured to be received under the posterior condyles. The foot component 3333 can be integral to the sizer base 3202' or modularly coupled to the sizer base 3202', such as, for example, by an extension/slot coupling. In the illustrative example of FIG. 31A, the extension 3331 is attached to the foot component 3333, and is received in a slot 3335 of the sizer base 3202', although the converse (extension 3331 attached to the base 3202' and slot 3335 defined in the foot component 3333) or other coupling arrangements can be used.

The sizer base 3202' can also include a rail or drill guide 3320' integrally or modularly coupled thereto. The drill guide 3320' can be first attached to the bone with pins, and the sizer base 3202' can be coupled to the drill guide 3320' afterwards. The sizer base 3202' can further include an aperture 3260 for engaging a quick-release handle 3110'. The quick release handle 3110' is coupled to a spring loaded plunger 3262 for locking a plunger ball (not shown) with the aperture 3260.

Figure 32:
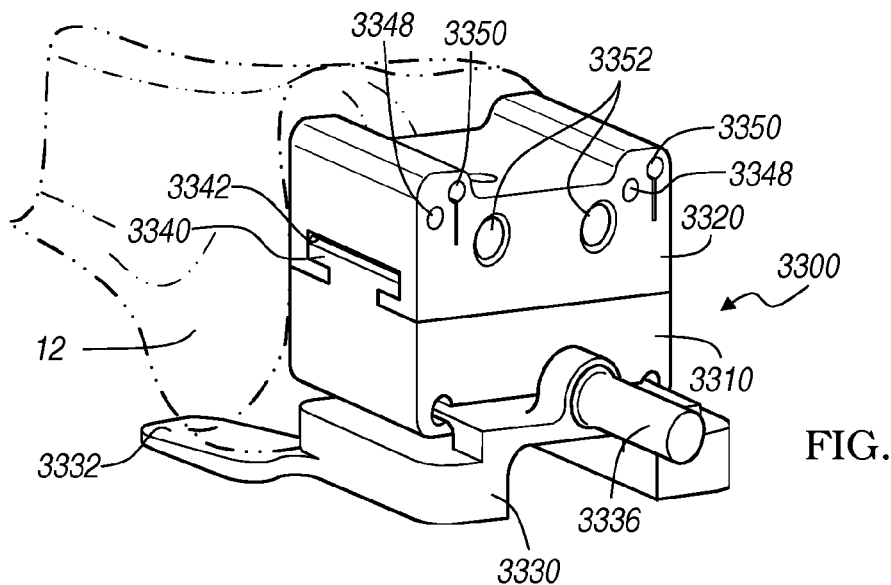
FIG. 32 is an environmental perspective view of a modular cutting device according to the present teachings.

Referring to FIGS. 32-34, the exemplary cutting device 3300 can include various modularly coupled components, including a cutting block 3310, a drill guide 3320, and an alignment guide 3330. The cutting block 3310 defines a cutting slot 3312 for receiving a saw blade or other appropriate resection tool. The drill guide 3320 can be slidably coupled to the cutting block 3310, using for example, a T-connection, as illustrated in FIG. 32, for sliding in the medial-lateral direction relative to the bone, such as, for example, the distal femur for an exemplary knee procedure. The T-connection can be defined by a T-shaped boss 3340 and a mating T-shaped slot 3342. The T-shaped slot 3342 can be defined either on the drill guide 3320, as shown in FIG. 32, or on the cutting block 3310, and the T-shaped boss 3340 can be correspondingly defined on the mating component. The drill guide 3320 can include one or more pairs of drill holes 3348, 3350. The drill guide can also include apertures 3352 for receiving a positioning/carrying handle (not shown).

Referring to FIG. 34, the exemplary alignment guide 3330 can include a pair of feet 3332 configured to be received under the posterior condyles of the femur for alignment therewith, a flange 3334 and a post 3336. The flange 3334 is configured to be received into the cutting slot 3312 of the cutting block 3310 for positioning, alignment and drilling procedures. The feet 3332 can be configured with neutral or three 3° (left or right) angle, as illustrated in FIG. 35. The alignment guide 3330 is removed before cutting, leaving the cutting slot 3312 available to receive a cutting blade for an optional posterior cut.

It will be appreciated that although the exemplary sizing device 3200 and cutting device 3300 can be used together in one procedure, each can also be used as an independently-used device. Additionally, the sizing device 3200 can be used without the cutting device 3300, or in conjunction with a second, stand-alone drill guide 3420 and a second, stand-alone alignment guide 3430 having feet 3432, both illustrated in FIG. 35. The stand-alone drill guide 3420 includes a slot 3421 that can engage with a peg 3431 of the stand-alone alignment guide 3430. A post 3436 extends from the peg 3431 and is adapted to engage with the barrel 3114 of the pistol-grip handle 3110 for quick release.

With continued reference to FIG. 35, the alignment guide 3330 can be provided in different sizes and configurations for the left and right knees, having, for example, feet that are neutral or at about 3° angle. Similarly, the second alignment guide 3430 can be provided in different sizes and configurations for the left and right knee, and can also be used in unicondylar mode. Accordingly, the instrumentation of the kit 3100, provides the surgeon with an assortment of components from which to pick and choose for assembling an appropriate instrument for sizing, aligning or cutting in connection with knee or other surgical procedures. The modularity of the instrumentation and the compact size of the various components coupled with the provided ergonomic and quick release handles 3110 can be advantageous use for minimally invasive procedures or in conventional open procedures.

Figure 36:
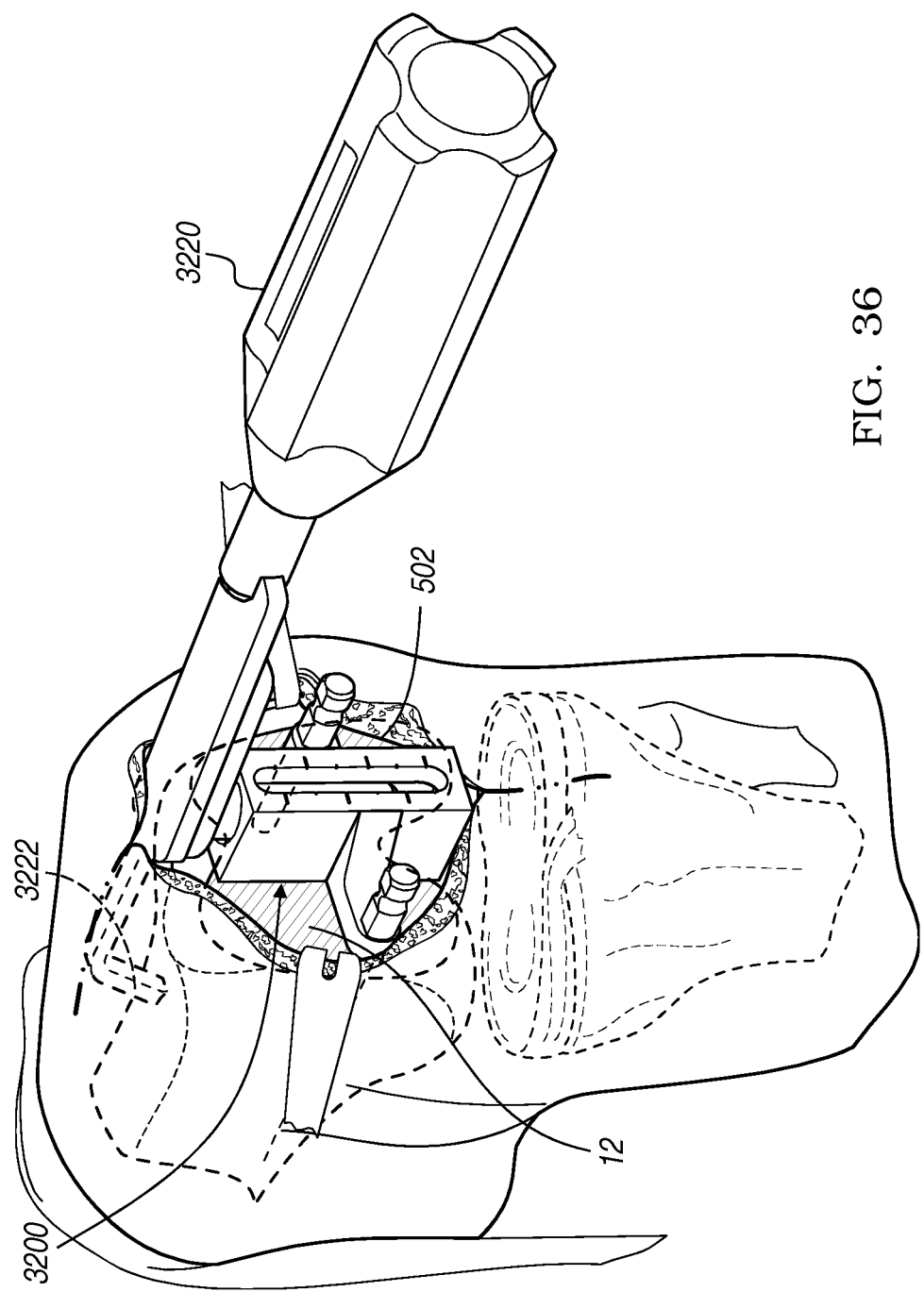
FIG. 36 is an environmental view of the sizing device of FIG. 30, shown during a surgical procedure.

Referring to FIG. 36, in an exemplary knee procedure, the sizing device 3200 can be placed flush with the distal femur 12, which has been exposed through a small incision 502. Using the handle 3220 of the stylus 3204, the tip 3222 is moved along the anterior femoral surface to determine the appropriate size. Drill holes can be prepared using the alignment guide 3430 with the feet 3432 under one or both condyles of the distal femur and attaching the drill guide 3420 to the second alignment guide 3430 as described above for quick release.

The cutting device 3300 can be used as illustrated in FIG. 32. The cutting block 3310 with the drill guide 3320 assembled thereon can be positioned flush against the distal femur 12. The flange 3334 of the alignment guide 3330 can be inserted into the cutting slot 3312 and the feet 3332 can be positioned under the femoral condyles. The drill guide 3320 can be slid in the medial-lateral direction, as needed, for placing the drill holes 3348, 3350 in appropriate position, approximately near the center of the distal femur 12, for inserting drill pins into the bone. The alignment guide 3330 can then be removed, and femoral resection can be performed using a resection blade through the cutting slot 3312. The cutting block 3310 can be slid relative to the drill guide 3320 during the cutting operation to expand the sweep of the saw.

Figure 37:
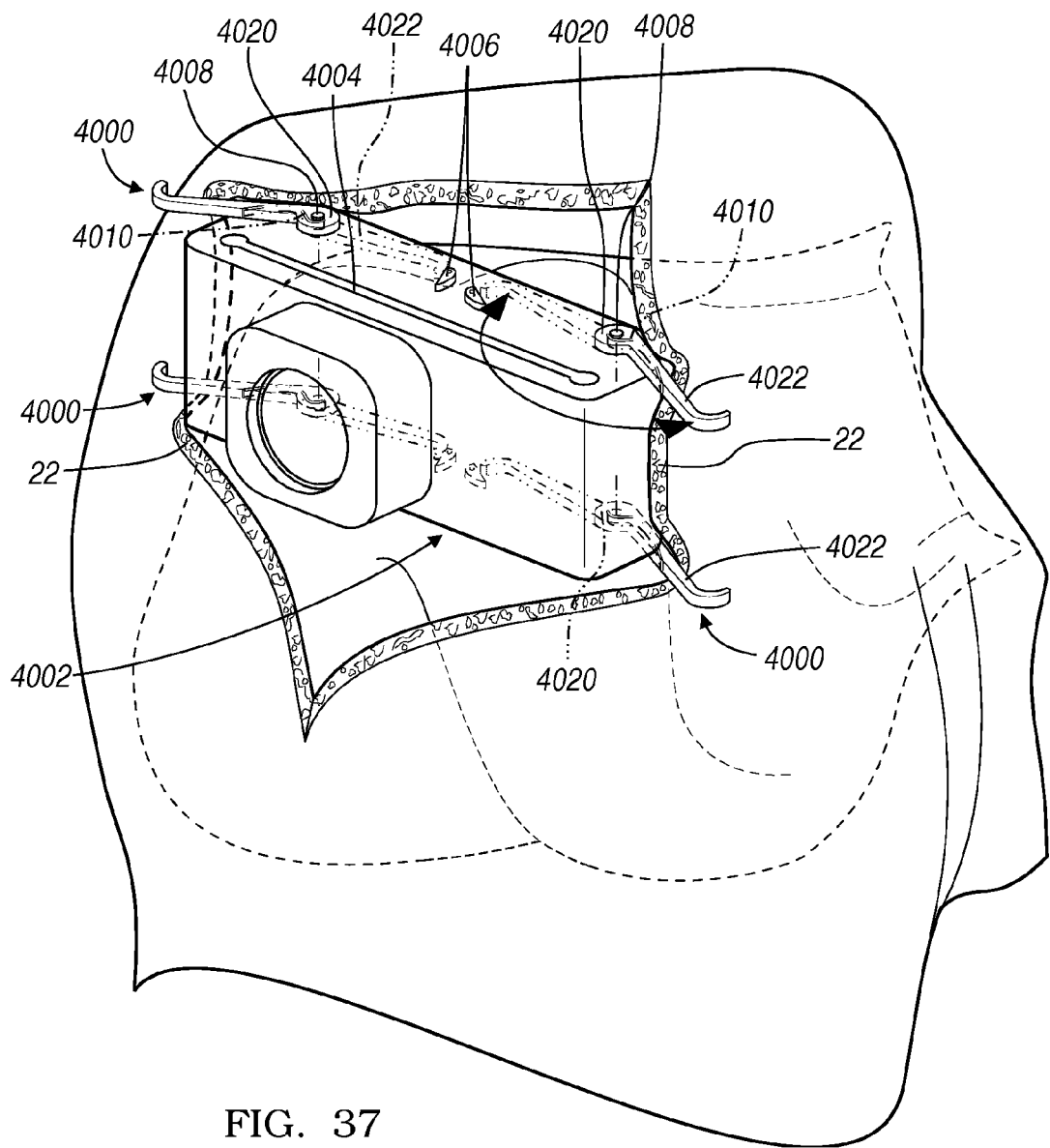
FIG. 37 is a perspective view of soft tissue retractor according to the present teachings shown coupled with a cutting guide.

Referring to FIG. 37, an exemplary soft tissue retractor 4000 according to the present teachings can be coupled with a surgical instrument 4002, such as, for example, a cutting guide having a cutting slot 4004. The retractor 4000 can be permanently, removably or modularly coupled to the instrument 4002 with fasteners or other coupling devices 4008 known in the art, such that the retractor 4000 can move between deployed and storage positions. The retractor 4000 can include an attachment portion 4020 rotatably coupling the retractor 4000 to the instrument 4002, and at least one elongated or finger-like portion 4022 for pushing soft tissue 22 away from the cutting slot 4004. The retractor 4000 can be spring biased by a spring or other biaser 4010 in the deployed (extended) position for pushing away soft tissue 22. A retainer 4006, such as, for example, a hook, a lever or other retaining device, can be attached to the instrument 4002 to retain the retractor 4000 in the storage position. It will be appreciated that additional retractors 4000 may be added, as desired, for particular instruments 4002 or surgical procedures.

The retractor 4000 can be built-in at the time of manufacture of the instrument 4002 or can be retrofitted to the instrument 4002 at a later date. With the retractor 4000 attached to the instrument 4002 and available for deployment as needed, the possibility of trauma to soft tissue 22 can be reduced. Coupling the retractor 4000 to the instrument 4002 provides a compact design that can be used in procedures involving small incisions, as well as other procedures. The compact design can reduce the number of separate instruments in the wound area, possibly reducing the possibility of mishaps or the necessity for additional assistants providing retractors to the surgeon or operating such instruments to keep soft tissue 22 from the wound site.

The resection of the femur 12, or any appropriate bone, can be performed using a resection guide according to various embodiments. It will be understood that any appropriate resection guide may be used and may be selected for various purposes, such as the patient's anatomy, preferences of a user, patient requirements, or any appropriate purpose. Nevertheless, as discussed above, the various embodiments of a resection guide can include various features such as moveable portions, fixed portions, holding portions, or the like. It will be understood, that the resection guide, according to any appropriate embodiment, can be used.

Figure 38:
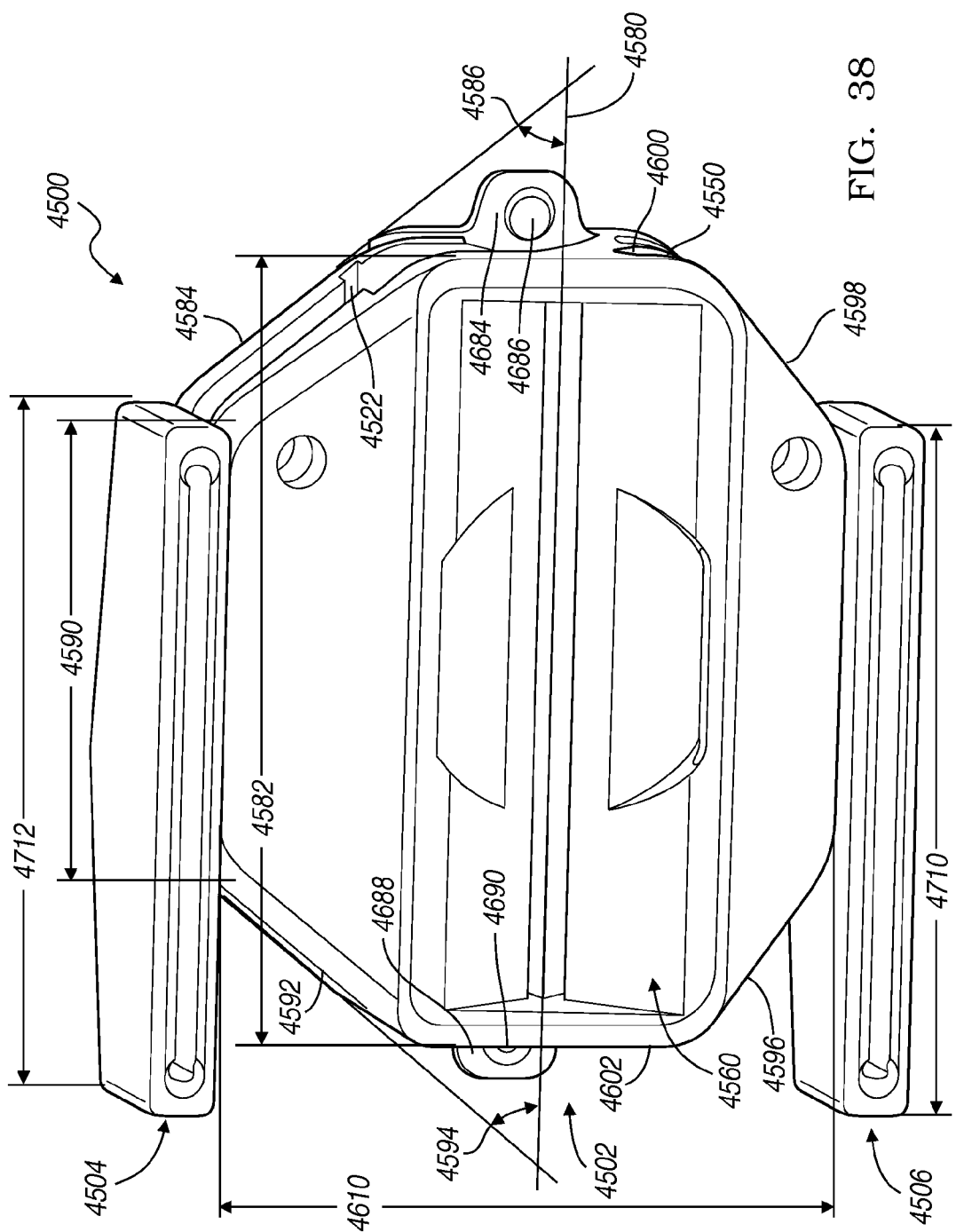
FIG. 38 is a front plan view of a guide apparatus.
Figure 39:
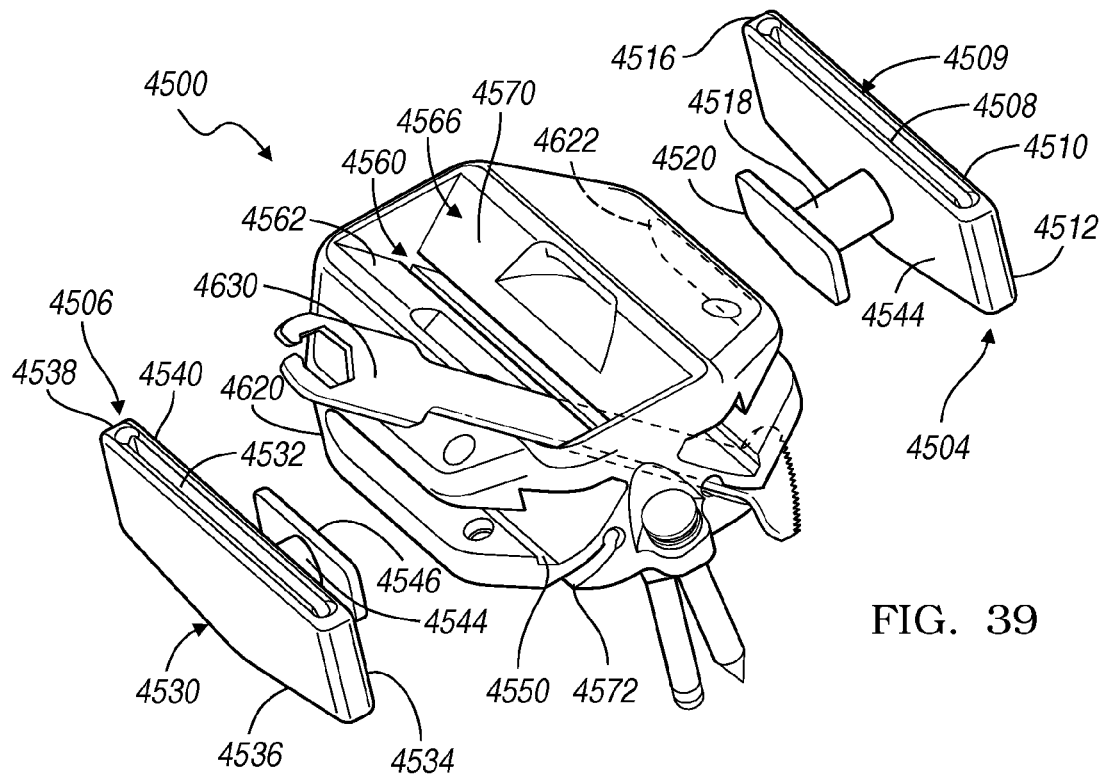
FIG. 39 is a front exploded perspective view of a guide apparatus according to various embodiments.
Figure 40:
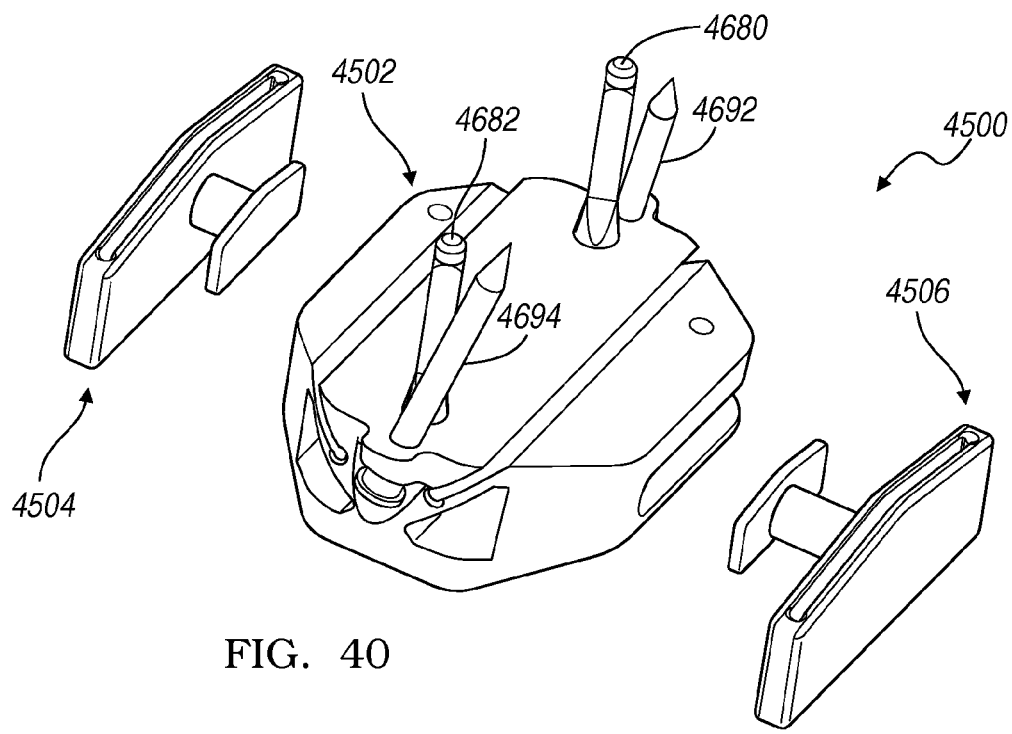
FIG. 40 is a back perspective exploded view of a guide apparatus according to various embodiments.

For example, with reference to FIGS. 38-40, a resection guide 4500 is illustrated. The resection guide or apparatus can be used to resect any appropriate portion of the anatomy, such as the femur 12. As discussed further herein, the resection guide 4500 can be used to resect a femur in any appropriate manner, such as in a reduced invasiveness procedure, a minimal incision, or for any appropriate procedure. As discussed herein, the resection guide 4500 can be used to resect the femur 12 through any appropriate incision that can be formed in the anatomy, such as that discussed herein.

The resection guide 4500 can include any appropriate portions. The resecting guide can include a main body or resection section 4502, a first moveable or sliding guide section 4504 and a second sliding or moving resection section 4506. The moveable sections or moveable portions can also be referred to as a dynamic portion. The portions can be provided fixed or moveable relative to one another.

The first moving guide section 4504 can be used to cut a selected portion of the anatomy, such as an anterior portion of the femur to allow for implantation of a selected implant or prosthesis such as a distal femoral prosthesis. The first guide section 4504 can define a cutting slot 4508 by a first wall 4510, a second wall 4512, a third wall 4514, and a fourth wall 4516. Each of the walls, 4510-4516 can be formed of any appropriate material defining the cutting slot 4508. Further, the walls can be configured relative to one another in any appropriate manner. For example, the walls 4510-4516 can be welded together in any appropriate manner, such as a polygon, a rectangle, or the like. Further, the moving guide slot 4504 can include or be formed of a substantially single member in which the slot 4508 is machined or formed, rather than being formed by four separate wall members 4510-4516. Extending from the slot-defining member 4509 of the first guide portion 4504 is a stem or peg 4518. The stem 4518 can interconnect with a rail member 4520. The rail member 4520 can move or be fitted within a track or slot 4522 defined by the main body 4502. As discussed above, the rail member 4520 can be formed in any appropriate shape, such as a T-shape, a dovetail, a polygon, or the like. Further, it will be understood that the first guide member 4504 can substantially define a track member or portion while the main body 4502 defines a rail portion to interact therewith. Nevertheless, the interaction of the rail member 4520 and the track portion 4522 allows for the first guide portion of 4504 to move relative to the main body 4502.

The second guide portion 4506 can also define a guide body 4530 which defines a guide slot 4532 that is defined by a first wall 4534, a second wall 4536, a third wall 4538, and a fourth wall 4540. As discussed above, the various walls, 4534-4540 can be interconnected in a selected manner to define the guide slot 4532, that can be rectangular, or any appropriate shape. Further, the guide body 4530 can be formed of a single member from which the guide slot 4532 is defined such as with machining, cutting or the like. Further, a stem or peg 4542 extends from the guide body 4530 and interconnects with a second rail portion 4546. The rail portion 4546 can ride in a second track portion 4550 defined by the main body 4502. Similar to the first guide portion 4504, the body 4502 can define a second rail portion while the second guide portion 4506 defines a track portion. Nevertheless, the interconnection allows the second guide portion 4506 to move relative to the main body 4502. Further, as discussed herein, the second guide portion 4506 can be formed or positioned to resect any appropriate portion such as a posterior portion of a femur for reception of a selected implant or prosthesis, such as a distal femoral prosthesis.

The main body portion 4502, in addition to defining the two track portions 4522, 4550 also can define guide slots. For example, a first guide slot or guide portion 4560 can include the first guide surface or portion 4562, which can be on the front of the guide member 4502 and a second or back guide surface 4564. When positioned on a selected portion of the anatomy, such as the femur 12, the first guide portion 4560 can be used to form an anterior chamfer cut on the femur 12. Similarly, a second guide portion 4566 can define a first guide surface 4570 on a front portion of the guide body 4502 and a second guide surface 4572 on a back portion of the main guide portion 4502. The second guide surface 4566 can be used to form any appropriate resection, such as a posterior chamfer cut on a portion of the anatomy, such as the femur 12.

The main guide portion or body portion 4502 can define a longitudinal axis 4580. The longitudinal axis 4580 can generally define a longest portion or longest dimension of the main body portion 4502, the main body portion 4502 can define a dimension 4582 of any appropriate dimension. Generally, the dimension of 4582 can be selected to be about 75% of a maximum width of a distal femoral prosthesis to be positioned on a femur 12 on which the resection guide 4500 is used. It will be understood that the dimension 4582 can be about 2 cm to about 35 cm, and can be about 3 cm to about 10 cm.

The main body portion 4502 can also define, near the respective track portions 4522 and 4550 tapered or angle portions, such as a first angled portion 4584. The angled portion 4584 can define an angle 4586 relative to the longitudinal axis 4580. The angle 4586 can be any appropriate angle such as about 1° to about 89°. For example, the angle can be about 10° to about 60° to achieve a selected geometry of the main body portion 4502. The angle 4586 can be a selected angle to provide a minimum dimension 4590 defined by the main body portion 4502. It will be understood, therefore, that the main body portion 4502 can define angled portions 4584 on several portions of the main body. For example, a second angle portion 4592 can be defined on a side opposite from the first angled portion 4584. The second angled portion 4592 can also define an angle 4594 that is the same or complementary to the first angle 4586. It will also be understood that other angled portions, such as a third angled portion 4596 and a fourth angled portion 4598 can also be defined by the main body 4502. It will also be understood that the angled portions 4584, 4592, 4596, and 4598 can extend from substantially straight edges 4600 and 4602. The straight edges 4600, 4602 can extend between relative angled portions and be substantially perpendicular to the longitudinal axis 4580. The various dimensions of the main body portion 4502 can also include a dimension 4610. The dimension 4610 can be any appropriate dimension such as generally a dimension equivalent to a posterior to anterior dimension of a distal femoral implant to be positioned relative to the femur 12. Further, the dimension 4590 can be any appropriate dimension such as about 2 cm to about 10 cm. As discussed herein, various dimensions can be selected for dimension 4590 and can be selected based on patient requirements, user selection, or any appropriate reason.

As discussed above, the various portions, such as the first guide member 4504 and the second guide member 4506 can move relative to the main guide body 4502 and the track portions 4522 and 4550. The main body 4502 can define the stop portion 4620 and 4622 to assist in limiting a movement of the guide portions 4504, 4506 relative to the main body 4502. The stop portions 4620 and 4622 can be formed at any appropriate position on the main body portion 4502 to achieve a selected translation of the guide portions 4504, 4506 relative to the main body 4502.

The guide member 4500 can be formed of any appropriate material for a selected purpose, such as guiding a saw blade 4630 relative to a selected portion of the anatomy. For example, the resection guide 4500 can be formed of a metal, a metal alloy, a polymer, or any appropriate material. Nevertheless, the various portions of the resection apparatus 4500 can be formed of different materials for different purposes.

Figure 41:
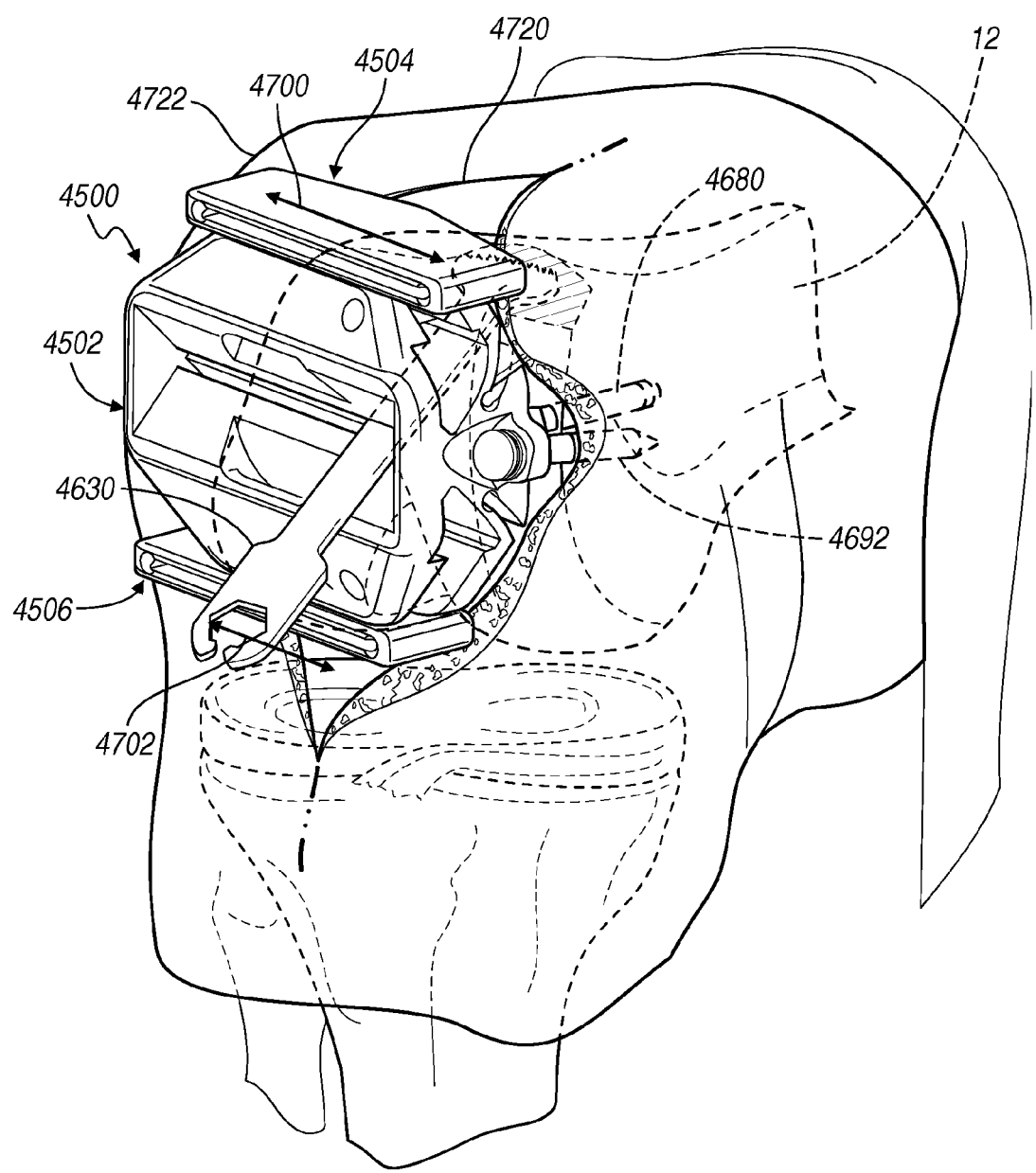
FIG. 41 is an environmental view of a guide apparatus in use.

With additional reference to FIG. 41, the bone resection apparatus 4500 can be interconnected with a femur 12 in a selected manner. For example, a single post 4680 and/or a second post 4682 can be provided to extend from the rear of the main body 4502 to extend into the femur 12. For example, the two posts 4680, 4682 can be positioned in pre-formed holes or drill holes that have been provided in the femur 12 for various purposes, such as those generally understood in the art. It will be understood that the two posts 4680, 4682 can be provided alone or in combination with other connection apparatuses to be fixed into the femur 12. For example, the main body portion 4502 can define a first flange 4684 that can define a first bore 4686 and a second flange 4688 that defines a second bore 4690. The bores 4686, 4690 can be provided to receive a first pin 4692 and a second pin 4694. The pins 4692, 4694 can assist to further interconnect the resection apparatus 4500 with the femur 12. It will be understood that the interconnection can be provided in any appropriate manner, and both the posts 4680, 4682 and the pins 4692 and 4694 are merely exemplary. It will be understood that one skilled in the art can provide more than one fixation portion on the apparatus 4500 or it can be provided with any appropriate combination. Further, it will be understood that various additional portions can be provided to interconnect the resection apparatus 4500 with the femur 12.

Nevertheless, the interconnection of the resection apparatus 4500 with the femur 12 can allow for resection of various portions of the femur 12 for various purposes, such as connecting a prosthesis with the distal portion of the femur 12. As discussed above, the first guide portion 4504 and the second guide portion 4506 can move relative to the main body portion 4502 in a selected manner. For example, the first guide portion 4504 can move in the direction of arrow 4700 relative to the main body 4502. Further, the second resection or guide portion 4506 can move in the direction of arrow 4702 relative to the main body 4502. Generally, the direction arrows 4700 and 4702 can define movement either medial or lateral relative to the femur 12. Therefore, a saw blade or other cutting instrument that is positioned within the guide slots 4508 and 4532, respectively, can be used to resect an entire anterior or posterior portion of the femur 12 without moving the main body portion of 4502 and without providing the guide bodies 4504 and 4506 to span an entire dimension of the femur 12, such as a medial-lateral dimension. Further, the guide bodies 4504, 4506 can include a selected dimension, such as a longitudinal dimension 4710 and 4712. The dimensions 4710 and 4712 can be the same or different, depending upon a selected reason. For example, it may be selected to provide the first guide portion 4504 with a larger dimension 4712 than the dimension 4710 if the anterior resection is generally larger than the posterior resection. Nevertheless, the dimensions 4710, 4712 can be provided in a selected dimension such that it does not span the entire dimension of the femur 12, such as an epicondyle width, yet the saw blade can be maintained within the respective guide slots 4508 and 4532 to form an entire or substantially entire resection of the femur 12. It will be understood, however, that the resection of the femur 12 can also be substantially performed with a saw blade within the respective guide slots 4508 and 4532 while a minor completion of the cut is formed substantially freehand.

Nevertheless, the guide assembly 4500 can be provided to resect a selected portion of the femur 12 to substantially resect the entire portion of the femur 12 with the saw within a respective guide slot. Either the saw can be maintained within the guide slot 4508 and 4532 of the moveable guide portions 4504 and 4506, or the saw blade can be maintained within the guide surfaces 4566 and 4560 of the main body portion 4502.

As illustrated in FIG. 41, the resection apparatus 4500 can be interconnected with the selected bone, such as a distal end of the femur. It will be understood that various other resections or resected surfaces can be formed on the femur 12 in a selected manner, such as using a distal resection guide, a mill, a drill, or the like. For example, the fixation pins 4680 can be inserted into pre-drilled or pre-formed holes formed in the femur 12. The pins 4680 can be sized to engage the bone 12 in a selected manner to hold the main body 4502 in a selected position.

Once the main body 4502 is fixed relative to the femur 12, a resection can be formed on the femur 12. For example, the dynamic guide resection portions 4504 and 4506 can be used to guide a resection of the selected portions of the femur 12. It will be understood that either of the dynamic resection guide portions 4504, 4506 or only a single one may be provided or used during a selected procedure. Further, the main body 4502 can be provided to act as a member to allow movement of the dynamic guide resection portions 4504, 4506 relative to the femur 12 and not act to define any guide surfaces in and of itself. Therefore, it will be understood that the guide surfaces 4560 and 4566 are exemplary illustrated and are not required on the main body 4502.

Once the resections on the portion of the femur 12 are formed using the resection guide 4500, and any other preparation has occurred, a distal femoral implant, including those illustrated below in FIG. 42, can be implanted relative to the femur 12. It will be understood that the femur 12 can be prepared in any appropriate manner, such as further resections, a mill, a drill and connections mechanisms such bone cement, (e.g., polymethylmethacrylate) can be used. Therefore the resection apparatus 4500 can be used to resect a selected portion of the anatomy, including the femur 12, to assist in preparing the selected portion of the anatomy for implantation of a selected prosthesis. Nevertheless, the various portions of the resection apparatus 4500, such as either or both of the dynamic resection portions 4504, 4506 can be moved relative to another portion of the resection apparatus 4500 to achieve a selected result or to guide a selected instrument during a resection procedure.

As discussed above, the various dimensions of the guide apparatus 4500 can be used to provide a selected incision 4720 in a soft tissue 4722 surrounding the femur 12. The incision 4720 can be any appropriate dimension, such as a length of about 4 cm to about 15 cm. The dimension of the guide apparatus 4500 can be provided to achieve a selected resection of the femur 12 within the incision size. It will be understood that various incision sizes may be dependent upon the anatomy of the patient, such as male or female, or dimension of the femur 12, the amount of soft tissue surrounding the femur 12, and other appropriate considerations. Therefore, it will be understood that the various dimensions of the guide apparatus may be chosen or formed to achieve a selected result pre-operatively, intra-operatively, or the like.

The guide apparatus 4500 can be formed, including the angled portions and other appropriate dimensions to achieve a selected result. For example, as illustrated in FIG. 41, the guide apparatus 4500 can be provided to be fit within the incision 4720 without substantially lengthening the incision beyond a selected length. Therefore, the incision can be moved relative to the guide apparatus 4500 to provide for guiding the saw blade to achieve a selected cut while substantially maintaining the saw blade within the guide slot, and providing for a smaller incision. As one skilled in the art will understand, the incision can be more easily stretched or pulled near a center point of the incision while not at its ends, therefore, the guide apparatus 4500 can be provided to fit within the selected incision length.

Figure 42:
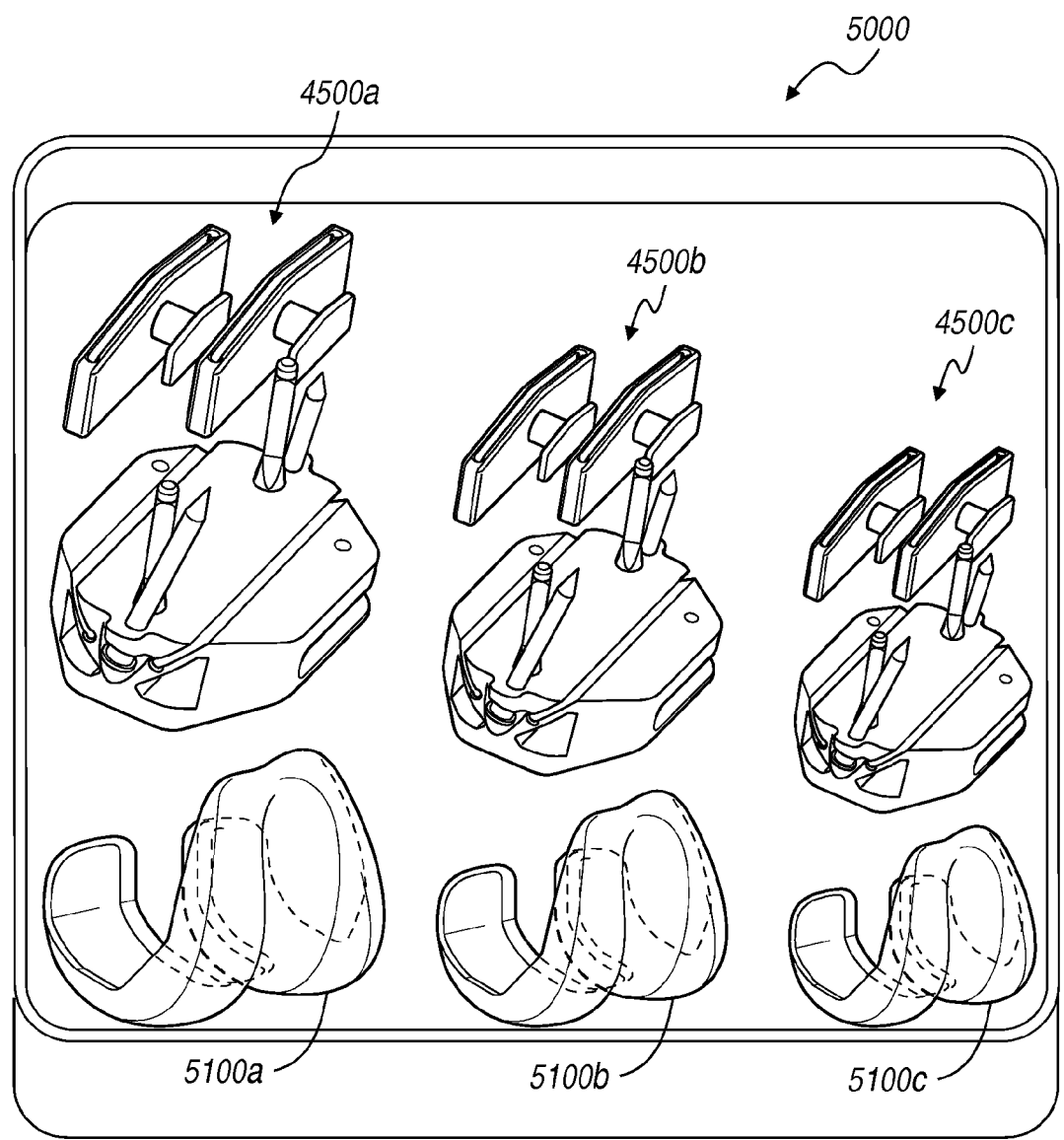
FIG. 42 is a plan illustration of a kit including a guide apparatus according to various embodiments.

Further, the guide apparatus 4500 can be provided as a plurality of guide apparatuses in a kit 4800, illustrated in FIG. 42. For example, the kit 4800 can include three of the guide apparatuses 4500a, 4500b and 4500c, and each of the various apparatuses can have different dimensions, such as the dimension 4582 being 4582a, 4582b, 4582c, or the like. The dimensions 4582a-c, can be selected to be different among the various of the guide apparatuses 4500a-4500c. Each of the different dimensions 4582a-c can vary depending upon a distal femoral prosthesis 4802, 4804, and 4806. The different distal femoral prostheses can include different dimensions that can vary depending upon a patient, an anatomy, a gender, or the like. It will be understood, however, that the distal femoral prostheses can generally include a different dimension based upon an anatomy of the patient or the like, but can be generally included in the kit 4800 for selection by a user during a procedure. This can allow for intra-operative customization or other various purposes when performing a procedure. Nevertheless, the plurality of the cutting blocks 4500a-4500c can also be provided to allow for a substantially unique resection of the femur 12 based upon the selected prosthesis to be positioned relative to the femur 12. Therefore a user, such as a surgeon, can select the appropriate prosthesis, the appropriate resection tool, and perform a selected procedure. It will be understood that the customization can be dependent upon a user's expertise, but a plurality can be provided for a selected customization of use.

The description is merely exemplary in nature and, thus, variations that do not depart from the gist of the description are intended to be within the scope of the following claims. Such variations are not to be regarded as a departure from the spirit and scope of the following claims.

What is claimed is:

1. A system for performing a resection of a selected portion of an anatomy with a resection instrument, the system comprising:
   a first member fixable to the selected portion of the anatomy;
   a first movement defining portion defined by the first member;
   a second member configured to cooperate with the first member, the second member including a guide surface configured to guide a resection instrument during the resection; and
   a second movement defining portion of the second member;
   wherein the first movement defining portion and the second movement defining portion are operable to allow the second member to be moveable relative to the first member from a first position to a second position such that the guide surface of the second member remains in the same plane; and
   wherein the resection instrument is positionable relative to the second member in the first position and in the second position to form a selected resection of the selected portion of the anatomy.

2. The system of claim 1, wherein the first member includes a support block and the first movement defining portion includes a groove configured to slidably and rotatably receive the second movement defining portion.

3. The system of claim 2, wherein the second movement defining portion is a peg.

4. The system of claim 2, wherein the groove is curved.

5. The system of claim 1, wherein the second member is a cutting guide defining a guide slot configured to receive the resection instrument therein.

6. The system of claim 1, further comprising a fixation member that extends from the first member and is operable to fix the first member relative to the selected portion of the anatomy.

7. The system of claim 1, wherein the first movement defining portion and the second movement defining portion are operable to allow the second member to be slidably and rotatably moveable relative to the first member.

8. The system of claim 1, further comprising a stylus including a tip at a distal end thereof, the first member includes a plurality of coupling members configured to cooperate with the stylus to secure the stylus to the first member and position the tip proximate to the selected portion of the anatomy.

9. A system for resecting a proximal tibial portion with a resection instrument, the system comprising:
   a main guide portion;
   a first dynamic connection portion included with the main guide portion;
   a dynamic guide member;
   a guide surface defined by the dynamic guide member and configured to guide the resection instrument during resection of the proximal tibial portion; and
   a second dynamic connection portion included with the dynamic guide member, the first and the second dynamic connection portions are configured to cooperate with one another to guide movement of the dynamic guide member and the guide surface while the guide surface of the second member remains in the same plane.

10. The system of claim 9, wherein the second dynamic connection portion is complementary to the first dynamic connection portion to allow movement of the dynamic guide member relative to the main guide portion.

11. The system of claim 9, wherein the guide surface defined by the dynamic guide member includes a fully contained passage.

12. The system of claim 9, wherein the first dynamic connection portion is a curved groove defined in the main guide portion.

13. The system of claim 9, wherein the second dynamic connection portion is a peg.

14. The system of claim 9, wherein the first and the second dynamic connection portions are configured such that cooperation therebetween slidably and rotatably guides movement of the dynamic member and the guide surface.

* * * * *